US006495674B1

(12) United States Patent
Lemke et al.

(10) Patent No.: US 6,495,674 B1
(45) Date of Patent: Dec. 17, 2002

(54) EVECTINS AND THEIR USE

(75) Inventors: Greg Erwin Lemke, La Jolla, CA (US); Andrew Do Nguyen, San Diego, CA (US); Ralf Krappa, Tornesch (DE)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/511,881

(22) Filed: Feb. 25, 2000

(51) Int. Cl.$^7$ .............................................. C12N 15/12
(52) U.S. Cl. ....................................... 536/23.5
(58) Field of Search ....................................... 536/23.5

(56) References Cited

PUBLICATIONS

Johannes et al, Protein kinase Cu downregulation of tumor–necrosis–factor–induced apoptosis correlates with enhanced expression of nuclear–factor–kB–dependent protective genes, 1998, Eur. J. Biochem, 257, 47–54.*
Johannes, et al, PKCu is a Novel, Atypical Member of the Protein Kinase C Family, 1994, The Journal of Biological Chemistry, vol. 269 No. 8. pp. 6140–6148.*
Valverde et al, Molecular cloning and characterization of protein kinase D: A target for diacylglycerol and phorbol esters with a distinctive catalytic domain, Aug. 1994, Biochemistry, vol. 91, pp. 8572–8576.*
Atkins et al., "Regulation of myelin basic protein phosphorylation by mitogen–activated protein kinase during increased action potential firing in the hippocampus," *J. Neurochem.*, 73:1090 (1999).
Banfi et al., "Genetwork, How to get the best of dbEST," *Trends Genet.*, 14:80–81 (1998).
Besharse, *The Retina: A Model for Cell Biological Studies*, Adler and Farber, eds., Academic Press, New York, 1986:297–352.
Blackshaw and Snyder, "Developmental expression pattern of phototransduction components in mammalian pineal implies a light–sensing function," *J. Neurosci.*, 17:8074–8082 (1997).
Boman and Kahn, "Arf proteins: the membrane traffic police?" *Trends Biochem. Sci.*, 20:147–150 (1995).
Bretscher, "Moving membrane up to the front of migrating cells," *Cell*, 85:465–467 (1996).
Cockcroft, "Phosphatidylinositol transfer proteins: a requirement in signal transduction and vesicle traffic," *Bioessays*, 20:423–432 (1998).
Criswick and Schepens, "Familial exudative vitreoretinopathy," *Am. J. Ophthalmol.*, 68:578–594 (1969).
Dudek et al., "Regulation of neuronal survival by the serine–threonine protein kinase Akt," *Science*, 275:661–665 (1997).
Erickson, et al., "Identification by mass spectrometry of threonine 97 in bovine myelin basic protein as a specific phosphorylation site for mitogen–activated protein kinase," *J. Biol. Chem.*, 265(32):19728–35, Nov. 15, 1990.

Kilpatrick et al., "Expression of the *Tyro4/Mek4*/Cek4 gene specifically marks a subset of embryonic motor neurons and their muscle targets," Mol. *Cell Neurosci.*, 7:62–74 (1996).
Krappa et al., "Evectins: vesicular proteins that carry a pleckstrin homology domain and localize to post–Golgi membranes," *Proc. Natl. Acad. Sci. USA*, 96:4633–4638 (1999).
Lemmon and Ferguson, "Pleckstrin homology domains," *Curr. Top. Microbiol. Immunol.*, 228:39–74 (1998).
Levine and Munro, "The pleckstrin homology domain of oxysterol–binding protein recognizes a determinant specific to Golgi membranes," *Curr. Biol.*, 8:729–739 (1998).
Li et al., "The autosomal dominant familial exudative vitreoretinopathy locus maps on 11q and Ls closely linked to DllS533," *Am. J. Hum. Genet.*, 51:749–754 (1992).
Luini and De Matteis, "Receptor–mediated regulation of constitutive secretion," *Trends Cell Biol.*, 3:290–292 (1993).
Luttrell, LM., et al., "Effect of cellular expression of pleckstrin homology domains on $G_i$–coupled receptor signaling," *J.Biol. Chem.* 270(22): 12984–9, Jun. 2, 1995.
Mellman, "Endocytosis and molecular sorting," *Annu. Rev. Cell Dev. Biol.*, 12:575–562 (1996).
Metin et al., "A role for netrin–1 in the guidance of cortical efferents," *Development*, 124:5063–5074 (1997).
Monuki et al., "SCIP: A glial POU domain gene regulated by cyclic AMP," *Neuron*, 2:783–793 (1989).
Muller–Weeks and Caradonna, "Specific association of cyclin–like uracil–DNA glycosylase with the proliferating cell nuclear antigen," *Exp. Cell Res.*, 226:346–355 (1996).
Pfeiffer et al., "The oligodendrocyte and its many cellular processes," *Trends Cell Biol.*, 3:191–197 (1993).
Pitcher, et al., "Pleckstrin homology domain–mediated membrane association and activation of the β–adrenergic receptor kinase requires coordinate interaction with $G_{\beta\gamma}$ subunits and lipid," *The American Society for Biochemistry and Molecular Biology*, 270(20):11707–11710, 1995.
Price et al., "Familial exudative vitreoretinopathy linked to D11S533 in a large Asian family with consanguinity," *Ophthalmic Genet.*, 17:53–57 (1996).
Ridsdale et al., "Three–dimensional structure of myelin basic protein," *J. Biol. Chem.* 272:4269 (1997).
Sasaki., T., et al., "The Rho small G protein family–Rho GDI system as a temporal and spatial determinant for cytoskeletal control," *Biochem. Biophys. Res. Commun.*, 245(3):641–5, Apr. 28, 1998.

(List continued on next page.)

Primary Examiner—John S. Brusca
(74) Attorney, Agent, or Firm—Knobbe Marten Olson & Bear LLP

(57) ABSTRACT

The present invention relates generally to the field of neurobiology. More particularly, the invention relates to the discovery of a new family of proteins and their relation to signal transduction, vesicle trafficking, and diseases associated with aberrations in membrane biosynthesis and organization.

3 Claims, 7 Drawing Sheets

OTHER PUBLICATIONS

Sawai, T., et al., "Interaction between Pleckstrin homology domains and G protein βγ–subunits: Analyses of kinetic parameters by a biosensor–based method," *Biol. Pharm. Bull.*, 22(3):229–33, Mar. 1999.

Schmid et al., "Dynamin and its partners: a progress report," *Curr. Opin. Cell Biol.*, 10:504–512 (1998).

Schulz, P., et al., "Endogenous phosphorylation of basic protein in myelin of varying degrees of compaction," *Biochem.* 27(20):7793–9, Oct. 4, 1988.

Touhara K., et al., "Binding of G protein βγ–subunits to pleckstrin homology domains," *J. Biol. Chem.*, 269(14):10217–20, Apr. 8, 1994.

Xu et al., PHR1 encodes an abundant, pleckstrin homology domain–containing integral membrane protein in the photoreceptor oute segments, *J. Biol. Chem.*, 274(50): 35676–35685, Dec. 10, 1999.

\* cited by examiner

FIG. 1

| FIG. 1A |
|---------|
| FIG. 1B |

EVECTINS AND THEIR USE

This work was supported in part by Grant Nos. NS23896, NS31249, NS34803 and NS39574 from the National Institutes of Health. Consequently, the U.S. government may have certain rights to this invention.

FIELD OF THE INVENTION

The present invention relates generally to the field of neurobiology. More particularly, the invention relates to the discovery of a new family of evectin proteins and their relation to signal transduction, vesicle trafficking, and diseases associated with aberrations in membrane biosynthesis and organization.

BACKGROUND OF THE INVENTION

Photoreceptors, oligodendrocytes, and myelinating Schwann cells are highly polarized cells that synthesize an exceptionally large, apically-configured organelle composed almost entirely of extended sheets of tightly compacted and specialized plasma membrane. The compacted disks of the photoreceptor rod outer segments or "ROS" and the compacted laminae of myelin look remarkably similar and there are no other cell types in the body that maintain the extraordinarily high levels of membrane biosynthesis and maintenance that are characteristic of these cells. These cells regulate the production of plasma membrane, the secretion of proteins (e.g., the proteolipid protein in myelin and rhodopsin in rods), and the localization of lipids and proteins in response to environmental stimuli. (Luini and De Matteis, *Trends Cell Biol.*, 3:290–292 (1993); Bretscher, *Cell*, 85:465–467 (1996); (Blackshaw and Snyder, *J. Neurosci.*, 17:8074–8082 (1997); Mellman, *Annu. Rev. Cell Dev. Biol.*, 12:575–562 (1996); and Cockcroft, *Bioessays*, 20:423–432 (1998)).

A differentiating neuron, for example, can organize membrane biosynthesis and protein localization such that its growing axon extends over great distances toward the source of a chemoattractant. (Metin et al., *Development*, 124:5063–5074 (1997)). Oligodendrocytes of the vertebrate brain elaborate extraordinary quantities of specialized membrane (~5,000 $\mu m^2$ per day) in response to molecular cues that trigger their myelination of axons. (Pfeiffer et al., *Trends Cell Biol.*, 3:191–197 (1993)). Defective molecular signaling, which results in aberrant biosynthesis and organization of membrane in these cells, has been associated with human diseases such as Multiple Sclerosis (MS), an autoimmune disease that results in demyelination of CNS axons and oligodendrocyte death. (Ridsdale et al., *J Biol Chem.* 272:4269 (1997) and Atkins et al., *J. Neurochem.* 73:1090 (1999).

Vertebrate photoreceptors also achieve similar rates of membrane biosynthesis in the course of assembling and maintaining their outer segments. (Besharse, *The Retina: A Model for Cell Biological Studies*, Adler and Farber, eds., Academic Press, New York, 1986:297–352). Aberrations in biosynthesis and organization of membrane in cells of the retina have been associated with human diseases such as autosomal dominant familial exudative vitreoretinopathy (adFEVR), an inherited disorder characterized by inflammation of retinal blood vessels, neovascularization and vascular drop-out, generalized hyperpermeability of retinal vessels, and consequent retinal degeneration. (Criswick and Schepens, *Am. J. Ophthalmol.*, 68:578–594 (1969)). For all of the above reasons, it is important to identify molecules that link extracellular signals to changes in membrane biosynthesis and organization.

SUMMARY OF THE INVENTION

The discovery of a new family of proteins and nucleic acids encoding these proteins is revealed in this disclosure. This family of molecules is characterized by a structure having a pleckstrin homology domain (PHD), a protein-protein interaction module, a phosphorylation domain, and a hydrophobic domain. The first member of the family discovered was named evectin-1 ("evt-1"), from the Latin evectus, meaning carried or moved forward. A second member of the family, which bears 40% total homology to evt-1 but greater homology within regions of the molecule, is named evectin-2 ("evt-2").

Embodiments of the invention include a purified or isolated nucleic acid encoding a polypeptide having a pleckstrin homology domain and a hydrophobic membrane-binding domain. This molecule can also have a nucleic acid sequence encoding a protein binding domain or a nucleic acid sequence encoding a phosphorylation domain. Nucleic acids encoding evectins, evectin polypeptides, and fragments of these molecules are embodiments of the invention. Some embodiments also concern a nucleic acid having a nucleotide sequence selected from the group consisting of: SEQ. ID. NO: 1, SEQ. ID. NO: 2, SEQ. ID NO: 3, SEQ. ID. NO: 4, SEQ. ID. NO: 5, SEQ. ID. NO. 11, and SEQ. ID. NO. 12 or a sequence complementary thereto. Further embodied in this invention are purified or isolated nucleic acid sequences encoding a polypeptide having an amino acid sequence selected from the group consisting of: SEQ ID NO: 6, SEQ ID NO: 7, SEQ ID NO: 8, SEQ ID NO: 9 and SEQ ID NO: 10.

Other embodiments include purified or isolated polypeptides having a pleckstrin homology domain and a hydrophobic domain. As above, these molecules can further include a protein binding domain and/or a phosphorylation domain. Evectins, evectin polypeptides, and fragments of these molecules are embodiments of the invention. Some polypeptides of the invention also have an amino acid sequence selected from the group consisting of SEQ ID NO: 6, SEQ ID NO: 7, SEQ ID NO: 8, SEQ ID NO: 9 and SEQ ID NO: 10.

Antibodies to evectins are also embodiments. These antibodies can be monoclonal or polyclonal. One example are antibodies capable of specifically binding to a protein comprising an amino acid sequence selected from the group consisting of: SEQ ID NO: 6, SEQ ID NO: 7, SEQ ID NO: 8, SEQ ID NO: 9 and SEQ ID NO: 10. Some of these antibodies can specifically bind to a polypeptide comprising at least 10 consecutive amino acids of said protein. Desirable antibodies of the invention are capable of specifically bind to evt-1 protein, but not to evt-2 protein or vice versa (i.e., a purified or isolated antibody capable of specifically binding evt-2 protein, but does not specifically bind evt-1 protein).

Methods of identifying a binding partner that interacts with evt-1 or evt-2 is also an embodiment. By one approach, a support comprising evt-1, evt-2 or a representative fragment thereof is provided; the support is contacted with a candidate binding partner; and a biological complex comprising evt-1 or evt-2; and the candidate binding partner, is detected. The detection of such a complex indicates that said candidate binding partner interacts with evt-1 or evt-2.

A computerized system for identifying an agent that interacts with evt-1 or evt-2 is also an embodiment. One embodiment, for example, includes a first data base comprising protein models of the amino acid sequences as set forth in SEQ. ID. NOS. 6–10; a second data base comprising the composition of a plurality of candidate binding partners; a search program that compares the protein model of the first data base with the compositions of the candidate agents of the second database; and a retrieval program that identifies a candidate binding partner that interacts with the protein model of the first database. In some embodiments, the candidate binding partners are selected from the group consisting of: a peptide, a peptidomimetic, and a chemical. Another related embodiment concerns a computer-based system for identifying a target sequence having homology to an evectin molecule. This system includes a database comprising one of the sequences of SEQ ID NOS: 1–12 or a representative fragment thereof; a search program that compares a target sequence to sequences in the database to identify homologous sequence(s), and a retrieval program that obtains said homologous sequence(s).

A method of identifying an organism in need of treatment or prevention of a defect in vesicle trafficking, signal transduction, G protein binding, or membrane biosynthesis and organization is also an embodiment of the invention. This method is practiced by obtaining a biological sample comprising RNA or protein from an organism; providing a probe that interacts with an evt protein or an RNA encoding an evt protein; contacting the biological sample with the probe under conditions that allow the probe to bind to the evt protein or the probe to bind with the RNA encoding an evt protein in the biological sample; detecting the amount of probe that interacts with the evt protein or the RNA encoding an evt protein in the biological sample so as to determine the concentration or level of expression of the evt protein or the RNA encoding an evt protein; and identifying the organism as an organism in need of treatment or prevention of a defect in vesicle trafficking, signal transduction, G protein binding, or membrane biosynthesis and organization based on the concentration or level of expression of the evt protein or the RNA encoding an evt protein detected in the sample.

Another way to identify an agent that modulates evt-mediated signal transduction involves providing a support having an evt protein or a representative fragment thereof; contacting the support with a binding partner that binds to the evt protein or representative fragment thereof; contacting the support with a candidate agent; and detecting the presence or absence of binding of the binding partner to the evt protein and thereby identifying the agent as one that modulates evt-mediated signal transduction.

Another embodiment of the invention concerns a knockout mouse, wherein the wild-type evt-1 gene is replaced with a mutant evt-1 gene. Furthermore, a method for producing a genetically altered mouse that exhibits a defect in vesicle trafficking, signal transduction, G protein binding, or membrane biosynthesis and organization is an aspect of the invention. This method is practiced by providing an evectin gene targeting construct comprising an evt-1 gene having a modification resulting in an amino acid substitution; introducing said evt-1 gene having a modification resulting in an amino acid substitution and a selectable marker sequence into a mouse embryonic stem cell; introducing said mouse embryonic stem cell into a mouse embryo; transplanting said embryo into a pseudopregnant mouse; allowing said embryo to develop to term; identifying a genetically altered mouse whose genome comprises a modification of the evt-1 gene in both alleles; and breeding the genetically altered mouse of step (f) to obtain a genetically altered mouse whose genome comprises a modification of the endogenous evt-1 gene, wherein said disruption results in said mouse exhibiting a defect in vesicle trafficking, signal transduction, G protein binding, or membrane biosynthesis and organization.

BRIEF DESCRIPTION OF THE DRAWINGS

Figures 1, 1A, 1B:
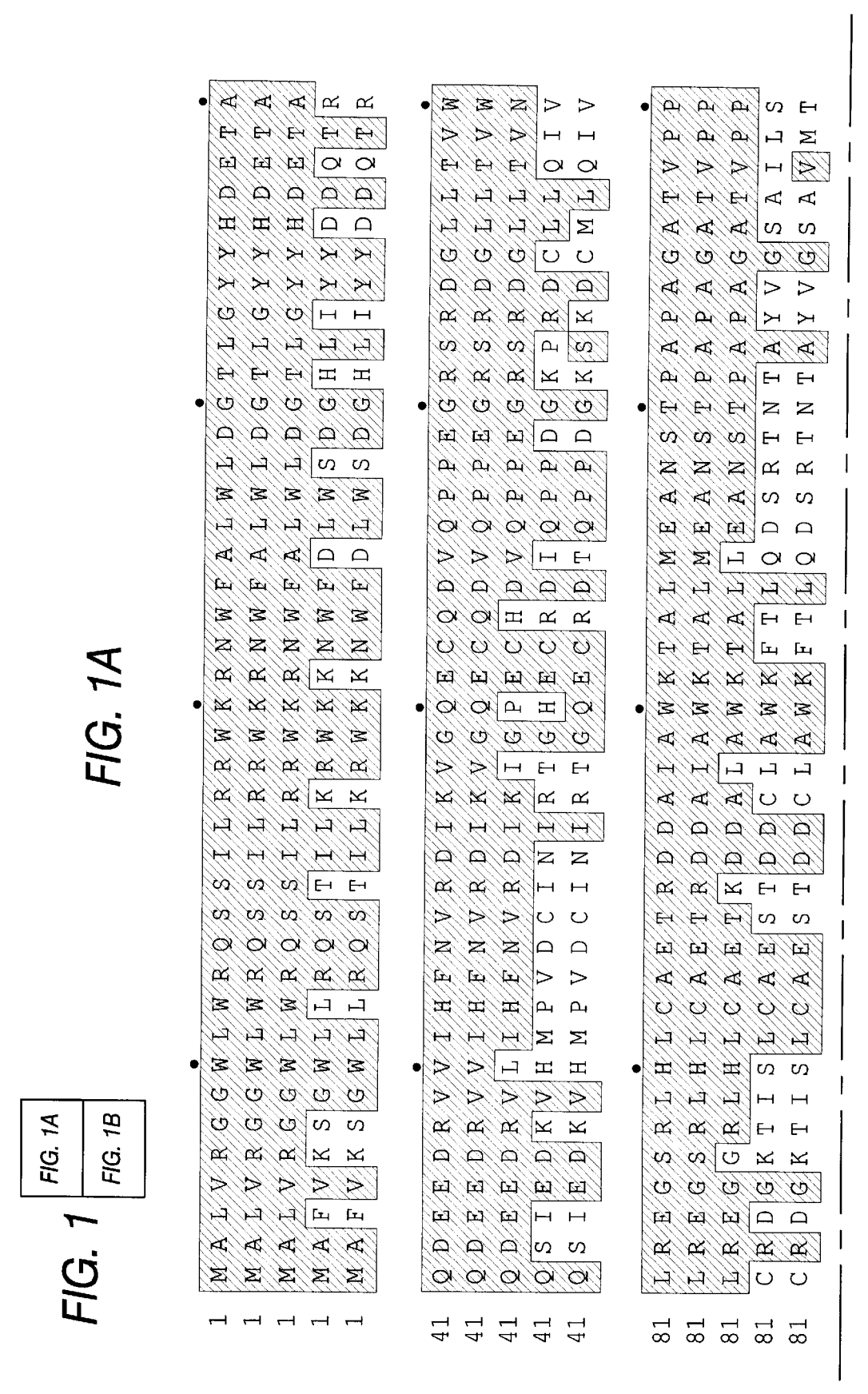

FIG. 1 is an alignment of the amino acid sequences of rat (SEQ ID NO: 6), mouse (SEQ ID NO: 7), and human (SEQ ID NO: 8) evt-1 sequences and mouse (SEQ ID NO: 9) and human (SEQ ID NO: 10) evt-2 sequences, wherein the amino acid identities with rat evt-1 are indicated in black.

DETAILED DESCRIPTION OF THE INVENTION

Figures 2, 2A:
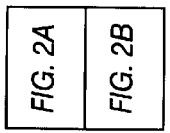
FIG. 2 is an alignment of the amino acid sequences of the evectin pleckstrin homology domains (PHD) to the most closely related PHDs in public databases, wherein the amino acid identities with rat evt-1 (SEQ ID NO: 6) are indicated in black and the conservative substitutions are indicated in gray. The compared sequences are evt-2 (mouse) (SEQ ID NO: 9), akt (rat) (SEQ ID NO: 13), OSBP (human) (SEQ ID NO: 14), dynamin (mouse) (SEQ ID NO: 15), ARNO (human) (SEQ ID NO: 16), and pleckstrin-N (human) (SEQ ID NO: 17).
Figure 2B:
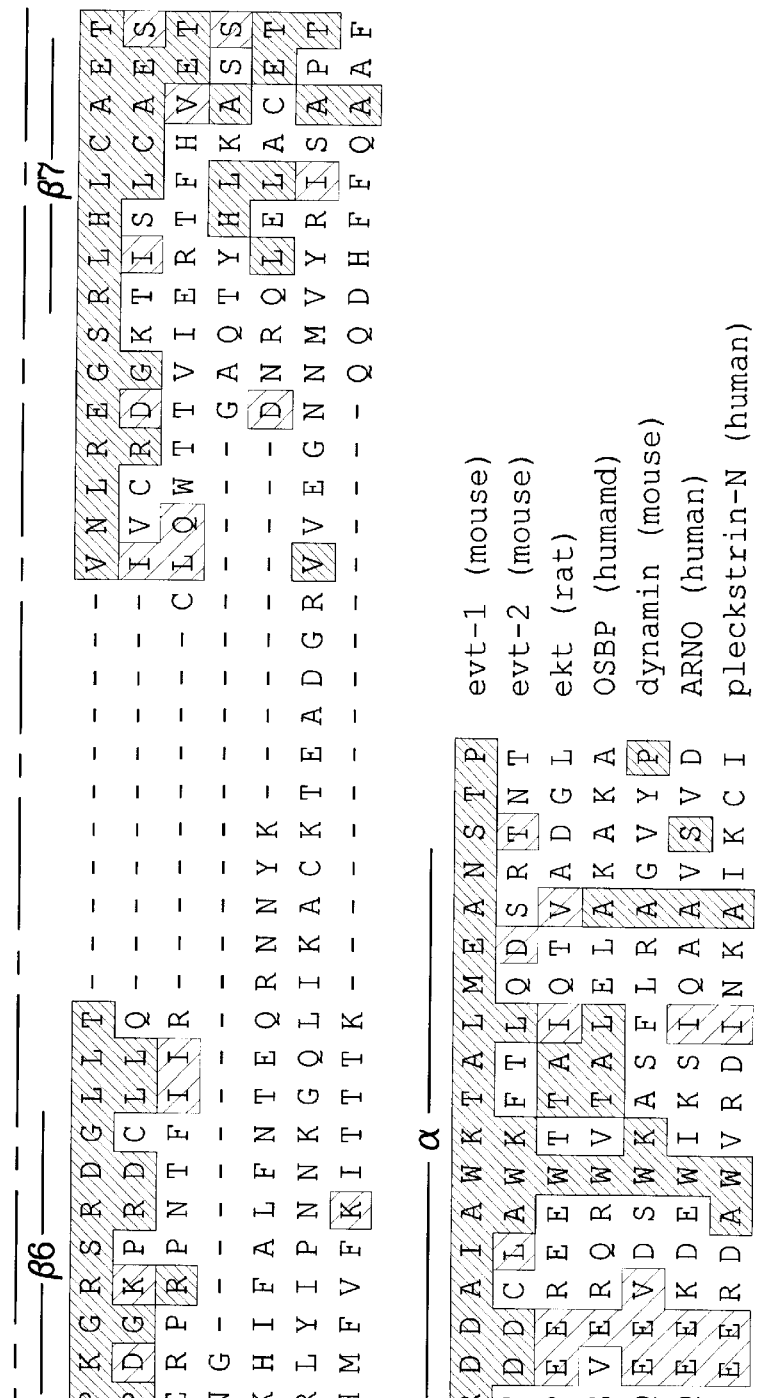

A new family of structurally distinctive proteins, designated evectins, have been discovered. Two members of this family have been identified, cloned, sequenced, and characterized. These proteins can be identified by their four domains: a pleckstrin homology domain (PHD), a protein-protein module, a phosphorylation domain, and a hydrophobic domain. Notably, evectins lack a cleaved N-terminal signal sequence, can be inserted into membranes through a C-terminal hydrophobic anchor, and the pleckstrin homology domain at the N-termini can couple these molecules to signal transduction pathways. A first member of the family, referred to as evt-1, is specific to the nervous system, where it is expressed in photoreceptors and myelinating glia. A second member of the family, referred to as evt-2, is widely expressed in both neural and non-neural tissues.

Data is presented in the following disclosure that demonstrates human evt-1 maps to an interval within chromosome 11q13 at 80–84cM from the centromere, between markers D11S916 and D11S911. In addition, evt-1 is expressed in photoreceptors, pigment epithelium, pinealcytes, oligodendrocytes, and ependymal cells. Evt-2 expression is detected in neurons, hippocampal fields and overlying cortex, and the neocortex but not the ependyma or white matter tracts. Morphologically, evt-1 is approximately 25 kD and exists in a modified and unmodified form. Moreover, evt-1 was found to associate with membranes. Additionally, an evt-1 knockout mouse exhibited a phenotype characterized by a loss of the buffer zone between axons.

Several embodiments of the invention have biotechnological, diagnostic, and therapeutic use. For example, the nucleic acids of the invention and/or proteins of the invention can be used as probes to isolate more evectins, detect the presence of wild type or mutant evectins in various tissues, and can be incorporated into constructs for preparing recombinant evectin proteins or can be expressed from such constructs. The sequences of the nucleic acids of the invention and/or proteins of the invention can also be incorporated into computer systems, used with modeling software so as to enable some forms of rational drug design. The nucleic acids of the invention and/or proteins of the invention, as well as, the binding partners of the invention, can be incorporated into pharmaceuticals and used for the treatment of retinal diseases and neuropathies.

The nucleic acid embodiments of the invention include nucleotides encoding evectin molecules and fragments thereof and variants such as spliced variants, allelic variants, synonomous sequences, and homologous or orthologous molecules. Some embodiments for example, include genomic DNA, RNA, and cDNA encoding evectins. The nucleic acid embodiments of the invention also include partial or complete DNA sequences shown in the sequence listing (SEQ. ID. NOS. 1–5, 11, and 12), nucleotide sequences encoding the amino acid sequences shown in the sequence listing (SEQ. ID. NOS. 6–10) and complements thereof. Nucleic acid sequences encoding evectins from other organisms are also embodiments of the invention, as are methods for obtaining such sequences. The nucleic acid embodiments can be altered, mutated, or changed such that the alteration, mutation, or change results in a conservative amino acid replacement. The nucleic acid embodiments can also be altered, mutated, or changed such that the alteration, mutation, or change results in a non-conservative amino acid replacement. Some embodiments of the invention, for example, include nucleic acids encoding evectin molecules that have one or more of the evectin domains deleted or combined in a novel fashion so as to create an "evectin-like hybrid" molecule. Further, some embodiments relate to nucleic acids encoding evectin-like hybrids having multimerized domains, synthetic domains, and domains from other signal transduction proteins.

The polypeptide embodiments of the invention include partial or complete amino acid sequences shown in the sequence listing (SEQ. ID. NOS. 6–10) and functional equivalents to such molecules including, but not limited to, the polypeptides of SEQ. ID. NOS. 6–10 having nonconservative amino acid substitutions and peptidomimetics that resemble these molecules. Additional polypeptide embodiments include mutant evectins having nonconservative amino acid replacements, in particular mutants that result in gain or loss of evectin function. Further, the polypeptide embodiments include evectin-like hybrids having one or more of the evectin domains deleted or combined in a novel fashion or multimerized domains, synthetic domains, and domains from other signal transduction proteins. Polypeptides that are homologous to evt-1 and/or evt-2 are also embodiments of the invention and methods of obtaining such molecules are provided. Additionally, methods of preparing the polypeptide embodiments of the invention through chemical synthesis and recombinant techniques are disclosed. Approaches to creating genetically altered organisms that express either a wild-type or mutant evectin transgene (i.e. evectin transgenic or knockout animals) are also provided as discussed below.

Embodiments of the invention also include antibodies that recognize wild-type and mutant evectins. Approaches to manufacture monoclonal and polyclonal antibodies are disclosed. For example, an anti-evt-1 antibody was prepared and was found to detect both mammalian and amphibian evt-1.

Approaches to rational drug design are also provided in this disclosure, and these methods can be used to isolate new evectin family members and to identify molecules that interact with the evectins, referred to as "binding partners". Several computer-based methodologies are discussed, which involve three-dimensional modeling of the evectin nucleic acid and/or protein sequences and the nucleic acid and protein sequences encoding known or suspected binding partners (e.g., antibodies and G proteins or G protein subunits).

Evectin characterization assays are also described herein. These assays test the functionality of an evectin molecule and identify binding partners that interact with the evectins. Some functional assays involve the use of multimeric evectins and/or binding partners, which are evectins, hybrids, or binding partners disposed on a support, such as a resin, bead, lipid vesicle or cell membrane. These multimeric agents are contacted with candidate binding partners and the association of the binding partner with the multimeric agent is determined. Successful binding agents can be further analyzed for their effect on evectin function by using cell based assays. One such assay evaluates the effect of evectins, hybrids, and binding partners on the activation of mitogen activated kinase, RAS, or the phosphorylation of myelin basic protein. Other evectin characterization assays involve molecular biology techniques designed to identify protein-protein interactions (e.g., two-hybrid systems).

The diagnostic embodiments of the invention (including diagnostic kits) are designed to identify defects in vesicle trafficking, signal transduction, G protein binding, and membrane biosynthesis and organization in organisms (e.g., plants, yeast, mold, insects, animals, mammals, and humans). Nucleic acid and protein based diagnostics are provided. Some of these diagnostics identify defects in vesicle trafficking, signal transduction, G protein binding, and membrane biosynthesis and organization in organisms by detecting a polymorphism in an evectin. Other diagnostic approaches are concerned with the detection of aberrant amounts or levels of expression of evectins in specific tissues. Further, some diagnostic approaches entail the detection of skewed ratios of expression of a plurality of evectins. The polymorphisms, levels of expression of an evectin, and evectin ratios can be recorded in a database, which can be accessed to identify the disease state of a tested organism.

The pharmaceutical embodiments of the invention include medicaments having evectins, evectin-like hybrids, and binding partners that interact with evectins. These medicaments can be prepared in accordance with conventional methods of galenic pharmacy for administration to organisms in need of treatment. A therapeutically effective amount of an evectin molecule, evectin-like hybrid molecule, or a binding partner of evectin can be incorporated into a pharmaceutical composition with or without a carrier. Routes of administration of the pharmaceuticals of the invention include, but are not limited to, topical, transdermal, parenteral, gastrointestinal, transbronchial, and transalveolar. These pharmaceuticals can be provided to organisms in need of treatment for retinal diseases, neuropathies, maladies associated with abberrant signal transduction, and vessicle trafficking. The section below describes several of the nucleic acid embodiments of the invention.

Nucleic Acids Encoding Evectins and Evectin-like Hybrids

A new family of structurally distinctive molecules, designated evectins, are embodiments of the invention. These molecules can be identified by their four domains: a pleckstrin homology domain (PHD), a protein-protein module, a phosphorylation domain, and a hydrophobic domain. The nucleic acid embodiments of the invention include nucleotides encoding evectin molecules and fragments thereof and variants such as spliced variants, allelic variants, synonomous sequences, and homologous or orthologous molecules. Some embodiments for example, include genomic DNA, RNA, and cDNA encoding evectins. Evectins can be present in many different organisms including but not limited to plants, insects, animals, and mammals. Further, molecules that resemble evectins by the organization of their structure (e.g., a molecule having a PHD, a protein-protein module, a phosphorylation domain, and a hydrophobic or membrane associated domain) and hybrid molecules having one or more of the aforementioned domains are embodiments of the invention.

The discovery of evt-1 and evt-2 was made while performing a yeast two-hybrid screen. Partial-length cDNAs encoding rat evt-1 were isolated in a yeast two-hybrid screen and the full-length evt-1 cDNA (1875 bp) was obtained from a λ Zap Schwann cell cDNA library using the two-hybrid cDNA fragments as probes. (See Example 1). The coding sequence of rat evt-1 cDNA and evt-1 protein are provided in the Sequence Listing (SEQ. ID. NOS. 1 and 6), respectively. The full-length cDNA for rat evt-1 is also provided in the Sequence Listing (SEQ. ID. NO. 11). The deduced amino acid sequence of rat evt-1 did not exhibit substantial sequence similarity to any known protein. A BLAST search using evt-1 did yield a variety of human and mouse partial ESTs that correspond to evt-1, however. The coding sequence of murine evt-1 cDNA and evt-1 protein are provided in the Sequence Listing (SEQ. ID. NOS. 2 and 7), respectively. In addition, the coding sequence of human evt-1 cDNA and evt-1 protein are provided in the Sequence Listing (SEQ. ID. NOS. 3 and 8), respectively.

The BLAST using rat evt-1 also revealed another evectin family member, designated evt-2. (FIG. 1). The coding sequence of murine evt-2 cDNA and evt-2 protein are provided in the Sequence Listing (SEQ. ID. NOS. 4 and 9), respectively. The full-length cDNA for murine evt-2 is also provided in the Sequence Listing (SEQ. ID. NO. 12). Additionally, the coding sequence of human evt-2 cDNA and protein are provided in the Sequence Listing (SEQ. ID. NOS. 5 and 10), respectively. Evt-1 and evt-2 display approximately 40% amino acid identity overall, however, conservation is appreciably higher in specific sub-regions of the gene.

Data presented in the working examples, infra, demonstrate that: human evt-1 maps to an interval within chromosome 11q13 at 80–84cM from the centromere, between markers D11S916 and D11S911 (Example 2). In addition, evt-1 is expressed in photoreceptors, pigment epithelium, pinealcytes, oligodendrocytes, and ependymal cells, whereas, evt-2 expression is detected in neurons, hippocampal fields and overlying cortex, and the neocortex but not the epenndyma or white matter tracts (Examples 3 and 4). We found that evt-1 has an approximately 25 kD molecular weight and exists in a modified and unmodified form (Example 5) and can associate with membranes (Examples 6 and 7). Also, an evt-1 knockout mouse was found to exhibit a phenotype characterized by a loss of the buffer zone between axons (Example 9).

The evectin nucleotide sequences of the invention also include: (a) the DNA sequences shown in the sequence listing (SEQ. ID. NOS. 1–5, 11, and 12); (b) nucleotide sequences encoding the amino acid sequences shown in the sequence listing (SEQ. ID. NOS. 6–10); (c) any nucleotide sequence that hybridizes to the complement of the DNA sequences shown in the sequence listing (SEQ. ID. NOS. 1–5, 11, and 12) under stringent conditions, e.g., hybridization to filter-bound DNA in 0.5 M $NaHPO_4$, 7.0% sodium dodecyl sulfate (SDS), 1 mM EDTA at 50° C. and washing in 0.2×SSC/0.2% SDS at 50° C.; and (d) any nucleotide sequence that hybridizes to the complement of the DNA sequences that encode an amino acid sequence provided in the sequence listing (SEQ. ID. NOS. 6–10) under less stringent conditions (e.g., hybridization in 0.5 M $NaHPO_4$, 7.0% sodium dodecyl sulfate (SDS), 1 mM EDTA at 37° C. and washing in 0.2×SSC/0.2% SDS at 37° C.

Embodiments of the invention also include evectins that are isolated from other organisms (e.g., plants, molds, yeast, insects, animals, and mammals) and mutant evectins, whether naturally occurring or engineered. The presence of evectins in amphibians was verified by the experiments described in Example 6. Approaches to isolate evectin homologs in other species are provided infra. Embodiments of the invention also include fragments, modifications, derivatives, and variants of the sequences described above. Desired embodiments, for example, include nucleic acids having at least 9 consecutive bases of an evectin or a sequence complementary thereto and preferred fragments of the invention include at least 9 consecutive bases of evt-1 or evt-2 or a sequence complementary thereto. In this regard, the nucleic acid embodiments of the invention can have from 9 to approximately 1875 consecutive nucleotides. Some DNA fragments of the invention, for example, include nucleic acids having less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, 1300, 1400, 1500, 1600, 1700, 1800, and 1875 consecutive nucleotides of a sequence of SEQ. ID. NOS. 1–5, 11, and 12 or a complement thereof. Preferably, the nucleic acid embodiments, however, comprise at least 12, 13, 14, 15, 16, 17, 18, or 19 consecutive nucleotides of a sequence of SEQ. ID. NOS. 1–5, 11, and 12 or complement thereof. More preferably, the nucleic acid embodiments comprise at least 20–30 consecutive nucleotides of a sequence of SEQ. ID. NOS. 1–5, 11, and 12 or complement thereof.

The nucleic acid embodiments of this invention can also be altered by mutation such as substitutions, additions, or deletions that provide for sequences encoding functionally equivalent molecules. Due to the degeneracy of nucleotide coding sequences, other DNA sequences that encode substantially the same evectin amino acid sequence as depicted in SEQ. ID. NOS.: 6–10 can be used in some embodiments of the present invention. These include, but are not limited to, nucleic acid sequences comprising all or portions of evt-1 or evt-2 or nucleic acids that complement all or part of evt-1 or evt-2 that have been altered by the substitution of different codons that encode a functionally equivalent amino acid residue within the sequence, thus producing a silent change, or a functionally non-equivalent amino acid residue within the sequence, thus producing a detectable change.

The mutant evectin nucleic acids of the invention also include nucleic acids encoding evectin polypeptides or peptides having a non-conservative change that effects the functionality of the molecule (e.g. modulates vesicle trafficking, signal transduction, G protein binding, or membrane attachment). Additional mutant evectins include nucleic acids encoding molecules in which one or more of the evectin domains are deleted, e.g., an evectin lacking the transmembrane domain or the phosphorylation domain, or the protein-protein module, or the PHD, or any combination thereof. Further, some evectin mutant nucleic acids of the invention encode one or more evectin domains combined in a novel fashion so as to create an "evectin-like hybrid" molecule, also referred to as a "hybrid". For the purposes of this disclosure, the four domains of an evectin can be thought of as cassettes that can be interchangeably joined so as to create the evectin-like hybrids. These hybrids can be used to modulate (i.e., inhibit or enhance) vesicle trafficking, signal transduction, G protein binding, or membrane biosynthesis and organization, for example. Some nucleic acids of the invention also encode multimerized evectins or hybrids, which are characterized by a structure having at least two of the same domain (e.g., a hybrid having two PHD domains joined to a protein-protein module, a phosphorylation domain and a transmembrane domain). Several assays can be employed to evaluate these molecules for their ability to modulate vesicle trafficking, signal transduction, G protein binding, or membrane biosynthesis and organization and many are discussed in detail infra. The evectin-like hybrids that are identified for their ability to modulate vesicle trafficking, signal transduction, G protein binding, or membrane biosynthesis and organization can be used in biotechnological assays and can be formulated in pharmaceuticals for the treatment of diseases and abnormalities in various organisms.

Some mutant evectin nucleic acid embodiments of the invention include nucleic acids encoding evectin-like hybrids, wherein one or more of the domains are swapped with synthetic polypeptides. For example, nucleic acids encoding the evt-1 PHD, protein-protein module, and phosphorylation domain can be joined to a nucleic acid encoding a synthetic hydrophobic domain (e.g., poly-leucine) so as to create a reagent that better associates with a membrane. Similarly, the nucleic acids encoding the various domains of evt-1 or evt-2 can be swapped with nucleic acids encoding PHD, protein-protein modules, phosphorylation domains, and hydrophobic domains from other proteins (besides evectins) involved in signal transduction. In this manner, many different nucleic acids encoding designer peptides can be created and these molecules can be used to modulate specific G-protein-coupled signal transduction pathways, for example.

The nucleic acid sequences described above also have biotechnological and diagnostic use, e.g., in nucleic acid hybridization assays, Southern and Northern Blot analysis, etc. and the prognosis of diseases associated with aberrant vesicle trafficking, signal transduction, G protein binding, or membrane biosynthesis and organization (e.g., adFEVR or multiple sclerosis).

By using the evectin nucleic acid sequences disclosed in the sequence listing (SEQ. ID. NOS. 1–5, 11, and 12), probes that complement evt-1 or evt-2 can be designed and manufactured by oligonucleotide synthesis. Desirable probes comprise a nucleic acid sequence of (SEQ. ID. NOS.: 1–5) that is unique to evectins with preferred probes comprising a nucleic acid fragment of (SEQ. ID. NOS.: 1–5) that is unique to evt-1 or evt-2. These probes can be used to screen cDNA or genomic libraries from various organisms (e.g., plants, molds, fungi, yeast, insects, animals, and mammals) so as to isolate natural sources of the nucleic acid embodiments of the invention. Screening can be by filter hybridization, for example, using duplicate filters. The labeled probe preferably contains at least 15–30 base pairs of a nucleic acid sequence of (SEQ. ID. NOS.: 1–5) that are unique to evt-1 or evt-2. The hybridization washing conditions used are preferably of a lower stringency when the cDNA library is derived from an organism different from the type of organism from which the labeled sequence is originated.

With respect to the cloning of an evt-1 or evt-2 homolog, using murine evt-1 or evt-2 probes, for example, hybridization can be performed in 0.5M $NaHPO_4$, 7.0% sodium dodecyl sulfate (SDS), 1 mM EDTA at 37° C. overnight and washing can be performed in 0.2×SSC/0.2% SDS at 37° C. Low stringency conditions are well known to those of skill in the art, and will vary predictably depending on the specific organisms from which the library and the labeled sequences are derived. For guidance regarding such conditions see, for example, Sambrook et al., 1989, *Molecular Cloning. A Laboratory Manual*, Cold Springs Harbor Press, N.Y.; and Ausubel et al., 1989, *Current Protocols in Molecular Biology*, Green Publishing Associates and Wiley Interscience, N.Y.

Further, sequences from nucleic acids complementing evt-1 or evt-2, or portions thereof, can be used to make oligonucleotide primers by conventional oligonucleotide synthesis for use in isolation and diagnostic procedures that employ the Polymerase Chain Reaction (PCR) or other enzyme-mediated nucleic acid amplification techniques. An evectin gene homolog can be isolated from a nucleic acid of the organism of interest by performing PCR using two degenerate oligonucleotide primer pools designed on the basis of amino acid sequences within the evectin gene products disclosed herein. The template for the reaction can be cDNA obtained by reverse transcription of mRNA prepared from, for example, cells or tissue of an organism known or believed to express an evectin. A variety of PCR techniques are familiar to those skilled in the art. For a review of PCR technology, see Molecular Cloning to Genetic Engineering White, B. A. Ed. in *Methods in Molecular Biology* 67: Humana Press, Totowa (1997), the disclosure of which is incorporated herein by reference in its entirety and the publication entitled "PCR Methods and Applications" (1991, Cold Spring Harbor Laboratory Press), the disclosure of which is incorporated herein by reference in its entirety.

For amplification of mRNAs, it is within the scope of the invention to reverse transcribe mRNA into cDNA followed by PCR (RT-PCR); or, to use a single enzyme for both steps as described in U.S. Pat. No. 5,322,770, the disclosure of which is incorporated herein by reference in its entirety. Another technique involves the use of Reverse Transcriptase Asymmetric Gap Ligase Chain Reaction (RT-AGLCR), as described by Marshall R. L. et al. (*PCR Methods and Applications* 4:80–84, 1994), the disclosure of which is incorporated herein by reference in its entirety. Briefly, RNA is isolated, following standard procedures, from an appropriate cellular or tissue source. A reverse transcription reaction is performed on the RNA using an oligonucleotide primer specific for the most 5' end of the amplified fragment as a primer of first strand synthesis. The resulting RNA/DNA hybrid is then "tailed" with guanines using a standard terminal transferase reaction. The hybrid is then digested with RNAse H, and second strand synthesis is primed with a poly-C primer. Thus, cDNA sequences upstream of the amplified fragment are easily isolated. For a review of cloning strategies which can be used, see e.g., Sambrook et al., 1989, supra.

In each of these amplification procedures, primers on either side of the sequence to be amplified are added to a suitably prepared nucleic acid sample along with dNTPs and a thermostable polymerase, such as Taq polymerase, Pfu polymerase, or Vent polymerase. The nucleic acid in the sample is denatured and the primers are specifically hybridized to complementary nucleic acid sequences in the sample. The hybridized primers are then extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188, the disclosure of which is incorporated herein by reference in their entirety.

The primers are selected to be substantially complementary to a portion of the nucleic acid sequence of (SEQ. ID. NOS. 1–5, 11, and 12) that is unique to evt-1 or evt-2, thereby allowing the sequences between the primers to be amplified. Preferably, primers are 16, 17, 18, 19, 20, 21, 22, 23, 24, 25, 26, 27, 28, 29 and 30 nucleotides in length. The formation of stable hybrids depends on the melting temperature (Tm) of the DNA. The Tm depends on the length of the primer, the ionic strength of the solution and the G+C content. The higher the G+C content of the primer, the higher is the melting temperature because G:C pairs are held by three H bonds whereas A:T pairs have only two. The G+C content of the amplification primers of the present invention preferably ranges between 10 and 75%, more preferably between 35 and 60%, and most preferably between 40 and 55%. The appropriate length for primers under a particular set of assay conditions can be empirically determined by one of skill in the art.

The spacing of the primers relates to the length of the segment to be amplified. In the context of the present invention, amplified segments carrying nucleic acid sequence encoding fragments of evt-1 or evt-2 can range in size from at least about 25 bp to 35 kb. Amplification fragments from 25–1000 bp are typical, fragments from 50–1000 bp are preferred and fragments from 100–600 bp are highly preferred. It will be appreciated that amplification primers can be of any sequence that allows for specific amplification of a region of an evectin and can, for example, include modifications such as restriction sites to facilitate cloning.

The PCR product can be subcloned and sequenced to ensure that the amplified sequences represent the sequences of an evectin gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library. The identification and characterization of genomic clones from many different organisms (particularly humans) is helpful for designing diagnostic tests and clinical protocols for treating and preventing aberrations or diseases involving defects in vesicle trafficking, signal transduction, G protein binding, or membrane biosynthesis and organization. For example, sequences derived from regions adjacent to the intron/exon boundaries of human evectin genes can be used to design primers for use in amplification assays to detect mutations within the exons, introns, splice sites (e.g. splice acceptor and/or donor sites), etc., that can be used in diagnostics.

The evectin gene sequences can additionally be used to isolate mutant evectin gene alleles. Such mutant alleles can be isolated from organisms either known or proposed to have a genotype that contributes to a disorder involving aberrant vesicle trafficking, signal transduction, G protein binding, or membrane biosynthesis and organization. Mutant alleles and mutant allele products can then be utilized in the therapeutic and diagnostic systems described below. Additionally, such evectin gene sequences can be used to detect evectin gene regulatory (e.g., promoter or promotor/enhancer) defects that can affect vesicle trafficking, signal transduction, G protein binding, or membrane biosynthesis and organization.

A cDNA of a mutant evectin gene can be isolated, for example, by using PCR. In this case, the first cDNA strand can be synthesized by hybridizing an oligo-dT oligonucleotide to mRNA isolated from tissue known or suspected to be expressed in an individual putatively carrying the mutant evectin allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and organismed to DNA sequence analysis through methods well known to those of skill in the art. By comparing the DNA sequence of the mutant evectin allele to that of the normal evectin allele, the mutation(s) responsible for the loss or alteration of function of the mutant evectin gene product can be ascertained.

Alternatively, a genomic library can be constructed using DNA obtained from an organism suspected of or known to carry the mutant evectin allele, or a cDNA library can be constructed using RNA from a tissue known, or suspected, to express the mutant evectin allele. The normal evectin gene or any suitable fragment thereof can then be labeled and used as a probe to identify the corresponding mutant evectin allele in such libraries. Clones containing the mutant evectin gene sequences can then be purified and subjected to sequence analysis according to methods well known to those of skill in the art.

Additionally, an expression library can be constructed utilizing cDNA synthesized from, for example, RNA isolated from a tissue known, or suspected, to express a mutant evectin allele in an organism suspected of, or known to carry, such a mutant allele. In this manner, gene products made by the putatively mutant tissue can be expressed and screened using standard antibody screening techniques in conjunction with antibodies raised against the normal evectin gene product. (For screening techniques, see, for example, Harlow, E. and Lane, eds., 1988, *Antibodies: A Laboratory Manual*, Cold Spring Harbor Press, Cold Spring Harbor.) For instance, the anti-evt-1 antibody described in Example 5 was found to cross-react with amphibian evt-1. By using conventional antibody screening techniques and the anti-evt-1 antibody described in Example 5, one can isolate evt-1 from expression libraries of various organisms. In cases where an evectin mutation results in an expressed gene product with altered function (e.g., as a result of a missense or a frameshift mutation), a polyclonal set of antibodies against evectin are likely to cross-react with the mutant evectin gene product. Library clones detected via their reaction with such labeled antibodies can be purified and subjected to sequence analysis according to methods well known to those of skill in the art.

The invention also encompasses (a) DNA vectors that contain any of the foregoing evectin coding sequences and/or their complements (i.e., antisense); (b) DNA expression vectors that contain any of the foregoing evectin coding sequences operatively associated with a regulatory element that directs the expression of the coding sequences; and (c) genetically engineered host cells that contain any of the foregoing evectin coding sequences operatively associated with a regulatory element that directs the expression of the coding sequences in the host cell. These recombinant constructs are capable of replicating autonomously in a host cell. Alternatively, the recombinant constructs can become integrated into the chromosomal DNA of a host cell. Such recombinant polynucleotides typically comprise an evectin genomic or cDNA polynucleotide of semi-synthetic or synthetic origin by virtue of human manipulation. Therefore, recombinant nucleic acids comprising evectin sequences and complements thereof that are not naturally occurring are provided by embodiments of this invention.

Although nucleic acids encoding an evectin or nucleic acids having sequences that complement an evectin gene as they appear in nature can be employed, they will often be altered, e.g., by deletion, substitution, or insertion and can be accompanied by sequence not present in humans. As used herein, regulatory elements include, but are not limited to, inducible and non-inducible promoters, enhancers, operators and other elements known to those skilled in the art that drive and regulate expression. Such regulatory elements include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

In addition, recombinant evectin-encoding nucleic acid sequences and their complementary sequences can be engineered so as to modify processing or expression of the evectin. For example, and not by way of limitation, the evt-1 or evt-2 gene can be combined with a promoter sequence and/or ribosome binding site, or a signal sequence can be inserted upstream of evectin-encoding sequences to permit secretion of the evectin and thereby facilitate harvesting or bioavailability. Additionally, a given evt-1 or evt-2 nucleic acid can be mutated in vitro or in vivo, to create and/or destroy translation, initiation, and/or termination sequences, or to create variations in coding regions and/or form new restriction sites or destroy preexisting ones, or to facilitate further in vitro modification. Any technique for mutagenesis known in the art can be used, including but not limited to, in vitro site-directed mutagenesis. (Hutchinson et al., *J. Biol. Chem.*, 253:6551 (1978), herein incorporated by reference).

Further, nucleic acids encoding other proteins or domains of other proteins can be joined to nucleic acids encoding an evectin so as to create a fusion protein. Nucleotides encoding fusion proteins can include, but are not limited to, a full length evectin, a truncated evectin or a peptide fragment of an evectin fused to an unrelated protein or peptide, such as for example, a transmembrane sequence, which better anchors the evectin peptide fragment to the cell membrane; an Ig Fc domain which increases the stability and half life of the resulting fusion protein (e.g., evt-Ig); or an enzyme, fluorescent protein, luminescent protein which can be used as a marker (e.g., an evectin-Green Fluorescent Protein ("evt-GFP") fusion protein). The fusion proteins are useful as biotechnological tools or pharmaceuticals or both, as will be discussed infra. The section below describes several of the polypeptides of the invention and methods of making these molecules.

Evectin Polypeptides

Figure 3:
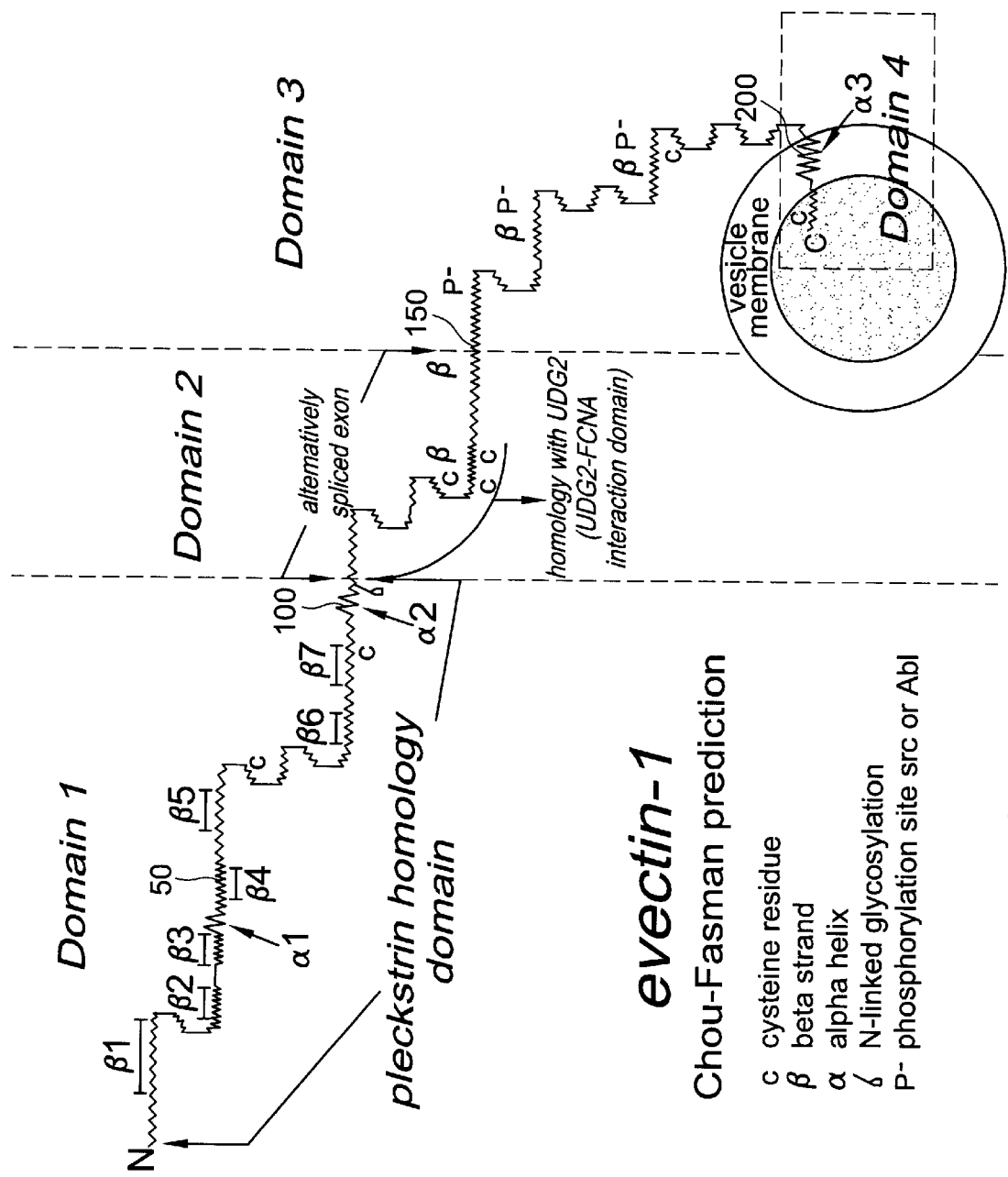
FIG. 3 is an illustration of the predicted secondary structure for rat evt-1 as generated by the PEPPLOT and PLOTSTRUCTURE programs of the University of Wisconsin Genetics Computer Group.

Evectins, evectin polypeptides, fragments of these molecules, and chemicals that resemble these molecules including, but not limited to peptidomimetics, modified evectins, and derivatives or variants of evectins are embodiments of the invention. Evectin polypeptides can be present either naturally or through genetic engineering in a number of organisms (e.g., plants, insects, amphibians, reptiles, birds, other animals, cats, dogs, rodents, primates, humans, and other mammals). The evectin family members have a novel structure that can be readily sub-divided into four domains. FIG. 3 illustrates the seven beta strands (β1–β7), the C-terminal alpha helix of the evt-1 PHD (α2), helix α1 (conserved in some but not all pleckstrin homology domains or "PHDs"), and helix α3 (a hydrophobic region predicted to span a membrane bilayer). The position of these elements was based on alignment of the evt-1 PHD with X-ray crystal or NMR structures of known PHDs and the predicted evt-1 secondary structure.

Neither evt-1 or evt-2 has a cleaved, N-terminal signal peptide that would allow for insertion into membranes via a conventional ER-to-Golgi routing. Instead, both proteins immediately begin with an approximately 110 amino acid region that exhibits distinctive structural features which were first recognized in pleckstrin but now been identified in a wide variety of proteins. (See Lemmon and Ferguson, *Curr. Top. Microbiol Immunol.*, 228:39–74 (1998) for a discussion of PHDs). The PHDs of evt-1 and evt-2 are not closely related to any previously identified PHD (FIG. 2). Nevertheless, the PHDs of evt-1 and evt-2 are predicted to fold into the 7 β strand sandwich, closed C-terminally by a conserved α helix, which is characteristic of all known PHD three-dimensional structures.

Evt-1 and evt-2 also have all of the critically conserved amino acid motifs that are diagnostic of PHDs and exhibit the correct predicted spacing of the conserved features of PHD secondary structure (FIG. 2). Structurally, the evt-1 and evt-2 PHDs resemble: (a) the kinase Akt, which regulates the apoptotic death pathway; (b) the oxysterol binding protein (OSBP), which translocates to the Golgi apparatus upon binding oxygenated derivatives of cholesterol; (c) the GTPase dynamin, an essential regulator of vesicular trafficking during clathrin-mediated endocytosis; and (d) ARNO, a guanine nucleotide exchange factor for the ARF family of G-proteins. (See the following articles for a discussion of Akt kinase, OSBP, dynamin, and ARNO: Dudek et al., *Science*, 275:661–665 (1997); (Levine and Munro, *Curr. Biol.*, 8:729–739 (1998); (Schmid et al., *Curr. Opin. Cell Biol.*, 10:504–512 (1998); and (Boman and Kahn, *Trends Biochem. Sci.*, 20:147–150 (1995)). In contrast to these molecules, however, evt-1 PHD does not bind PIP2 with high affinity.

Downstream of the PHD, the evectins contain a 35-residue alternatively-spliced domain (Domain 2 in FIG. 3). In evt-1, this domain is similar to the DNA editing enzyme uracil-DNA glycoylase 2 (UDG2). The amino acids that are identical between evt-1 and UDG2 are the same residues that are critical for binding of UDG2 to PCNA. (See Muller-Weeks and Caradonna, *Exp. Cell Res.*, 226:346–355 (1996) for a discussion of UDG2). Domain 2 is referred to herein as a "protein-protein interaction" module. Downstream of Domain 2 are a set of predicted β strands that have sites suitable for phosphorylation by members of the src or Abl family of kinases (Domain 3 in FIG. 3). This domain displays no significant similarity to any known protein and is referred to as the "phosphorylation domain".

The extreme C-termini of the evectins (Domain 4, helix α3 in FIG. 2) are highly-conserved hydrophobic α helices that are predicted to span a lipid bilayer (FIGS. 1 and 2). Such C-terminal helices are a general feature of small, membrane-associated proteins that lack cleaved N-terminal signal peptides and allow these proteins to be post-translationally inserted into membranes.

With reference to FIG. 4A, a typical evectin family member is characterized by a structure having a PHD (1), a protein-protein interaction module (2), a phosphorylation domain (3), and a hydrophobic domain (4). Thus, the term "evectin" refers to a family of proteins and the nucleic acids encoding these proteins including, but not limited to evt-1 and evt-2, which are characterized by the structure described above.

The nucleic acids encoding an evectin or fragments thereof, described in the previous section, can be manipulated using conventional techniques in molecular biology so as to create recombinant constructs that express evectin protein or fragments of evectin protein. The evectin polypeptides or derivatives thereof, include but are not limited to, those containing as a primary amino acid sequence all of the amino acid sequence substantially as depicted in the Sequence Listing (SEQ. ID. NOS.: 6–10) and fragments of SEQ. ID. NOS.: 6–10 at least three amino acids in length including altered sequences in which functionally equivalent amino acid residues are substituted for residues within the sequence resulting in a silent change. Preferred fragments of a sequence of SEQ. ID. NOS.: 6–10 are at least three amino acids and comprise amino acid sequence unique to evectins including altered sequences in which functionally equivalent amino acid residues are substituted for residues within the sequence resulting in a silent change. The evectin peptide fragments of the invention can be, for example, less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, and 1094 amino acids in length.

Embodiments of the invention encompass proteins that are functionally equivalent to the evectins encoded by the nucleotide sequences described in SEQ. ID. NOS. 6–10, as judged by any of a number of criteria, including but not limited to the ability to bind G-proteins and a lipid membrane, the binding affinity for a particular G-protein and/or a lipid membrane, the resulting biological effect of evectin interaction, e.g., signal transduction, a change in cellular metabolism (e.g., ion flux, tyrosine phosphorylation) or change in phenotype in an appropriate cell type (such as the amelioration, prevention or delay of myelination, vesicle trafficking, or membrane biosynthesis and organization). Such functionally equivalent evectins include, but are not limited to, additions or substitutions of amino acid residues within the amino acid sequence encoded by the evectin nucleotide sequences described above but, which result in a silent change, thus producing a functionally equivalent gene product. For example, embodiments include evectins that have one or more amino acid residues within the evectin polypeptide of SEQ. ID. NOS.: 6–10 and fragments of SEQ. ID. NOS.: 6–10 that are substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

Additional embodiments include mutant evectins (e.g., evt-1 and evt-2), wherein one or more amino acid residues within the evectin polypeptide of SEQ. ID. NOS.: 6–10 and fragments of SEQ. ID. NOS.: 6–10 are substituted by another amino acid resulting in a non-conservative change. While random mutations can be made to evt-1 or evt-2 DNA (using random mutagenesis techniques well known to those skilled in the art) and the resulting mutant evectins tested for activity, site-directed mutations of the evt-1 or evt-2 coding sequence can be engineered (using site-directed mutagenesis techniques well known to those skilled in the art) to generate mutant evectins with increased function, e.g., higher binding affinity for a specific G-protein or membrane, and/or greater signaling capacity, vesicle trafficking, or membrane biosynthesis and organization; or decreased function, e.g., lower binding affinity for a particular G-protein or membrane, and/or decreased signal transduction capacity, vesicle trafficking, or membrane biosynthesis and organization.

For example, a comparison of the evectin pleckstrin homology domains (PHD) to the most closely related PHDs in public databases is shown in FIG. 2 and the amino acid identities with rat evt-1 are indicated in black and the conservative substitutions are indicated in gray. Mutant evectins can be engineered so that regions of amino acid identity and conservation (indicated in black and gray in FIG. 2) are maintained, whereas the variable residues are altered, e.g., by deletion or insertion of an amino acid residue(s) or by substitution of one or more different amino acid residues. Non-conservative changes can be engineered at these variable positions to alter function, e.g., G-protein binding affinity or signal transduction capability, or both. Alternatively, where alteration of function is desired, deletion or non-conservative alterations of the conserved regions (indicated in black and gray in FIG. 2) can be engineered. For example, deletion or non-conservative alterations (substitutions or insertions) of amino acid residues in the PHD can be engineered to produce a mutant evectin that binds a G-protein but prevents G-protein-mediated signaling. The same mutation strategy can also be used to design mutant evectins based on the alignments of the remaining three domains. Desirably, evectins with greater hydrophobicity and affinity for membranes can be created by enhancing the hydrophobic domain (e.g., increasing the amount of hydrophobic residues, replacing non-hydrophobic residues with hydrophobic residues, and swapping in a hydrophobic domain that consists of entirely hydrophobic residues, such as poly-leucine).

Figure 4:
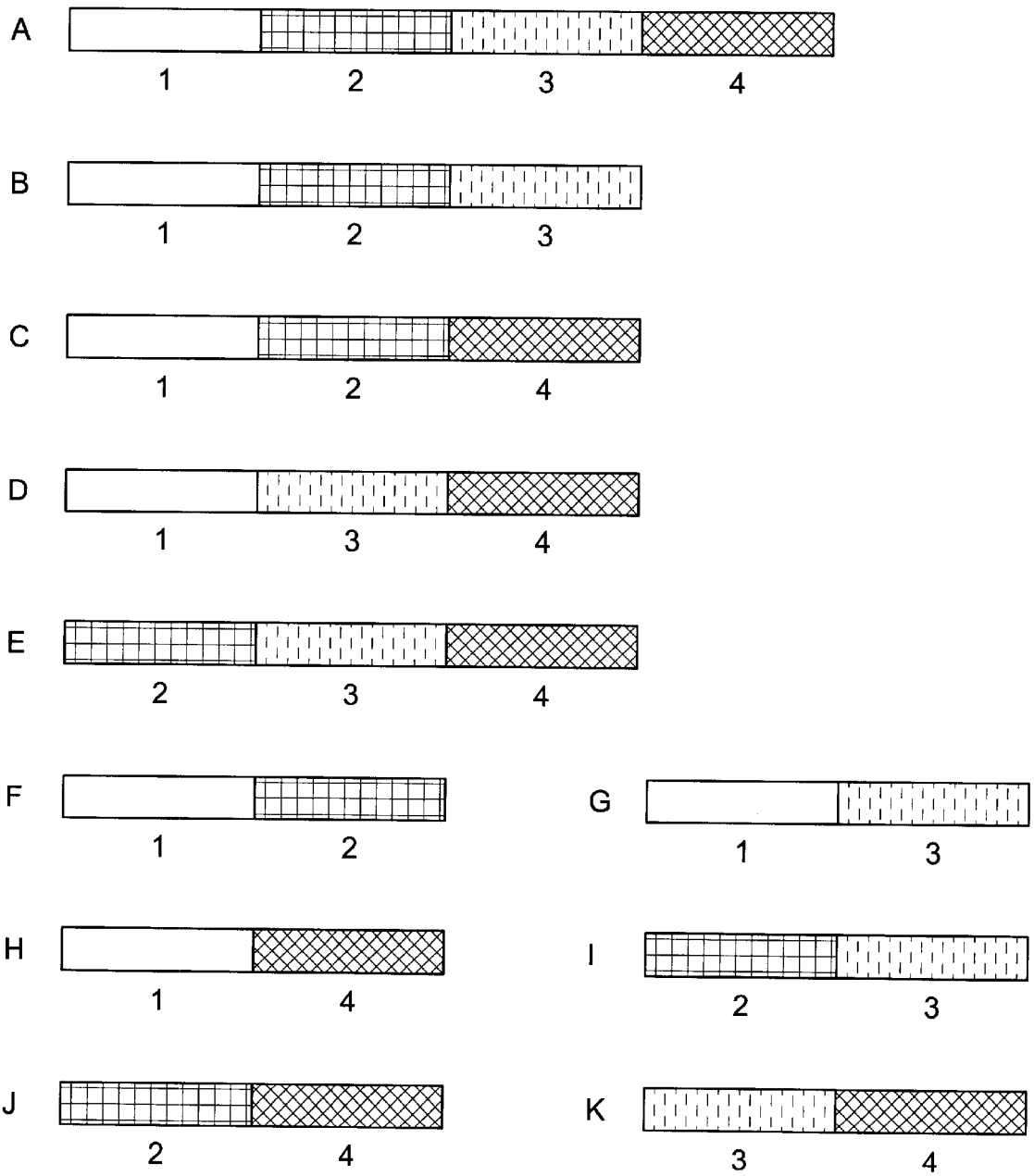
FIGS. 4(A–K) are block diagrams of several preferred molecules of the invention: (A) shows a typical evectin protein, wherein (1) designates a pleckstrin homology domain, (2) designates a protein-protein module, (3) designates a phosphorylation domain, and (4) designates a hydrophobic domain; (B–K) show various evectin-like hybrids, wherein one or more domains (i.e., pleckstrin homology domain (1), protein-protein module (2), phosphorylation domain (3) or the hydrophobic domain (4)) have been deleted and/or combined differently than the order of domains in (A) to create the hybrid shown.

FIGS. 4(B–K) show several more embodiments of the invention, referred to as "evectin-like hybrids" or "hybrids", which can be used as biotechnological tools and/or the active ingredients in pharmaceuticals that treat disorders involving aberrant vesicle trafficking, signal transduction, G protein binding, or membrane biosynthesis and organization. It is to be understood that each individual domain of a typical evectin molecule, as shown in FIG. 4A, can be thought of as a cassette, which can be deleted, joined interchangeably with one another, or multimerized. In this context, the term "multimerized" refers to hybrid molecules having more than one PHD or protein-protein module or phosphorylation domain or hydrophobic domain. FIG. 4B illustrates one example of a hybrid lacking a hydrophobic tail so as make a soluble form of evectin.

FIG. 4C, on the other hand, shows a membrane bindable hybrid lacking the phosphorylation domain. FIG. 4D shows a membrane bindable hybrid lacking the protein-protein module and FIG. 4E shows a membrane bindable hybrid lacking the PHD. FIGS. 4(F–K) show several other embodiments of the invention having the various domains of evectin molecules combined in novel fashions. FIG. 4F, for example, shows a molecule having a PHD joined to a protein-protein module, FIG. 4G shows a molecule having a PHD joined to a phosphorylation domain, FIG. 4H shows a molecule having a PHD joined to a hydrophobic domain, FIG. 4I shows a molecule having a protein-protein module joined to a phosphorylation domain, FIG. 4J shows a molecule having a protein-protein module joined to a hydrophobic domain, and FIG. 4K shows a molecule having a phosphorylation domain joined to a hydrophobic domain. Many more evectin-like hybrids are within the scope of the invention and these molecules can be characterized by the presence of a fragment of an evectin or the equivalent thereof, as described above, or a molecule that structurally organized like an evectin or hybrid (e.g., the molecules shown in FIGS. 4(A–K).

Other embodiments include polypeptides that have homology to an evectin and function as a membrane bound modulator of signal transduction, vesicle trafficking, or membrane biosynthesis and organization. The term "homology to evectin" is meant to include nucleic acid or protein sequence homology or three-dimensional homology. Several techniques exist to determine nucleic acid or protein sequence homology and/or three-dimensional homology of proteins. These methods are routinely employed to discover the extent of homology that one sequence, domain, or model has to a target sequence, domain, or model. Because the region of evectin (e.g., a region within a PHD or protein-protein module or both) that modulates signal transduction can be quite small (e.g., 3, 4, 5, 6, 7, 8, 9, 10, 12, 15, 18, 20, 22, 25, 30 amino acids in length), embodiments of the invention can exhibit a vast degree of homology to full-length evectin. For example, a fusion protein having a small region of evectin can exhibit a low degree of overall homology to evectin yet retain the ability to function as a modulator of signal transduction, vesicle trafficking, or membrane biosynthesis and organization equivalent to evectin. Thus, embodiments of the invention can have from 1% homology to 100% homology to full-length evectin. That is, embodiments can have 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, 21.0%, 22.0%, 23.0%, 24.0%, 25.0%, 26.0%, 27.0%, 28.0%, 29.0%, 30.0%, 31.0%, 32.0%, 33.0%, 34.0%, 35.0%, 36.0%, 37.0%, 38.0%, 39.0%, 40.0%, 41.0%, 42.0%, 43.0%, 44.0%, 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% homology to full-length evectin.

Therefore, embodiments of the invention include polypeptides varying in size from 3 amino acids up to and including the full-length evectin protein that have 1% –100% homology to evectin and exhibit the ability to function as a membrane-bound modulator of signal transduction. Several homology searching programs based on nucleic acid or amino acid sequence are known in the art and can be used to identify molecules that are homologous to evt-1 and/or evt-2. Some approaches to identify molecules homologous to evectins are provided infra.

The evectins and evectin-like hybrids can be prepared by chemical synthesis methods (such as solid phase peptide synthesis) using techniques known in the art such as those set forth by Merrifield et al., *J. Am. Chem. Soc.* 85:2149 (1964), Houghten et al., *Proc. Natl. Acad. Sci. USA*, 82:51:32 (1985), Stewart and Young (*Solid phase peptide synthesis*, Pierce Chem Co., Rockford, Ill. (1984), and Creighton, 1983, *Proteins: Structures and Molecular Principles*, W. H. Freeman & Co., N.Y. herein incorporated by reference. Such polypeptides can be synthesized with or without a methionine on the amino terminus. Chemically synthesized evectin and fragments of evectin can be oxidized using methods set forth in these references to form disulfide bridges. Evectins and fragments of evectin can be employed as biologically active or immunological substitutes for natural, purified evectin and fragments of evectin.

While the evectins and hybrids can be chemically synthesized, it can be more effective to produce these polypeptides by recombinant DNA technology using techniques well known in the art. Such methods can be used to construct expression vectors containing the evt-1 or evt-2 nucleotide sequences, for example, and appropriate transcriptional and translational control signals. These methods include, for example, in vitro recombinant DNA techniques, synthetic techniques, and in vivo genetic recombination. Alternatively, RNA capable of encoding an evectin nucleotide sequences can be chemically synthesized using, for example, synthesizers. See, for example, the techniques described in *Oligonucleotide Synthesis*, 1984, Gait, M. J. ed., IRL Press, Oxford, which is incorporated by reference herein in its entirety.

In several embodiments, evectins, fragments of evectins, and evectin-like hybrids are expressed in a cell line. For example, some cells are made to express the evectin polypeptide of SEQ. ID. NOS.: 6–10 or fragments of SEQ. ID. NOS.: 6–10. The sequences, constructs, vectors, clones, and other materials comprising the present invention can advantageously be in enriched or isolated form. As used herein, "enriched" means that the concentration of the material is at least about 2, 5, 10, 100, or 1000 times its natural concentration (for example), advantageously 0.01%, by weight, preferably at least about 0.1% by weight. Enriched preparations from about 0.5%, 1%, 5%, 10%, and 20% by weight are also contemplated. The term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. It is also advantageous that the sequences be in purified form. The term "purified" does not require absolute purity; rather, it is intended as a relative definition. Isolated proteins have been conventionally purified to electrophoretic homogeneity by Coomassie staining, for example. Purification of starting material or natural material to at least one order of magnitude, preferably two or three orders, and more preferably four or five orders of magnitude is expressly contemplated.

A variety of host-expression vector systems can be utilized to express the evectins of the invention. Where the evectin or hybrid is a soluble derivative (e.g., hybrids having a truncated or deleted hydrophobic domain) it can be recovered from the culture, i.e., from the host cell in cases where the peptide or polypeptide is not secreted, and from the culture media in cases where the peptide or polypeptide is secreted by the cells. However, the expression systems also encompass engineered host cells that express the evectin or functional equivalents in situ, i.e., anchored in the cell membrane. Purification or enrichment of the evectin from such expression systems can be accomplished using appropriate detergents and lipid micelles and methods well known to those skilled in the art. However, such engineered host cells themselves can be used in situations where it is important not only to retain the structural and functional characteristics of the evectin, but to assess biological activity, e.g., in drug screening assays.

The expression systems that can be used for purposes of the invention include, but are not limited to, microorganisms such as bacteria (e.g., E. coli or B. subtilis) transformed with recombinant bacteriophage DNA, plasmid DNA or cosmid DNA expression vectors containing evectin nucleotide sequences; yeast (e.g., Saccharomyces, Pichia) transformed with recombinant yeast expression vectors containing the evectin nucleotide sequences; insect cell systems infected with recombinant virus expression vectors (e.g., baculovirus) containing the evectin sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing evectin nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the evectin gene product being expressed. For example, when a large quantity of such a protein is to be produced, for the generation of pharmaceutical compositions of evectin protein or for raising antibodies to the evectin protein, for example, vectors which direct the expression of high levels of fusion protein products that are readily purified can be desirable. Such vectors include, but are not limited, to the E. coli expression vector pUR278 (Ruther et al., EMBO J., 2:1791 (1983), in which the evectin coding sequence can be ligated individually into the vector in frame with the lacZ coding region so that a fusion protein is produced; pIN vectors (Inouye & Inouye, Nucleic Acids Res., 13:3101–3109 (1985); Van Heeke & Schuster, J. Biol. Chem., 264:5503–5509 (1989)); and the like. pGEX vectors can also be used to express foreign polypeptides as fusion proteins with glutathione S-transferase (GST). In general, such fusion proteins are soluble and can be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The evectin gene coding sequence can be cloned individually into non-essential regions (for example the polyhedrin gene) of the virus and placed under control of an AcNPV promoter (for example the polyhedrin promoter). Successful insertion of evectin gene coding sequence will result in inactivation of the polyhedrin gene and production of non-occluded recombinant virus, (i.e., virus lacking the proteinaceous coat coded for by the polyhedrin gene). These recombinant viruses are then used to infect Spodoptera frugiperda cells in which the inserted gene is expressed. (E.g., see Smith et al., J. Virol. 46: 584 (1983); and Smith, U.S. Pat. No. 4,215,051).

In mammalian host cells, a number of viral-based expression systems can be utilized. In cases where an adenovirus is used as an expression vector, the evectin nucleotide sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the evectin gene product in infected hosts. (E.g., See Logan & Shenk, Proc. Natl. Acad. Sci. USA 81:3655–3659 (1984)). Specific initiation signals can also be required for efficient translation of inserted evectin nucleotide sequences. These signals include the ATG initiation codon and adjacent sequences. In cases where an entire evectin gene or cDNA, including its own initiation codon and adjacent sequences, is inserted into the appropriate expression vector, no additional translational control signals are needed.

However, in cases where only a portion of the evectin coding sequence is inserted, exogenous translational control signals, including, perhaps, the ATG initiation codon, should be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See Bittner et al., Methods in Enzymol., 153:516–544 (1987)).

In addition, a host cell strain can be chosen which modulates the expression of the inserted sequences, or modifies and processes the gene product in the specific fashion desired. Such modifications (e.g., glycosylation) and processing (e.g., cleavage) of protein products are important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, and WI38.

For long-term, high-yield production of recombinant proteins, stable expression is preferred. For example, cell lines that stably express the evectin sequences described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines which express the evectin gene product. Such engineered cell lines are particularly useful in screening and evaluation of compounds that affect the endogenous activity of the evectin gene product.

A number of selection systems can be used, including but not limited to the herpes simplex virus thymidine kinase (Wigler, et al., *Cell* 11:223 (1977), hypoxanthine-guanine phosphoribosyltransferase (Szybalska & Szybalski, *Proc. Natl. Acad. Sci. USA* 48:2026 (1962), and adenine phosphoribosyltransferase (Lowy, et al., *Cell* 22:817 (1980) genes can be employed in tk.sup.-, hgprt.sup.- or aprt.sup.-cells, respectively. Also, antimetabolite resistance can be used as the basis of selection for the following genes: dhfr, which confers resistance to methotrexate (Wigler, et al., *Proc. Natl. Acad. Sci. USA* 77:3567 (1980); O'Hare, et al., *Proc. Natl. Acad. Sci. USA* 78:1527 (1981); gpt, which confers resistance to mycophenolic acid (Mulligan & Berg, *Proc. Natl. Acad. Sci. USA* 78:2072 (1981); neo, which confers resistance to the aminoglycoside G-418 (Colberre-Garapin, et al., *J. Mol. Biol.* 150:1 (1981); and hygro, which confers resistance to hygromycin (Santerre, et al., *Gene* 30:147 (1984)).

Alternatively, any fusion protein can be readily purified by utilizing an antibody specific for the fusion protein being expressed. For example, a system described by Janknecht et al. allows for the ready purification of non-denatured fusion proteins expressed in human cell lines. (Janknecht, et al., *Proc. Natl. Acad. Sci. USA* 88: 8972–8976 (1991)). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers. Example 8 provides a more detailed description of methods to express the proteins encoded by the nucleic acids of the invention.

The evectin gene products can also be expressed in plants, insects, and animals so as to create a transgenic organism. (See Example 9). Plants and insects of almost any species can be made to express an evectin, fragments of evectin, or evectin-like hybrid. Desirable transgenic plant systems having an evectin, fragments of evectin, or evectin-like hybrid include Arabadopsis, maize, and chlamydomonas. Desirable insect systems an evectin, fragments of evectin, or evectin-like hybrid include, for example, D. melanogaster and C. elegans. Animals of any species, including, but not limited to, amphibians, reptiles, birds, mice, rats, rabbits, guinea pigs, pigs, micro-pigs, goats, dogs, cats, and non-human primates, e.g., baboons, monkeys, and chimpanzees can be used to generate evectin transgenic animals. Transgenic organisms of the invention desirably exhibit germline transfer of wild-type or mutant evectins, fragments of evectin, or evectin-like hybrids. Other transgenic organisms of the invention are engineered to express human evectins, fragments of evectins, or evectin-like hybrids. Still other transgenic organisms of the invention exhibit complete knockouts or point mutations of one or more existing evectin genes. For example, in one embodiment, a transgenic animal comprises a knockout of both evt-1 and evt-2 and in another embodiment, a transgenic animal comprises at least one point mutation in both evt-1 and evt-2.

Any technique known in the art is preferably used to introduce the evectin transgene into animals to produce the founder lines of transgenic animals or to knock out or replace existing evectin genes. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., *Proc. Natl. Acad. Sci., USA* 82:6148–6152 (1985); gene targeting in embryonic stem cells (Thompson et al., *Cell* 56:313–321 (1989); electroporation of embryos (Lo, *Mol Cell. Biol.* 3:1803–1814 (1983); and sperm-mediated gene transfer (Lavitrano et al., *Cell* 57:717–723 (1989); etc. For a review of such techniques, see Gordon, *Transgenic Animals, Intl. Rev. Cytol.* 115:171–229 (1989), which is incorporated by reference herein in its entirety.

The invention provides for transgenic animals that carry an evectin transgene in all their cells, as well as animals that carry the transgene in some, but not all their cells, i.e., mosaic animals. The transgene can be integrated as a single transgene or in concatamers, e.g., head-to-head tandems or head-to-tail tandems. The transgene can also be selectively introduced into and activated in a particular cell type by following, for example, the teaching of Lasko et al. (Lasko, M. et al., *Proc. Natl. Acad. Sci. USA* 89: 6232–6236 (1992)). The regulatory sequences required for such a cell-type specific activation will depend upon the particular cell type of interest, and will be apparent to those of skill in the art.

When it is desired that the evectin gene transgene be integrated into the chromosomal site of the endogenous evectin gene, gene targeting is preferred. Briefly, when such a technique is to be utilized, vectors containing some nucleotide sequences homologous to the endogenous evectin gene are designed for the purpose of integrating, via homologous recombination with chromosomal sequences, into and disrupting the function of the nucleotide sequence of the endogenous evectin gene. The transgene can also be selectively introduced into a particular cell type, thus inactivating the endogenous evectin gene in only that cell type, by following, for example, the teaching of Gu et al. (Gu, et al., *Science* 265: 103–106 (1994)). The regulatory sequences required for such a cell-type specific inactivation will depend upon the particular cell type of interest, and will be apparent to those of skill in the art.

Once transgenic animals have been generated, the expression of the recombinant evectin gene can be assayed utilizing standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and RT-PCR. Samples of evectin gene-expressing tissue can also be evaluated immunocytochemically using antibodies specific for the evectin transgene product. Example 9 describes an approach used to create an evt-1 knockout mouse and the observation that such mice exhibit a myelination defect characterized by a decreased buffer zone between axons.

In addition to the naturally occurring evectins or peptide-based hybrids, embodiments of the invention include derivative or modified molecules that produce a more desirable cellular response. For example, a derivative evectin can include a polypeptide that has been engineered to have one or more cystine residues incorporated into the protein so as to promote the formation of a more stable derivative through disulfide bond formation. (See e.g., U.S. Pat. No. 4,908, 773). In the past, investigators have employed computers and computer graphics programs to aid in assessing the appropriateness of potential cystine linkage sites. (Perry, L. J., & Wetzel, R., *Science,* 226:555–557 (1984); Pabo, C. O., et al., *Biochemistry,* 25:5987–5991 (1986); Bott, R., et al., European Patent Application Ser. No. 130,756; Perry, L. J., & Wetzel, R., *Biochemistry,* 25:733–739 (1986); Wetzel, R. B., European Patent Application Ser. No. 155,832). The introduction of a cystine residue in a polypeptide can be accomplished using conventional molecular biology techniques.

Additional evectin and hybrid derivatives include peptidomimetics that resemble a polypeptide of interest. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Synthetic compounds that mimic the conformation and desirable features of a particular peptide, e.g., an oligopeptide, once such peptide has been found, but that avoids the undesirable features, e.g., flexibility (loss of conformation) and bond breakdown are known as a "peptidomimetics". (See, e.g., Spatola, A. F. Chemistry and Biochemistry of Amino Acids. Peptides, and Proteins (Weistein, B, Ed.), Vol. 7, pp. 267–357, Marcel Dekker, New York (1983), which describes the use of the methylenethio bioisostere [$CH_2 S$] as an amide replacement in enkephalin analogues; and Szelke et al., In peptides: Structure and Function, Proceedings of the Eighth American Peptide Symposium, (Hruby and Rich, Eds.); pp. 579–582, Pierce Chemical Co., Rockford, Ill. (1983), which describes renin inhibitors having both the methyleneamino [$CH_2 NH$] and hydroxyethylene [$CHOHCH_2$] bioisosteres at the Leu-Val amide bond in the 6–13 octapeptide derived from angiotensinogen).

In general, the design and synthesis of a peptidomimetic involves starting with the amino acid sequence of the peptide and conformational data (e.g., geometry data, such as bond lengths and angles) of a desired peptide (e.g., the most probable simulated peptide). That data is then used to determine the geometries that should be designed into the peptidomimetic. Numerous methods and techniques are known in the art for performing this step, any of which could be used. (See, e.g., Farmer, P. S., *Drug Design,* (Ariens, E. J. ed.), Vol. 10, pp. 119–143 (Academic Press, New York, London, Toronto, Sydney and San Francisco) (1980); Farmer, et al., in TIPS, 9/82, pp. 362–365; Verber et al., in TINS, 9/85, pp. 392–396; Kaltenbronn et al., in *J. Med. Chem.* 33: 838–845 (1990); and Spatola, A. F., in *Chemistry and Biochemistry of Amino Acids. Peptides, and Proteins,* Vol. 7, pp. 267–357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of β-sheets and α-helices in Peptides," Tibech, Vol. 8, pp. 249–255 (1990). Additional teachings can be found in U.S. Pat. Nos. 5,288,707; 5,552, 534; 5,811,515; 5,817,626; 5,817,879; 5,821,231; and 5,874, 529. The section below describes antibodies of the invention and methods of making these molecules.

Anti-evectin Antibodies

Following synthesis or expression and isolation or purification of the evectin protein or a portion thereof, the isolated or purified protein can be used to generate antibodies and tools for identifying agents that interact with evectin and fragments of evectin. Depending on the context, the term "antibodies" can encompass polyclonal, monoclonal, chimeric, single chain, Fab fragments and fragments produced by a Fab expression library. Antibodies that recognize evectin and fragments of evectin have many uses including, but not limited to, biotechnological applications, therapeutic/prophylactic applications, and diagnostic applications.

For the production of antibodies, various hosts including goats, rabbits, rats, mice, etc. can be immunized by injection with evectin or any portion, fragment or oligopeptide that retains immunogenic properties. Depending on the host species, various adjuvants can be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and Corynebacterium parvum are also potentially useful adjuvants.

Peptides used to induce specific antibodies can have an amino acid sequence consisting of at least three amino acids, and preferably at least 10 to 15 amino acids. Preferably, short stretches of amino acids encoding fragments of evectin are fused with those of another protein such as keyhole limpet hemocyanin such that an antibody is produced against the chimeric molecule. While antibodies capable of specifically recognizing evectin can be generated by injecting synthetic 3-mer, 10-mer, and 15-mer peptides that correspond to a protein sequence of evectin into mice, a more diverse set of antibodies can be generated by using recombinant evectin, purified evectin, or fragments of evectin.

To generate antibodies to evectin and fragments of evectin, substantially pure evectin or a fragment of evectin is isolated from a transfected or transformed cell. The concentration of the polypeptide in the final preparation is adjusted, for example, by concentration on an Amicon filter device, to the level of a few micrograms/ml. Monoclonal or polyclonal antibody to the polypeptide of interest can then be prepared as follows:

Monoclonal antibodies to evectin or a fragment of evectin can be prepared using any technique that provides for the production of antibody molecules by continuous cell lines in culture. These include, but are not limited to, the hybridoma technique originally described by Koehler and Milstein (*Nature* 256:495–497 (1975), the human B-cell hybridoma technique (Kosbor et al. *Immunol Today* 4:72 (1983); Cote et al *Proc Natl Acad Sci* 80:2026–2030 (1983), and the EBV-hybridoma technique Cole et al. *Monoclonal Antibodies and Cancer Therapy,* Alan R. Liss Inc, New York N.Y., pp 77–96 (1985). In addition, techniques developed for the production of "chimeric antibodies", the splicing of mouse antibody genes to human antibody genes to obtain a molecule with appropriate antigen specificity and biological activity can be used. (Morrison et al. *Proc Natl Acad Sci* 81:6851–6855 (1984); Neuberger et al. Nature 312:604–608 (1984); Takeda et al. *Nature* 314:452–454(1985). Alternatively, techniques described for the production of single chain antibodies (U.S. Pat. No. 4,946,778) can be adapted to produce evectin-specific single chain antibodies. Antibodies can also be produced by inducing in vivo production in the lymphocyte population or by screening recombinant immunoglobulin libraries or panels of highly specific binding reagents as disclosed in Orlandi et al., *Proc Natl Acad Sci* 86: 3833–3837 (1989), and Winter G. and Milstein C; *Nature* 349:293–299 (1991).

Antibody fragments that contain specific binding sites for evectin can also be generated. For example, such fragments include, but are not limited to, the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries can be constructed to allow rapid and easy identification of monoclonal Fab fragments with the desired specificity. (Huse W. D. et al. *Science* 256:1275–1281 (1989)).

By one approach, monoclonal antibodies to evectin or fragments thereof are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and derivative methods thereof Selected positive clones can be expanded and their monoclonal antibody product harvested for use. Detailed procedures for monoclonal antibody production are described in Davis, L. et al. *Basic Methods in Molecular Biology* Elsevier, N.Y. Section 21-2.

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and can require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988–991(1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: *Manual of Clinical Immunology,* 2d Ed. (Rose and Friedman, Eds.) Amer. Soc. For Microbiol., Washington, D.C. (1980). Antibody preparations prepared according to either protocol are useful in quantitative immunoassays that determine concentrations of antigen-bearing substances in biological samples; they are also used semi-quantitatively or qualitatively (e.g., in diagnostic embodiments that identify the presence of evectin in biological samples). Example 5 describes an approach that was used to make an anti-evt-1 polyclonal antibody. In the discussion that follows, several methods of molecular modeling and rational drug design are described.

These techniques can be applied to identify additional evectin family members, compounds that resemble an evectin or fragment or derivative thereof, and molecules that interact with evectins and, thereby modulate their function.

Rational Drug Design

Rational drug design involving polypeptides requires identifying and defining a first peptide with which the designed drug is to interact, and using the first target peptide to define the requirements for a second peptide. With such requirements defined, one can find or prepare an appropriate peptide or non-peptide that meets all or substantially all of the defined requirements. Thus, one goal of rational drug design is to produce structural or functional analogs of biologically active polypeptides of interest or of small molecules with which they interact (e.g., agonists, antagonists, null compounds) in order to fashion drugs that are, for example, more or less potent forms of the ligand. (See, e.g., Hodgson, *Bio. Technology* 9:19–21 (1991)). An example of rational drug design is shown in Erickson et al., *Science* 249:527–533 (1990). Combinatorial chemistry is the science of synthesizing and testing compounds for bioactivity en masse, instead of one by one, the aim being to discover drugs and materials more quickly and inexpensively than was formerly possible. Rational drug design and combinatorial chemistry have become more intimately related in recent years due to the development of approaches in computer-aided protein modeling and drug discovery. (See e.g., U.S. Pat. Nos. 4,908,773; 5,884,230; 5,873,052; 5,331,573; and 5,888,738).

The use of molecular modeling as a tool for rational drug design and combinatorial chemistry has dramatically increased due to the advent of computer graphics. Not only is it possible to view molecules on computer screens in three dimensions but it is also possible to examine the interactions of macromolecules such as enzymes and receptors and rationally design derivative molecules to test. (See Boorman, *Chem. Eng. News* 70:18–26 (1992). A vast amount of user-friendly software and hardware is now available and virtually all pharmaceutical companies have computer modeling groups devoted to rational drug design. Molecular Simulations Inc. (www.msi.com), for example, sells several sophisticated programs that allow a user to start from an amino acid sequence, build a two or three-dimensional model of the protein or polypeptide, compare it to other two and three-dimensional models, and analyze the interactions of compounds, drugs, and peptides with a three dimensional model in real time. Accordingly, in some embodiments of the invention, software is used to compare regions of evectins (e.g., evt-1 and evt-2) and molecules that interact with evectins (collectively referred to as "binding partners"—e.g., anti-evectin antibodies, G proteins, and G$\beta\gamma$ subunits), and fragments or derivatives of these molecules with other molecules, such as peptides, peptidomimetics, and chemicals, so that therapeutic interactions can be predicted and designed. (See Schneider, *Genetic Engineering News* December: page 20 (1998), Tempczyk et al., *Molecular Simulations Inc. Solutions* April (1997) and Butenhof, *Molecular Simulations Inc. Case Notes* (August 1998) for a discussion of molecular modeling).

For example, the protein sequence of an evectin or binding partner, or domains of these molecules (or nucleic acid sequence encoding these polypeptides or both), can be entered onto a computer readable medium for recording and manipulation. It will be appreciated by those skilled in the art that a computer readable medium having these sequences can interface with software that converts or manipulates the sequences to obtain structural and functional information, such as protein models. That is, the functionality of a software program that converts or manipulates these sequences includes the ability to compare these sequences to other sequences or structures of molecules that are present on publicly and commercially available databases so as to conduct rational drug design.

The evectin or binding partner polypeptide or nucleic acid sequence or both can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on a computer readable medium to generate manufactures comprising the nucleotide or polypeptide sequence information of this embodiment. A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media can be a hard disc, a floppy disc, a magnetic tape, zip disk, CD-ROM, DVD-ROM, RAM, or ROM as well as other types of other media known to those skilled in the art. The computer readable media on which the sequence information is stored can be in a personal computer, a network, a server or other computer systems known to those skilled in the art.

Embodiments of the invention utilize computer-based systems that contain the sequence information described herein and convert this information into other types of usable information (e.g., protein models for rational drug design). The term "a computer-based system" refers to the hardware, software, and any database used to analyze an evectin or a binding partner nucleic acid or polypeptide sequence or both, or fragments of these biomolecules so as to construct models or to conduct rational drug design. The computer-based system preferably includes the storage media described above, and a processor for accessing and manipulating the sequence data. The hardware of the computer-based systems of this embodiment comprise a central processing unit (CPU) and a database. A skilled artisan can readily appreciate that any one of the currently available computer-based systems are suitable.

In one particular embodiment, the computer system includes a processor connected to a bus that is connected to a main memory (preferably implemented as RAM) and a variety of secondary storage devices, such as a hard drive and removable medium storage device. The removable medium storage device can represent, for example, a floppy disk drive, a DVD drive, an optical disk drive, a compact disk drive, a magnetic tape drive, etc. A removable storage medium, such as a floppy disk, a compact disk, a magnetic tape, etc. containing control logic and/or data recorded therein can be inserted into the removable storage device. The computer system includes appropriate software for reading the control logic and/or the data from the removable medium storage device once inserted in the removable medium storage device. The evectin or binding partner nucleic acid or polypeptide sequence or both can be stored in a well known manner in the main memory, any of the secondary storage devices, and/or a removable storage medium. Software for accessing and processing these sequences (such as search tools, compare tools, and modeling tools etc.) reside in main memory during execution.

As used herein, "a database" refers to memory that can store an evectin or binding partner nucleotide or polypeptide sequence information, protein model information, information on other peptides, chemicals, peptidomimetics, and other agents that interact with evectin proteins, and values or results from functional assays. Additionally, a "database" refers to a memory access component that can access manufactures having recorded thereon evectin or binding partner nucleotide or polypeptide sequence information, protein model information, information on other peptides, chemicals, peptidomimetics, and other agents that interact with evectins, and values or results from functional assays. In other embodiments, a database stores an "evectin functional profile" comprising the values and results (e.g., ability to associate with membranes, modulate vesicle trafficking, bind G proteins, and/or modulate signal transduction and membrane biosynthesis and organization) from one or more "evectin functional assays", as described herein or known in the art, and relationships between these values or results. The sequence data and values or results from evectin functional assays can be stored and manipulated in a variety of data processor programs in a variety of formats. For example, the sequence data can be stored as text in a word processing file, such as Microsoft WORD or WORDPERFECT, an ASCII file, a html file, or a pdf file in a variety of database programs familiar to those of skill in the art, such as DB2, SYBASE, or ORACLE.

A "search program" refers to one or more programs that are implemented on the computer-based system to compare an evectin or binding partner nucleotide or polypeptide sequence with other nucleotide or polypeptide sequences and agents including but not limited to peptides, peptidomimetics, and chemicals stored within a database. A search program also refers to one or more programs that compare one or more protein models to several protein models that exist in a database and one or more protein models to several peptides, peptidomimetics, and chemicals that exist in a database. A search program is used, for example, to compare one evectin functional profile to one or more evectin functional profiles that are present in a database. Still further, a search program can be used to compare values or results from evectin functional assays and agents that modulate evectin-mediated signal transduction.

A "retrieval program" refers to one or more programs that can be implemented on the computer-based system to identify a homologous nucleic acid sequence, a homologous protein sequence, or a homologous protein model. A retrieval program can also used to identify peptides, peptidomimetics, and chemicals that interact with an evectin protein sequence, or an evectin protein model stored in a database. Further, a retrieval program is used to identify a specific agent that modulates evectin-mediated signal transduction to a desired set of values, results, or profile. That is, a retrieval program can also be used to obtain "a binding partner profile" that is composed of a chemical structure, nucleic acid sequence, or polypeptide sequence or model of an agent that interacts with an evectin and, thereby modulates (inhibits or enhances) signal transduction, vesicle trafficking, signal transduction, G protein binding, or membrane biosynthesis and organization. Further, a binding partner profile can have one or more symbols that represent these molecules and/or models, an identifier that represents one or more agents including, but not limited to peptides and peptidomimetics (referred to collectively as "peptide agents") and chemicals, and a value or result from a functional assay.

As a starting point to rational drug design, a two or three dimensional model of a polypeptide of interest is created (e.g., evt-1, evt-2, or a binding partner, such as a Gβγ subunit or an antibody). In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221–239 (1971). Using this technique, it is possible to elucidate three-dimensional structure with good precision. Additionally, protein structure can be determined through the use of techniques of neutron diffraction, or by nuclear magnetic resonance (NMR). (See, e.g., Moore, W. J., Physical Chemistry, $4^{th}$ Edition, Prentice-Hall, N.J. (1972)).

Alternatively, protein models of a polypeptide of interest can be constructed using computer-based protein modeling techniques. By one approach, the protein folding problem is solved by finding target sequences that are most compatible with profiles representing the structural environments of the residues in known three-dimensional protein structures. (See, e.g., U.S. Pat. No. 5,436,850). In another technique, the known three-dimensional structures of proteins in a given family are superimposed to define the structurally conserved regions in that family. This protein modeling technique also uses the known three-dimensional structure of a homologous protein to approximate the structure of a polypeptide of interest. (See e.g., U.S. Pat. Nos. 5,557,535; 5,884,230; and 5,873,052). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using the distance geometry program DRAGON that constructs a low resolution model. A full-atom representation is then constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and organismed to energy minimization using the molecular modeling package QUANTA. (See e.g., Aszódi et al., Proteins:Structure, Function, and Genetics, Supplement 1:38–42 (1997)).

In a preferred approach, the commercially available "Insight II 98" program (Molecular Simulations Inc.) and accompanying modules are used to create a two and/or three dimensional model of a polypeptide of interest from an amino acid sequence. Insight II is a three-dimensional graphics program that can interface with several modules that perform numerous structural analysis and enable real-time rational drug design and combinatorial chemistry. Modules such as Builder, Biopolymer, Consensus, and Converter, for example, allow one to rapidly create a two dimensional or three dimensional model of a polypeptide, carbohydrate, nucleic acid, chemical or combinations of the foregoing from their sequence or structure. The modeling tools associated with Insight II support many different data file formats including Brookhaven and Cambridge databases; AMPAC/MOPAC and QCPE programs; Molecular Design Limited Molfile and SD files, Sybel Mol2 files, VRML, and Pict files.

Additionally, the techniques described above can be supplemented with techniques in molecular biology to design models of the protein of interest. For example, a polypeptide of interest can be analyzed by an alanine scan (Wells, Methods in Enzymol. 202:390–411 (1991)) or other types of site-directed mutagenesis analysis. In alanine scan, each amino acid residue of the polypeptide of interest is sequentially replaced by alanine in a step-wise fashion (i.e., only one alanine point mutation is incorporated per molecule starting at position #1 and proceeding through the entire molecule), and the effect of the mutation on the peptide's activity in a functional assay is determined. Each of the amino acid residues of the peptide is analyzed in this manner and the regions important for the modulation of signal transduction or membrane association, for example, are identified. These functionally important regions can be recorded on a computer readable medium, stored in a database in a computer system, and a search program can be employed to generate a protein model of the functionally important regions.

Once a model of the polypeptide of interest is created, it can be compared to other models so as to identify new members of the evectin family and binding partners. By starting with the amino acid sequence or protein model of evt-1 or evt-2 or a binding partner, for example, molecules having two-dimensional and/or three-dimensional homology can be rapidly identified. In one approach, a percent sequence identity can be determined by standard methods that are commonly used to compare the similarity and position of the amino acid of two polypeptides. Using a computer program such as BLAST or FASTA, two polypeptides can be aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{total number of identical matches}}{[\text{length of the longer sequence within the matched span} + \text{number of gaps introduced into the longer sequence in order to align the two sequences}]} \times 100$$

Accordingly, the protein sequence corresponding to an evectin or a binding partner or a fragment or derivative of these molecules can be compared to known sequences on a protein basis. Protein sequences corresponding to an evectin, or a binding partner or a fragment or derivative of these molecules are compared, for example, to known amino acid sequences found in Swissprot release 35, PIR release 53 and Genpept release 108 public databases using BLASTP with the parameter W=8 and allowing a maximum of 10 matches. In addition, the protein sequences are compared to publicly known amino acid sequences of Swissprot using BLASTX with the parameter E=0.001. The molecules identified as members of the family of evectins or candidate binding partners desirably have at least 35% homology and preferably have 40%, 45%, 50% or 55% or greater homology to evt-1 or evt-2 The evectin family members and candidate binding partners that interact with an evectin can have the following degrees of homology to evt-1 or evt-2 or both, for example: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. The evectin family members and candidate binding partners having greater than or equal to 35% homology are identified and are subsequently examined using an evectin functional assay.

In another embodiment, computer modeling and the sequence-to-structure-to-function paradigm is exploited to identify more members of the evectin family candidate binding partners. By this approach, first the structure of an evectin (e.g., evt-1 or evt-2) or a candidate binding partner (e.g., Gβγ subunit or antibody) having a known response in a characterization assay is determined from its sequence using a threading algorithm, which aligns the sequence to the best matching structure in a structural database. Next, the protein's active site (i.e., the site important for a desired response in the characterization assay) is identified and a "fuzzy functional form" (FFF)—a three-dimensional descriptor of the active site of a protein—is created. (See e.g., Fetrow et al., *J. Mol. Biol.* 282:703–711 (1998) and Fetrow and Skolnick, *J. Mol. Biol.* 281: 949–968 (1998).

The FFFs are built by iteratively superimposing the protein geometries from a series of functionally related proteins with known structures. The FFFs are not overly specific, however, and the degree to which the descriptors can be relaxed is explored. In essence, conserved and functionally important residues for a desired response are identified and a set of geometric and conformational constraints for a specific function are defined in the form of a computer algorithm. The program then searches experimentally determined protein structures from a protein structural database for sets of residues that satisfy the specified constraints. In this manner, homologous three-dimensional structures can be compared and degrees (e.g., percentages of three-dimensional homology) can be ascertained. The ability to search three-dimensional structure databases for structural similarity to a protein of interest can also be accomplished by employing the Insight II using modules such as Biopolymer, Binding Site Analysis, and Profiles-3D.

By using this computational protocol, genome sequence data bases such as maintained by various organizations including: http://www.tigr.org/tdb; http://www.genetics.wisc.edu; http://genome-www.stanford.edu/~ball; http://hiv-web.lanl.gov; http://wwwncbi.nlm.nih.gov; http://www.ebi.ac.uk; http://pasteur.fr/other/biology; and http://www-genome.wi.mit.edu, can be rapidly screened for specific protein active sites and for identification of the residues at those active sites that resemble a desired molecule. Several other groups have developed databases of short sequence patterns or motifs designed to identify a given function or activity of a protein. Many of these databases, notably Prosite (http)://expasy.hcuge.ch/sprot/prosite.html): Blocks (http://www.blocks.fhcrc.org); Prints (http://www.biochem.ucl.ac.uk/bsm/dbbrowser/PRINTS/PRINTS.html), the Molecular Modelling Database (MMDB), and the Protein Data Bank can use short stretches of sequence information to identify sequence patterns that are specific for a given function; thus they avoid the problems arising from the necessity of matching entire sequences.

By a similar approach, a candidate binding partner can be identified and manufactured as follows. First, a molecular model of one or more molecules that are known to interact with an evectin or portions of these molecules that interact with an evectin are created using one of the techniques discussed above or as known in the art. Next, chemical libraries and databases are searched for molecules similar in structure to the known molecule. That is, a search can be made of a three dimensional data base for non-peptide (organic) structures (e.g., non-peptide analogs, and/or dipeptide analogs) having three dimensional similarity to the known structure of the target compound. See, e.g., the Cambridge Crystal Structure Data Base, Crystallographic Data Center, Lensfield Road, Cambridge, CB2 1EW, England; and Allen, F. H., et al., *Acta Crystallogr.*, B35: 2331–2339 (1979). The identified candidate binding partners that interact with evectins can then be analyzed in a functional assay (e.g., a G protein binding assay or membrane association assay or both) and new molecules can be modeled after the candidate binding partners that produce a desirable response. By cycling in this fashion, libraries of molecules that interact with evectins and produce a desirable or optimal response in a functional assay can be selected.

It is noted that search algorithms for three dimensional data base comparisons are available in the literature. See, e.g., Cooper, et al., *J. Comput.-Aided Mol. Design,* 3: 253–259 (1989) and references cited therein; Brent, et al.,*J. Comput.-Aided Mol. Design,* 2: 311–310 (1988) and references cited therein. Commercial software for such searches is also available from vendors such as Day Light Information Systems, Inc., Irvine, Calif. 92714, and Molecular Design Limited, 2132 Faralton Drive, San Leandro, Calif. 94577. The searching is done in a systematic fashion by simulating or synthesizing analogs having a substitute moiety at every residue level. Preferably, care is taken that replacement of portions of the backbone does not disturb the tertiary structure and that the side chain substitutions are compatible to retain the receptor substrate interactions.

By another approach, protein models of binding partners that interact with an evectin (e.g., a Gβγ subunit or antibody) can be made by the methods described above and these models can be used to predict the interaction of new molecules. Once a model of a binding partner is identified, the active sites or regions of interaction can be identified. Such active sites might typically be ligand binding sites. The active site can be identified using methods known in the art including, for example, from the amino acid sequences of peptides, from the nucleotide sequences of nucleic acids, or from study of complexes of the evectin with a ligand, such as Gβγ or specific G proteins. In the latter case, chemical or X-ray crystallographic methods can be used to find the active site by finding where on the evectin the complexed ligand is found (e.g. PHD or PHD and protein-protein module). Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures can be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method can be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site of the known binding partner, either experimentally, by modeling, or by a combination, candidate binding partners can be identified by searching databases containing compounds along with information on their molecular structure. Such a search seeks compounds having structures that match the determined active site structure and that interact with the groups defining the active site. Such a search can be manual, but is preferably computer assisted. One program that allows for such analysis is Insight II having the Ludi module. Further, the Ludi/ACD module allows a user access to over 65,000 commercially available drug candidates (MDL's Available Chemicals Directory) and provides the ability to screen these compounds for interactions with the protein of interest.

Alternatively, these methods can be used to identify improved binding partners from an already known binding partner. The composition of the known binding partner can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

A number of articles review computer modeling of drugs interactive with specific-proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific for the modulation of evectin-mediated signal transduction, membrane association, vesicle trafficking and other evectin functions.

Many more computer programs and databases can be used with embodiments of the invention to identify new members of the evectin family and binding partners that modulate evectin function. The following list is intended not to limit the invention but to provide guidance to programs and databases that are useful with the approaches discussed above. The programs and databases that can be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990), herein incorporated by reference), FASTA (Pearson and Lipman, *Proc. Natl. Acad. Sci. USA,* 85: 2444 (1988), herein incorporated by reference), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217–241 (1997)), ISIS (Molecular Simulations Inc.), Quanta/Protein Design (Molecular Simulations Inc.), WebLab Molecular Simulations Inc.), WebLab Diversity Explorer (Molecular Simulations Inc.), Gene Explorer (Molecular Simulations Inc.), SeqFold (Molecular Simulations Inc.), Biopendium (Inpharmatica), SBdBase (Structural Bioinformatics), the EMBL/Swissprotein database, the MDL Available Chemicals Directory database, the MDL Drug Data Report data base, the Comprehensive Medicinal Chemistry database, Derwents's World Drug Index database, and the BioByte-MasterFile database. Many other programs and data bases would be apparent to one of skill in the art given the present disclosure.

Once candidate binding partners have been identified, desirably, they are analyzed in a functional assay. Further cycles of modeling and functional assays can be employed to more narrowly define the parameters needed in a binding partner. Each binding partner and its response in a functional assay can be recorded on a computer readable media and a database or library of binding partners and respective responses in a functional assay can be generated. These databases or libraries can be used by researchers to identify important differences between active and inactive molecules so that compound libraries are enriched for binding partners that have favorable characteristics. The section below describes several evectin functional assays that can be used to characterize new evectin family members and candidate binding partners.

Evectin Characterization Assays

The term "evectin characterization assay" or "evectin functional assay" or "functional assay" the results of which can be recorded as a value in a "evectin functional profile", include assays that directly or indirectly evaluate the presence of an evectin nucleic acid or protein in a cell and the ability of an evectin to associate with a membrane, interact with another molecule, and/or modulate signal transduction and vesicle trafficking. Examples 2–6 teach several assays that are considered for the purposes of this disclosure to be evectin functional assays. Many more are provided in the discussion below.

Some functional assays involve binding assays that utilize multimeric agents. One form of multimeric agent concerns a manufacture comprising an evectin, hybrid, binding partner, or fragment thereof disposed on a support. These multimeric agents provide the evectin, hybrid, binding partner, or fragment thereof in such a form or in such a way that a sufficient affinity is achieved. A multimeric agent having an evectin, hybrid, or binding partner or fragment thereof is obtained by joining the desired polypeptide to a macromolecular support. A "support" can be a termed a carrier, a protein, a resin, a cell membrane, or any macromolecular structure used to join or immobilize such molecules. Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. An evectin, hybrid, or binding partner or fragment thereof can also be joined to inorganic carriers, such as silicon oxide material (e.g., silica gel, zeolite, diatomaceous earth or aminated glass) by, for example, a covalent linkage through a hydroxy, carboxy or amino group and a reactive group on the carrier.

In several multimeric agents, the macromolecular support has a hydrophobic surface that interacts with a portion of the evectin, hybrid, or binding partner or fragment thereof by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, an evectin, hybrid, or binding partner or fragment thereof can be covalently bound to carriers including proteins and oligo/polysaccharides (e.g. cellulose, starch, glycogen, chitosane or aminated sepharose). In these later multimeric agents, a reactive group on the molecule, such as a hydroxy or an amino group, is used to join to a reactive group on the carrier so as to create the covalent bond. Additional multimeric agents comprise a support that has other reactive groups that are chemically activated so as to attach the evectin, hybrid, or binding partner or fragment thereof. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma).

Furthermore, in some embodiments, a liposome or lipid bilayer (natural or synthetic) is contemplated as a support and evectins, hybrids, or binding partners are attached to the membrane surface or are incorporated into the membrane by techniques in liposome engineering. (See Example 7 for the preparation of a membrane-bound evectin). By one approach, liposome multimeric supports comprise an evectin, hybrid, or binding partner that is exposed on the surface. A hydrophobic domain can be joined to the evectin, hybrid, or binding partner so as to facilitate the interaction with the membrane. Carriers for use in the body, (i.e. for prophylactic or therapeutic applications) are desirably physiological, non-toxic and preferably, non-immunoresponsive. Suitable carriers for use in the body include poly-L-lysine, poly-D, L-alanine, liposomes, and Chromosorb® (Johns-Manville Products, Denver Co.). Ligand conjugated Chromosorb® (Synsorb-Pk) has been tested in humans for the prevention of hemolytic-uremic syndrome and was reported as not presenting adverse reactions. (Armstrong et al. *J. Infectious Diseases* 171:1042–1045 (1995)). For some embodiments, a "naked" carrier (i.e., lacking an attached binding partner) that has the capacity to attach an evectin or binding partner in the body of a organism is administered. By this approach, a "prodrug-type" therapy is envisioned in which the naked carrier is administered separately from the evectin or binding partner and, once both are in the body of the organism, the carrier and the evectin or binding partner are assembled into a multimeric complex.

The insertion of linkers, such as linkers (e.g., "λ linkers" engineered to resemble the flexible regions of λ phage) of an appropriate length between the evectin, hybrid, or binding partner and the support are also contemplated so as to encourage greater flexibility of the evectin, hybrid, or binding partner and thereby overcome any steric hindrance that can be presented by the support. The determination of an appropriate length of linker that allows for an optimal cellular response or lack thereof, can be determined by screening the evectins, hybrids, or binding partners with varying linkers in the assays detailed in the present disclosure.

A composite support comprising more than one type of evectin, hybrid, or binding partner is also envisioned. A "composite support" can be a carrier, a resin, or any macromolecular structure used to attach or immobilize two or more different binding partners or evectins. In some embodiments, a liposome or lipid bilayer (natural or synthetic) is contemplated for use in constructing a composite support and evectins or binding partners are attached to the membrane surface or are incorporated into the membrane using techniques in liposome engineering.

As above, the insertion of linkers, such as λxlinkers, of an appropriate length between the evectin or binding partner and the support is also contemplated so as to encourage greater flexibility in the molecule and thereby overcome any steric hindrance that can occur. The determination of an appropriate length of linker that allows for an optimal cellular response or lack thereof, can be determined by screening the evectins or binding partners with varying linkers in the assays detailed in the present disclosure.

In other embodiments of the invention, the multimeric and composite supports discussed above can have attached multimerized evectins, hybrids, or binding partners so as to create a "multimerized-multimeric support" and a "multimerized-composite support", respectively. A multimerized ligand can, for example, be obtained by coupling two or more binding partners in tandem using conventional techniques in molecular biology. The multimerized form of the evectin, hybrid, or binding partner can be advantageous for many applications because of the ability to obtain an agent with a higher affinity for an evectin, for example. The incorporation of linkers or spacers, such as flexible λ linkers, between the individual domains that make-up the multimerized agent can also be advantageous for some embodiments. The insertion of λ linkers of an appropriate length between protein binding domains, for example, can encourage greater flexibility in the molecule and can overcome steric hindrance. Similarly, the insertion of linkers between the multimerized binding partner or evectin or hybrid and the support can encourage greater flexibility and limit steric hindrance presented by the support. The determination of an appropriate length of linker can be determined by screening the evectins, hybrids, and binding partners with varying linkers in the assays detailed in this disclosure.

Thus, several approaches to identify agents that interact with an evectin, employ an evectin or a fragment thereof joined to a support. Once the support-bound evectin is obtained, for example, candidate binding partners are contacted to the support-bound evectin and an association is determined directly (e.g., by using labeled binding partner) or indirectly (e.g., by using a labeled antibody directed to the binding partner). Candidate binding partners are identified as binding partners by virtue of the association with the support-bound evectin. The properties of the binding partners are analyzed and derivatives are made using rational drug design and combinatorial chemistry. Candidate binding partners can be obtained from random chemical or peptide libraries but, preferably, are rationally selected. For example, monoclonal antibodies that bind to an evectin can be created and the nucleic acids encoding the VH and VL domains of the antibodies can be sequenced. These sequences can then be used to synthesize peptides that bind to the evectin. Further, peptidomimetics corresponding to these sequences can be created. These molecules can then be used as candidate binding partners.

Additionally, a cell based approach can be used characterize new evectin family members or evectin hybrids or to rapidly identify binding partners that interact with an evectin and, thereby, modulate signal transduction. Preferably, molecules identified in the support-bound evectin assay described above are used in the cell based approach, however, randomly generated compounds can also be used.

Several receptors that couple to pertussis toxin-sensitive G proteins have been shown to activate mitogen-activated protein kinase (MAPK) in various cell types. Research has also demonstrated that MAPK modulates the phosphorylation of Myelin Basic Protein (MBP) during myelinogenesis and in the demyelinating disease multiple scelerosis. (See Atkins et al., *J. Neurochem.* 73:1090 (1999), for a discussion of the signal transduction pathways contributing to myelination). In COS-7 cells and Rat 1 fibroblasts the activation of MAPK is dependent upon the activation of p21$^{ras}$ and is independent of protein kinase C. Recently, Gβ subunits have been implicated in direct Ras-dependent activation of MAPK because coexpression of Gβγ subunits in COS-7 cells induced MAPK and Ras activation but these events were overcome by expressing peptides having a pleckstrin homology domain that binds Gβ65 and PIP2. (See Lutrell et al., *J. Biol. Chem.* 270:12984 (1995), herein incorporated by reference). A similar in vitro analysis can be performed to evaluate the ability of evectins and evectin-like hybrids to modulate MAPK and RAS activation, as well as, MBP phosphorylation. Further, this system can be used to identify binding partners that inhibit or enhance evectin-mediated MAPK and RAS activation.

The effect of evectins and hybrids on MAPK activation can be determined as follows. COS-7 cells, maintained in Dulbecco's modified Eagle's medium (DMEM) supplemented with 10% fetal bovine serum and 100 μg/ml gentamicin are cotransfected with the Gi coupled α-2C10 adrenergic receptor and a nucleic acid encoding an evectin or evectin-like hybrid. For transfection using DEAE-dextran, cells are seeded in 6-well tissue culture plates and are transfected with a total of 1–2 μg of total DNA. For transfection using LipofectAMINE, cells in 6-well dishes are incubated at 37° C. with a mixture of 1 ml serum free DMEM containing 2 μg of total DNA/well and 12 μl of LipofectAMINE. After 5 hours, 1 ml of DMEM containing 20% fetal bovine serum is added and the cells are allowed to incubate overnight.

Receptor stimulated MAPK activity is then determined following immunoprecipitation of endogenous p42$^{MAPK}$ with an antibody-agarose conjugate (8 μg) plus 25 μl of a 50% slurry of Protein A-agarose. Immune complexes are washed in a kinase buffer (20 mM Hepes, pH 7.4, 10 MM MgCl$_2$, and 1 mM DTT). The immune complexes are resuspended in the kinase buffer, to which is added 250 μg/ml MBP, 20 μM ATP, 2.5 μCi γ-$^{32}$P ATP. The kinase reaction is allowed to proceed for 20 minutes at 30° C. and phosphorylated MBP is detected by SDS-polyacrylamide gel electrophoresis. If the evectin or hybrid attenuates activation of MAPK, then a reduction in the amount of phosphorylated MBP will be observed, as compared to controls in which no evectin or hybrid was transfected.

The effect of evectins and evectin-like hybrids on p21$^{ras}$ can also be determined as follows. COS-7 cells, transfected as above, are serum-starved overnight and are labeled for 2 hours in phosphate-free DMEM containing $^{32}$P orthophosphate (200 μCi/ml), and are stimulated for 2 minutes with or without an agonist (e.g., UK-14304). Following agonist stimulation, monolayers are lysed in detergent buffer (25 mM Tris-HCl, pH 7.5, 150 mM NaCl, 25 mM MgCl2, 1% NP40) and p21$^{ras}$ is immunoprecipitated using the monoclonal antibody Y13-259 (Oncogene Science) with protein G-sepharose (75 μl of a 20% slurry). P21$^{ras}$-bound GDP and GTP are resolved by thin layer chromatography on polyethylenimine-cellulose plates in 0.75M KH$_2$PO$_4$ (pH 3.4). COS-7 cells transfected with some evectin and evectin-like hybrids are expected to show impaired agonist-stimulated p21$^{ras}$-GTP exchange compared with controls.

The assays described above can also be performed in the presence and absence of candidate binding partners, preferably binding partners identified by a support-bound assay. The MAPK kinase assay, for example can be modified by contacting the cell with candidate binding partner prior to cell lysis for the immunoprecipitation step. By analyzing MAPK kinase activation in the presence and absence of the candidate binding partner, one of skill can rapidly determine whether the binding partner is effective at modulating signal transduction. Similarly, the RAS activation assay can be performed by contacting the cells with a candidate binding partner prior to cell lysis for immunoprecipitation and the effect of the binding partner on RAS activation can be determined by comparing RAS-GTP exchange in the presence and absence of the binding partner.

Other evectin characterization assays take advantage of techniques in molecular biology that are employed to discover protein:protein interactions. One method that detects protein-protein interactions in vivo, the two-hybrid system, is described in detail for illustration only and not by way of limitation. Other similar assays that can be can be adapted to identify binding partners include:

(1) the two-hybrid systems (Field & Song, *Nature* 340:245–246 (1989); Chien et al., *Proc. Natl. Acad. Sci. USA* 88:9578–9582 (1991); and Young K H, *Biol. Reprod.* 58:302–311 (1998), all references herein expressly incorporated by reference);

(2) reverse two-hybrid system (Leanna & Hannink, *Nucl. Acid Res.* 24:3341–3347 (1996), herein incorporated by reference);

(3) repressed transactivator system (Sadowski et al., U.S. Pat. No. 5,885,779), herein incorporated by reference);

(4) phage display (Lowman H B, *Annu. Rev. Biophys. Biomol. Struct.* 26:401–424 (1997), herein incorporated by reference); and (5) GST/HIS pull down assays, mutant operators (Granger et al., WO 98/01879) and the like (See also Mathis G., *Clin. Chem.* 41:139–147 (1995); Lam K. S. *Anticancer Drug Res.*, 12:145–167 (1997); and Phizicky et al., *Microbiol. Rev.* 59:94–123 (1995), all references herein expressly incorporated by reference).

An adaptation of the system described by Chien et al., 1991, Proc. Natl. Acad. Sci. USA, 88:9578–9582, herein incorporated by reference), which is commercially available from Clontech (Palo Alto, Calif.) is as follows. Plasmids are constructed that encode two hybrid proteins: one plasmid consists of nucleotides encoding the DNA-binding domain of a transcription activator protein fused to a nucleotide sequence encoding an evectin or fragment thereof, and the other plasmid consists of nucleotides encoding the transcription activator protein's activation domain fused to a cDNA encoding an unknown protein that has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, evectins can be used as the bait gene product. Total genomic or cDNA sequences are fused to the DNA encoding an activation domain. This library and a plasmid encoding a hybrid of a bait gene encoding the evectin product (evt-1) fused to the DNA-binding domain are cotransformed into a yeast reporter strain, and the resulting transformants are screened for those that express the reporter gene. For example, and not by way of limitation, a bait gene sequence encoding an evectin can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait evectin are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait evectin gene-GAL4 fusion plasmid into a yeast strain which contains a lacZ gene driven by a promoter which contains GAL4 activation sequence. A cDNA encoded protein, fused to GAL4 transcriptional activation domain, that interacts with bait evectin gene product will reconstitute an active GAL4 protein and thereby drive expression of the lacZ gene. Colonies that express lacZ can be detected and the cDNA can then be purified from these strains, and used to produce and isolate the binding partner by techniques routinely practiced in the art. In the disclosure below, several diagnostic embodiments of the invention are described.

Diagnostic Embodiments

Some diseases that can be diagnosed with embodiments of the invention include retinal diseases, such as adFEVR, and neuropathies, such as multiple sclerosis. Generally, the diagnostics of the invention can be classified according to whether the embodiment is a nucleic acid or protein-based assay. Some diagnostic assays detect mutations or polymorphisms in evectin nucleic acids or proteins, which contribute to aberrations in vesicle trafficking, signal transduction, G protein binding, or membrane biosynthesis and organization. Other diagnostic assays identify and distinguish defects in vesicle trafficking, signal transduction, G protein binding, or membrane biosynthesis and organization by detecting a level of evectin RNA or protein in a tested organism that resembles the level of evectin RNA or protein in a organism suffering from a disease or by detecting a level of RNA or protein in a tested organism that is different than an organism not suffering from a disease. Additionally, some maladies involving defects in vesicle trafficking, signal transduction, G protein binding, or membrane biosynthesis and organization can be diagnosed by monitoring the levels of one or more evectins in various tissues and/or comparing the ratios of one evectin to another (e.g., evt-1 to evt-2) or the ratio of one evectin in one tissue type to the same evectin in another tissue type.

Additionally, the manufacture of kits that incorporate the reagents and methods described in the following embodiments so as to allow for the rapid detection and identification of aberrations in vesicle trafficking, signal transduction, G protein binding, or membrane biosynthesis and organization are contemplated. The diagnostic kits can include a nucleic acid probe or an antibody or combinations thereof, which specifically detect a mutant form of evectin or a nucleic acid probe or an antibody or combinations thereof, which can be used to determine the level of RNA or protein expression of one or more evectin. The detection component of these kits will typically be supplied in combination with one or more of the following reagents. A support capable of absorbing or otherwise binding DNA, RNA, or protein will often be supplied. Available supports include membranes of nitrocellulose, nylon or derivatized nylon that can be characterized by bearing an array of positively charged substituents. One or more restriction enzymes, control reagents, buffers, amplification enzymes, and non-human polynucleotides like calf-thymus or salmon-sperm DNA can be supplied in these kits.

Useful nucleic acid-based diagnostic techniques include, but are not limited to, direct DNA sequencing, Southern Blot analysis, single-stranded confirmation analysis (SSCA), RNAse protection assay, dot blot analysis, nucleic acid amplification, and combinations of these approaches. The starting point for these analysis is isolated or purified nucleic acid from a biological sample. It is contemplated that tissue biopsies would provide a good sample source. Further, if the diagnostic assay is designed to determine the presence of a mutant or polymorphic evectin, any source of DNA including, but not limited to hair, cheek cells and blood can be used as a biological sample. The nucleic acid is extracted from the sample and can be amplified by a DNA amplification technique such as the Polymerase Chain Reaction (PCR) using primers that correspond to regions flanking DNA that encodes amino acid residues recognized as a polymorphism linked to a defect in vesicle trafficking, signal transduction, G protein binding, or membrane biosynthesis and organization.

Once a sufficient amount of DNA is obtained from an individual to be tested, several methods can be used to detect an evectin polymorphism. Direct DNA sequencing, either manual sequencing or automated fluorescent sequencing can detect such sequence variations. Another approach is the single-stranded confirmation polymorphism assay (SSCA) (Orita et al., *Proc. Natl. Acad. Sci. USA* 86:2776–2770 (1989), herein incorporated by reference). This method, however, does not detect all sequence changes, especially if the DNA fragment size is greater than 200 base pairs, but can be optimized to detect most DNA sequence variation.

The reduced detection sensitivity is a disadvantage, but the increased throughput possible with SSCA makes it an attractive, viable alternative to direct sequencing for mutation detection. The fragments that have shifted mobility on SSCA gels are then sequenced to determine the exact nature of the DNA sequence variation. Other approaches based on the detection of mismatches between the two complimentary DNA strands include clamped denaturing gel electrophoresis (CDGE) (Sheffield et al., *Am. J. Hum. Genet.* 49:699–706 (1991)), heteroduplex analysis (HA) (White et al., *Genomics* 12:301–306 (1992)), and chemical mismatch cleavage (CMC) (Grompe et al., *Proc. Natl. Acad. Sci. USA* 86:5855–5892 (1989)). A review of currently available methods of detecting DNA sequence variation can be found in Grompe, *Nature Genetics* 5:111–117 (1993).

Seven well-known nucleic acid-based methods for confirming the presence of a polymorphism are described below. Provided for exemplary purposes only and not intended to limit any aspect of the invention, these methods include:

(1) single-stranded confirmation analysis (SSCA) (Orita et al.);

(2) denaturing gradient gel electrophoresis (DGGE) (Wartell et al., *Nucl. Acids Res.* 18:2699–2705 (1990) and Sheffield et al., *Proc. Natl. Acad. Sci. USA* 86:232–236 (1989)), both references herein incorporated by reference;

(3) RNAse protection assays (Finkelstein et al., *Genomics* 7:167–172 (1990) and Kinszler et al., *Science* 251:1366–1370 (1991)) both references herein incorporated by reference;

(4) the use of proteins which recognize nucleotide mismatches, such as the *E. Coli* mutS protein (Modrich, Ann. Rev. Genet. 25:229–253 (1991), herein incorporated by reference;

(5) allele-specific PCR (Rano and Kidd, Nucl. Acids Res. 17:8392 (1989), herein incorporated by reference), which involves the use of primers that hybridize at their 3' ends to a polymorphism and, if the polymorphism is not present, an amplification product is not observed; and (6) Amplification Refractory Mutation System (ARMS), as disclosed in European Patent Application Publication No. 0332435 and in Newton et al., *Nucl. Acids Res.* 17:2503–2516 (1989), both references herein incorporated by reference; and (7) temporal temperature gradient gel electrophoresis (TTGE), as described by Bio-Rad in U.S./E.G. Bulletin 2103, herein incorporated by reference.

In SSCA, DGGE, TTGE, and RNAse protection assay, a new electrophoretic band appears when the polymorphism is present. SSCA and TTGE detect a band that migrates differentially because the sequence change causes a difference in single-strand, intramolecular base pairing, which is detectable electrophoretically. RNAse protection involves cleavage of the mutant polynucleotide into two or more smaller fragments. DGGE detects differences in migration rates of sequences using a denaturing gradient gel. In an allele-specific oligonucleotide assay (ASOs) (Conner et al., *Proc. Natl. Acad. Sci. USA* 80:278–282 (1983)), an oligonucleotide is designed that detects a specific sequence, and an assay is performed by detecting the presence or absence of a hybridization signal. In the mutS assay, the protein binds only to sequences that contain a nucleotide mismatch in a heteroduplex between polymorphic and non-polymorphic sequences. Mismatches, in this sense of the word refers to hybridized nucleic acid duplexes in which the two strands are not 100% complementary. The lack of total homology results from the presence of one or more polymorphisms in an amplicon obtained from a biological sample, for example, that has been hybridized to a non-polymorphic strand. Mismatched detection can be used to detect point mutations in DNA or in an mRNA. While these techniques are less sensitive than sequencing, they are easily performed on a large number of biological samples and are amenable to array technology.

In some embodiments, nucleic acid probes that differentiate polynucleotides encoding wild type evectin from mutant evectin are attached to a support in an ordered array, wherein the nucleic acid probes are attached to distinct regions of the support that do not overlap with each other. Preferably, such an ordered array is designed to be "addressable" where the distinct locations of the probe are recorded and can be accessed as part of an assay procedure. These probes are joined to a support in different known locations. The knowledge of the precise location of each nucleic acid probe makes these "addressable" arrays particularly useful in binding assays. The nucleic acids from a preparation of several biological samples are then labeled by conventional approaches (e.g., radioactivity or fluorescence) and the labeled samples are applied to the array under conditions that permit hybridization.

If a nucleic acid in the samples hybridizes to a probe on the array, then a signal will be detected at a position on the support that corresponds to the location of the hybrid. Since the identity of each labeled sample is known and the region of the support on which the labeled sample was applied is known, an identification of the presence of the polymorphic variant can be rapidly determined. These approaches are easily automated using technology known to those of skill in the art of high throughput diagnostic or detection analysis.

Additionally, an opposite approach to that presented above can be employed. Nucleic acids present in biological samples can be disposed on a support so as to create an addressable array. Preferably, the samples are disposed on the support at known positions that do not overlap. The presence of nucleic acids having a desired polymorphism in each sample is determined by applying labeled nucleic acid probes that complement nucleic acids that encode the polymorphism and detecting the presence of a signal at locations on the array that correspond to the positions at which the biological samples were disposed. Because the identity of the biological sample and its position on the array is known, the identification of the polymorphic variant can be rapidly determined. These approaches are also easily automated using technology known to those of skill in the art of high throughput diagnostic analysis.

Any addressable array technology known in the art can be employed with this aspect of the invention. One particular embodiment of polynucleotide arrays is known as Genechips™, and has been generally described in U.S. Pat. No. 5,143,854; PCT publications WO 90/15070 and 92/10092. These arrays are generally produced using mechanical synthesis methods or light directed synthesis methods, which incorporate a combination of photolithographic methods and solid phase oligonucleotide synthesis. (Fodor et al., *Science,* 251:767–777, (1991)). The immobilization of arrays of oligonucleotides on solid supports has been rendered possible by the development of a technology generally identified as "Very Large Scale Immobilized Polymer Synthesis" (VLSPIS™) in which, typically, probes are immobilized in a high density array on a solid surface of a chip. Examples of VLSPIS™ technologies are provided in U.S. Pat. Nos. 5,143,854 and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and diagnostic information. Examples of such presentation strategies are disclosed in PCT Publications WO 94/12305, WO 94/11530, WO 97/29212, and WO 97/31256.

A wide variety of labels and conjugation techniques are known by those skilled in the art and can be used in various nucleic acid assays. There are several ways to produce labeled nucleic acids for hybridization or PCR including, but not limited to, oligolabeling, nick translation, end-labeling, or PCR amplification using a labeled nucleotide. Alternatively, a nucleic acid encoding an evectin can be cloned into a vector for the production of an mRNA probe. Such vectors are known in the art, are commercially available, and can be used to synthesize RNA probes in vitro by addition of an appropriate RNA polymerase such as T7, T3 or SP6 and labeled nucleotides. A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents, as well as, substrates, cofactors, inhibitors, magnetic particles and the like.

The RNAse protection method, briefly described above, is an example of a mismatch cleavage technique that is amenable to array technology. Preferably, the method involves the use of a labeled riboprobe that is complementary to an evectin sequence having a polymorphism. However, the method can involve the use of a labeled riboprobe that is complementary to an evectin sequence having the wild type gene. The riboprobe and either mRNA or DNA isolated and amplified from a biological sample are annealed (hybridized) and subsequently digested with the enzyme RNAse A, which is able to detect mismatches in a duplex RNAse structure. If a mismatch is detected by RNAse A, the polymorphic variant is not present in the sample and the enzyme cleaves at the site of the mismatch and destroys the riboprobe. Thus, when the annealed RNA is separated on a electrophoretic gel matrix, if a mismatch has been detected and cleaved by RNAse A, an RNA product will be seen which is much smaller than the full length duplex RNA for the riboprobe and the mRNA or DNA.

Complements to the riboprobe can also be dispersed on an array and stringently probed with the products from the Rnase A digestion after denaturing any remaining hybrids. In this case, if a mismatch is detected and probe destroyed by Rnase A, the complements on the array will not anneal with the degraded RNA under stringent conditions. In a similar fashion, DNA probes can be used to detect mismatches, through enzymatic or chemical cleavage. See, e.g., Cotton, et al., *Proc. Natl. Acad. Sci. USA* 85:4397 (1988); Shenk et al., *Proc. Natl. Acad. Sci. USA* 72:989 (1975); and Novack et al., *Proc. Natl. Acad. Sci. USA* 83:586 (1986). Mismatches can also be detected by shifts in the electrophoretic ability of mismatched duplexes relative to matched duplexes. (See, e.g., Cariello, Human *Genetics* 42:726 (1988), herein incorporated by reference). With any of the techniques described above, the mRNA or DNA from a tested organism that corresponds to regions of an evectin having a polymorphism can be amplified by PCR before hybridization.

The presence of an evectin polymorphism or wild type sequence in a protein sample can also be detected by using conventional assays. For example, antibodies immunoreactive with an evectin polymorphism can be used to screen biological samples for the presence of a defect in vesicle trafficking, signal transduction, G protein binding, or membrane biosynthesis and organization. Additionally, antibodies that differentiate the wild type evectins from mutant evectins can be used to determine that an organism does not have a defect in vesicle trafficking, signal transduction, G protein binding, or membrane biosynthesis and organization. In preferred embodiments, antibodies are used to immunoprecipitate the wildtype or mutant forms of evectins from solution or are used to react with the wild type or mutant evectins on Western or Immunoblots. Favored diagnostic embodiments also include enzyme-linked immunosorbant assays (ELISA), radioimmunoassays (RIA), immunoradiometric assays (IRMA) and immunoenzymatic assays (IEMA), including sandwich assays using monoclonal and/ or polyclonal antibodies. Exemplary sandwich assays are described by David et al., in U.S. Pat. Nos. 4,376,110 and 4,486,530, hereby incorporated by reference. Other embodiments employ aspects of the immune-strip technology disclosed in U.S. Pat. Nos. 5,290,678; 5,604,105; 5,710,008; 5,744,358; and 5,747,274, herein incorporated by reference.

In another preferred protein-based diagnostic, antibodies of the invention are attached to a support in an ordered array wherein a plurality of antibodies are attached to distinct regions of the support that do not overlap with each other. As with the nucleic acid-based arrays, the protein-based arrays are ordered arrays that are designed to be "addressable" such that the distinct locations are recorded and can be accessed as part of an assay procedure. These probes are joined to a support in different known locations. The knowledge of the precise location of each probe makes these "addressable" arrays particularly useful in binding assays. For example, an addressable array can comprise a support having several regions to which are joined a plurality of antibody probes that specifically recognize a particular evectin and differentiate the mutant and wild type evectins.

Proteins are obtained from biological samples and are labeled by conventional approaches (e.g., radioactivity, calorimetrically, or fluorescently). The labeled samples are then applied to the array under conditions that permit binding. If a protein in the sample binds to an antibody probe on the array, then a signal will be detected at a position on the support that corresponds to the location of the antibody-protein complex. Since the identity of each labeled sample is known and the region of the support on which the labeled sample was applied is known, an identification of the presence, concentration, and/or expression level can be rapidly determined. That is, by employing labeled standards of a known concentration of mutant or wild-type evectin, an investigator can accurately determine the protein concentration of the particular evectin in a tested sample and can also assess the expression level of the evectin. Conventional methods in densitometry can also be used to more accurately determine the concentration or expression level of the evectin. These approaches are easily automated using technology known to those of skill in the art of high throughput diagnostic analysis.

In another embodiment, an opposite approach to that presented above can be employed. Proteins present in biological samples can be disposed on a support so as to create an addressable array. Preferably, the protein samples are disposed on the support at known positions that do not overlap. The presence of a protein encoding a mutant or wild-type evectin in each sample is then determined by applying labeled antibody probes that recognize epitopes specific for the mutant or wild-type form of evectin. Because the identity of the biological sample and its position on the array is known, an identification of the presence, concentration, and/or expression level of a particular polymorphism can be rapidly determined.

That is, by employing labeled standards of a known concentration of mutant and/or wild-type evectin, an investigator can accurately determine the concentration of evectin in a sample and from this information can assess the expression level of the particular form of evectin. Conventional methods in densitometry can also be used to more accurately determine the concentration or expression level of the evectin. These approaches are also easily automated using technology known to those of skill in the art of high throughput diagnostic analysis. As detailed above, any addressable array technology known in the art can be employed with this aspect of the invention and display the protein arrays on the chips in an attempt to maximize antibody binding patterns and diagnostic information.

As discussed above, the presence or detection of a polymorphism in an evectin can provide a diagnosis of a defect in vesicle trafficking, signal transduction, G protein binding, or membrane biosynthesis and organization in an organism. Additional embodiments include the preparation of diagnostic kits comprising detection components, such as antibodies, specific for a particular polymorphic variant of evectin. The detection component will typically be supplied in combination with one or more of the following reagents. A support capable of absorbing or otherwise binding RNA or protein will often be supplied. Available supports for this purpose include, but are not limited to, membranes of nitrocellulose, nylon or derivatized nylon that can be characterized by bearing an array of positively charged substituents, and Genechips™ or their equivalents. One or more enzymes, such as Reverse Transcriptase and/or Taq polymerase, can be furnished in the kit, as can dNTPs, buffers, or non-human polynucleotides like calf-thymus or salmon-sperm DNA. Results from the kit assays can be interpreted by a healthcare provider or a diagnostic laboratory. Alternatively, diagnostic kits are manufactured and sold to private individuals for self-diagnosis.

In addition to diagnosing disease according to the presence or absence of a polymorphism in an evectin DNA, mRNA, or protein, some diseases involving defects in vesicle trafficking, signal transduction, G protein binding, or membrane biosynthesis and organization result from skewed levels of evectins in particular tissues or aberrant patterns of evectin expression. By monitoring the level of expression of specific evectins in various tissues, for example, a diagnosis can be made or a disease state can be identified. Similarly, by determining ratios of the level of expression of various evectins in specific tissues (e.g., patterns of evectin expression) a prognosis of health or disease can be made. The levels of evectin expression in various tissues from healthy individuals, as well as, individuals suffering from a defect in vesicle trafficking, signal transduction, G protein binding, or membrane biosynthesis and organization is determined. These values can be recorded in a database and can be compared to values obtained from tested individuals. Additionally, the ratios or patterns of evectin expression in various tissues from both healthy and diseased individuals is recorded in a database. These analyses are referred to as "disease state profiles" and by comparing one disease state profile (e.g. from a healthy or diseased individual) to a disease state profile from a tested individual, a clinician can rapidly diagnose the presence or absence of disease. Databases having measurements of evectin expression of several individuals afflicted with a defect in vesicle trafficking, signal transduction, G protein binding, or membrane biosynthesis and organization are valuable standards by which the progression of disease can be monitored. In this manner, deviation between the standard and the organism values establishes the severity of disease state.

The nucleic acid and protein-based diagnostic techniques described above can be used to detect the level or amount or ratio of expression of a evectin RNAs or proteins in a tissue. Through quantitative Northern hybridizations, In situ analysis, immunohistochemistry, ELISA, genechip array technology, PCR, and Western blots, for example, the amount or level of expression of RNA or protein for a particular evectin (wild-type or mutant) can be rapidly determined and from this information ratios of evectin expression can be ascertained. Preferably, the expression levels of evt-1 and evt-2 are measured to determine the ratios. Alternatively, the evectins to be analyzed can be evectins that are currently unknown but which are identified based on their possession of one or more of the homology regions described above.

One diagnostic approach, for example, involves a method of correlating the ratio between the expression levels of a plurality of evectins with a disease state. To practice this method, biological samples from individuals suffering from a defect in vesicle trafficking, signal transduction, G protein binding, or membrane biosynthesis and organization and biological samples from normal individuals are obtained. Next, the expression levels of two or more evectins in the samples is determined and a determination is made as to whether there is a statistically significant association between the ratio of evectin expression and the defect in vesicle trafficking, signal transduction, G protein binding, or membrane biosynthesis and organization. Statistically significant associations can be determined using statistical methods familiar to those skilled in the art, including t test and chi-square analyses.

Once the levels of various evectins are determined, the information can be recorded onto a computer readable media, such as a hard drive, floppy disk, DVD drive, zip drive, etc. After recording and the generation of a database comprising the levels of expression of the various evectins studied, a comparing program is used which compares the levels of expression of the various evectins so as to create a ratio of expression. In a first comparison, an evectin to evectin ratio is generated. For example, desirable evectin to evectin ratios include, but are not limited to: evt-1:evt-2. As other newly found evectins are identified, the screening for their expression patterns and incorporation of the levels of expression into a ratio analysis approach to disease prognosis is contemplated. In a second comparison, the evectin to evectin ratios from normal organisms are compared to evectin to evectin ratios of organisms having various defects in vesicle trafficking, signal transduction, G protein binding, or membrane biosynthesis and organization. Preferably, the diseased organisms studied initially have been identified as having a form of myelination defect such as adFEVR or MS. Desirably, several databases are generated comprising the evectin to evectin ratios from normal organisms and the evectin to evectin ratios from diseased organisms so that a statistical analysis can be accurately performed. In this manner, patterns of evectin expression are analyzed and the predisposition to a defect in vesicle trafficking, signal transduction, G protein binding, or membrane biosynthesis and organization is determined. The following section describes the preparation of pharmaceuticals having evectins, hybrids, binding partners, or fragments thereof, which can be administered to organisms in need to modulate vesicle trafficking, signal transduction, G protein binding, or membrane biosynthesis and organization.

Pharmaceutical Preparations and Methods of Administration

The evectins, hybrids, binding agents, and fragments thereof are suitable for incorporation into pharmaceuticals that treat organisms in need of a compound that modulates vesicle trafficking, signal transduction, G protein binding, or membrane biosynthesis and organization. These pharmacologically active compounds can be processed in accordance with conventional methods of galenic pharmacy to produce medicinal agents for administration to organisms, e.g., plants, insects, mold, yeast, animals, and mammals including humans. The active ingredients can be incorporated into a pharmaceutical product with and without modification. Further, the manufacture of pharmaceuticals or therapeutic agents that deliver the pharmacologically active compounds of this invention by several routes are aspects of the invention. For example, and not by way of limitation, DNA, RNA, and viral vectors having sequence encoding the evectins, hybrids, binding partners, or fragments thereof are used with embodiments. Nucleic acids encoding evectins, hybrids, binding partners, or fragments thereof can be administered alone or in combination with other active ingredients.

The compounds of this invention can be employed in admixture with conventional excipients, i.e., pharmaceutically acceptable organic or inorganic carrier substances suitable for parenteral, enteral (e.g., oral) or topical application that do not deleteriously react with the pharmacologically active ingredients of this invention. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable vehicles are described in *Remmington's* Pharmaceutical Sciences, 15th Edition, Easton:Mack Publishing Company, pages 1405–1412 and 1461–1487 (1975) and The National *Formulary* XIV, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular pharmaceutical formulation having evectins, hybrids, binding partners, or fragments thereof can vary based on the individual needs of the patient and the treatment or preventative measure sought. Therapeutic efficacy and toxicity of such compounds can be determined by standard pharmaceutical procedures in cell cultures or experimental animals, e.g., ED50 (the dose therapeutically effective in 50% of the population). For example, the evectins, hybrids, binding partners, or fragments thereof discussed above, can be administered to the knockout mice of the invention and the effect on vesicle trafficking, signal transduction, G protein binding, or membrane biosynthesis and organization can be determined. The data obtained from these assays is then used in formulating a range of dosage for use with other organisms, including humans. The dosage of such compounds lies preferably within a range of circulating concentrations that include the ED50 with no toxicity. The dosage varies within this range depending upon type of evectin, hybrid, binding partner, or fragment thereof, the dosage form employed, sensitivity of the organism, and the route of administration.

Normal dosage amounts of various evectins, hybrids, binding partners, or fragments thereof can vary from approximately 1 to 100,000 micrograms, up to a total dose of about 10 grams, depending upon the route of administration. Desirable dosages include 250 $\mu$g, 500 $\mu$g, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5 g, 6 g, 7 g, 8 g, 9 g, and 10 g.

In some embodiments, the dose of evectins, hybrids, binding partners, or fragments thereof preferably produces a tissue or blood concentration or both from approximately 0.1 $\mu$M to 500 mM. Desirable doses produce a tissue or blood concentration or both of about 1 to 800 $\mu$M. Preferable doses produce a tissue or blood concentration of greater than about 10 $\mu$M to about 500 $\mu$M. Preferable doses are, for example, the amount of Kit modulators required to achieve a tissue or blood concentration or both of 10 $\mu$M, 15 $\mu$M, 20 $\mu$M, 25 $\mu$M, 30 $\mu$M, 35 $\mu$M, 40 $\mu$M, 45 $\mu$M, 50 $\mu$M, 55 $\mu$M, 60 $\mu$M, 65 $\mu$M, 70 $\mu$M, 75 $\mu$M, 80 $\mu$M, 85 $\mu$M, 90 $\mu$M, 95 $\mu$M, 100 $\mu$M, 110 $\mu$M, 120 $\mu$M, 130 $\mu$M, 140 $\mu$M, 145 $\mu$M, 150 $\mu$M, 160 $\mu$M, 170 $\mu$M, 180 $\mu$M, 190 $\mu$M, 200 $\mu$M, 220 $\mu$M, 240 $\mu$M, 250 $\mu$M, 260 $\mu$M, 280 $\mu$M, 300 $\mu$M, 320 $\mu$M, 340 $\mu$M, 360 $\mu$M, 380 $\mu$M, 400 $\mu$M, 420 $\mu$M, 440 $\mu$M, 460 $\mu$M, 480 $\mu$M, and 500 $\mu$M. Although doses that produce a tissue concentration of greater than 800 $\mu$M are not preferred, they can be used with some embodiments of the invention. A constant infusion of the evectins, hybrids, binding partners, or fragments thereof can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease, age of the organism, and weight or size of the organism; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Routes of administration of the pharmaceuticals of the invention include, but are not limited to, topical, transdermal, parenteral, gastrointestinal, transbronchial, and transalveolar. Transdermal administration is accomplished by application of a cream, rinse, gel, etc. capable of allowing the pharmacologically active compounds to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having the pharmacologically active compounds of this invention that are suitable for transdermal or topical administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein incorporated by reference.

Compositions having the pharmacologically active compounds of this invention that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intraderrnal, or subcutaneous injection.

Compositions having the pharmacologically active compounds of this invention that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the pharmacologically active compounds of the invention.

Compositions having the pharmacologically active compounds of this invention that are suitable for gastrointestinal administration include, but not limited to, pharmaceutically acceptable powders, pills or liquids for ingestion and suppositories for rectal administration. Due to the ease of use, gastrointestinal administration, particularly oral, is a preferred embodiment. Once the pharmaceutical comprising the evectin, hybrid, binding partner, or fragment thereof has been obtained, it can be administered to a organism in need to treat or prevent a defect in vesicle trafficking, signal transduction, G protein binding, or membrane biosynthesis and organization.

The following example describes a method that was used to discover the evectin gene family.

EXAMPLE 1

A partial cDNA clone for evt-1 was isolated in a yeast two-hybrid screen designed to discover regulatory proteins that interact with the transcription factor SCIP. A GAL4 activation domain tagged cDNA library from forskolin-stimulated, cultured rat Schwann cells was constructed in pGAD424 and screened using standard procedures (Lemke and Brockes, *J. Neurosci.*, 4:75–83 (1984) and Yeast Protocols Handbook, Clontech, both references herein incorporated by reference). Full-length rat evt-1 cDNAs (1875 bp) were then obtained from a λ Zap Schwann cell cDNA library using the two-hybrid partial cDNA fragments as probes. (Monuki et al., *Neuron*, 2:783–793 (1989), herein incorporated by reference).

Murine and human evt-1 cDNA fragments and murine evt-2 cDNA fragments were obtained as expressed sequence tag (EST) clones from the American Type Culture Collection. As one of skill will appreciate, members of the evectin family of genes can be isolated by several methods and the example above teaches only one possible approach. The following example details an approach that was used to identify the genetic loci of evt-1 and evt-2.

EXAMPLE 2

The human evt-1 and evt-2 genes were mapped through the human EST database assembly and mapping consortium. Overlapping EST sequences for evt-1 and evt-2 were assembled and assigned to an EST cluster using the EST-Assembler at TIGEMnet: http://gcg.tigem.it. (Banfi et al., *Trends Genet.*, 14:80–81 (1998), herein incorporated by reference). The EST clusters were mapped by the EST Mapping Consortium using radiation hybrids. (See the Human Transcript Map database at http://www.ncbi.nlm.nih.gov).

Evt-1 mapped to an interval within human chromosome 11q13 at 80–84 cM from the centromere, between the DNA markers D11S916 and D11S911. The interval that contains evt-1 is estimated to be ~1.2 Mb in length. Within this same interval, near marker D11S533, is the gene for an inherited retinal degeneration disorder designated autosomal dominant familial exudative vitreoretinopathy (adFEVR). (For articles on adFEVR see: Criswick and Schepens, *Am. J. Ophthalmol.*, 68:578–594 (1969); Li et al., *Am. J. Hum. Genet.*, 51:749–754 (1992); Price et al., *Ophthalmic Genet.*, 17:53–57 (1996)). Two different multipoint linkage studies, using three families, have positioned the gene for adFEVR near D11S533, which is located within this same interval. (Li et al., *Am. J. Hum. Genet.*, 51:749–754 (1992); Price et al., *Ophthalmic Genet.*, 17:53–57 (1996)).

The human evt-2 gene, on the other hand, mapped to chromosome 4ql, 50–56cM from the centromere, between D4S1587 and D4S405. This example established that aberrant expression of evt-1 (e.g., mutant varieties or abnormal levels) can be associated with adFEVR. Further, the findings described in this example demonstrate that the evectin family can encompass related molecules expressed from different chromosomes. The example below describes experiments that were performed to analyze the expression patterns of evt-1 and evt-2 in various tissues and during development.

EXAMPLE 3

A Northern blot survey of total RNAs isolated from adult mammalian tissues revealed a restricted pattern of evt-1 expression and widespread evt-2 expression. Total cellular RNAs were isolated and analyzed by RNA blot as described previously. (Monuki et al., *Neuron*, 2:783–793 (1989), herein incorporated by reference). In a first blot, total RNAs from adult mouse tissues were probed for evt-1 mRNA. A 500 bp ScaI- XhoI fragment from the 3'-end of the rat evt-1 cDNA clone was used as the probe. The approximately 1.9 kb evt-1 mRNA was expressed in rat brain, peripheral nerve, and retina but was undetectable in skeletal muscle, small intestine, spleen, liver, lung, kidney, or heart. The blot was then stripped and re-probed for evt-2 mRNA. For evt-2 probes, a 1100 bp PstI fragment from the murine EST clone W99864 was used. In contrast to the evt-1 expression pattern, the approximately 3.5 kb evt-2 mRNA was expressed in brain, retina, heart, kidney, lung, muscle, and nerve. Equal loading of the lanes was assessed by methylene blue staining of 18S and 28S rRNAs.

In a second experiment, the expression of evt mRNAs during development was investigated. A developmental Northern blot was performed on total RNAs isolated from the heads of rat embryos at embryonic day 13, 15, and 19 and from the brains of rats at postnatal day 0, 3, 17, and adult. The blot was simultaneously probed for both evt-1 and evt-2 mRNA, using the probes described above and equal loading of the lanes was assessed by methylene blue staining of 18S and 28S rRNAs. In both the brain and the sciatic nerve, evt-1 was up-regulated through the first and second postnatal weeks, during the onset of axonal myelination by oligodendrocytes (CNS) and Schwann cells (PNS). Further, expression of evt-1 mRNA was maintained at relatively high levels in the adult CNS and PNS. In contrast to the pattern of evt-1 expression, evt-2 mRNA was readily detected in the embryonic brain but expression levels decreased dramatically during the transition from postnatal day 3 to postnatal day 17, which provided evidence that expression levels of evt-1 and evt-2 shift during development.

The results presented in this example provide evidence that evt-1 expression is restricted to the CNS and PNS, whereas, evt-2 expression is more widespread. Additionally these results point out that evt-1 expression is upregulated late in development as evt-2 expression wanes. The following example describes an in situ hybridization analysis that was performed on sections of adult mouse brain.

EXAMPLE 4

In a first group of in situ hybridizations, evt-1 expression in adult CNS was evaluated. Accordingly, perfused tissues and organs were sectioned at approximately 7–10 μm. $^{35}S/^{33}P$ in situ hybridization was carried out as described. (Kilpatrick et al., *Mol. Cell Neurosci.*, 7:62–74 (1996), herein incorporated by reference). Sense and antisense riboprobes for evt-1 were transcribed in vitro. (Maxiscript, Ambion). The evt-1 riboprobe was prepared from the 3'-most 500 bp of the rat cDNA and a 700 bp PLP riboprobe (control) was made from the 3' end of the proteolipid protein cDNA.

Analysis of evt-1 expression in the adult CNS by darkfield microscopy revealed that labeling was confined to the white matter and ependyma. Every myelinated tract of the adult rat CNS was labeled by hybridization with the evt-1 probe. The labeling of white matter by the evt-1 probe coincided with white matter labeling by the control probe specific for PLP mRNA, a myelin-specific transcript. That is, in the cerebellum and elsewhere, the evt-1 signal co-localized with mRNA for proteolipid protein, the most abundant protein of CNS myelin. Strong expression was also detected in the pineal gland, in the inner segments of photoreceptors, and in the pigment epithelium.

This in situ hybridization analyses demonstrated that evt-1 mRNA is prominently expressed in oligodendrocytes, the cells that synthesize CNS myelin and the myelinating Schwann cells of peripheral nerves. In addition to myelinating glia in the CNS and PNS, the in situ hybridization analysis also revealed that evt-1 is expressed in only three other CNS regions: the retina, the ependyma, and the pineal gland. Evt-1 mRNA was readily detected in retinal tissue by Northern blot (EXAMPLE 2), however, and in the inner segment region of retinal photoreceptors by in situ hybridization, with slightly lower levels in the pigment epithelium. High evt-1 mRNA levels were also present in the ependymal cells that line the ventricles of the brain but not in cells of the choroid plexus, with which the ependyma is physically contiguous, and the pineal gland.

In another set of in situ hybridizations, the distribution of evt-2 mRNA was analyzed. Tissues were prepared as above and the evt-2 riboprobe was generated from the 5'-most 300 bp of the murine EST clone W99864. In situ hybridization analyses for evt-2 mRNA in the adult brain revealed a complementarity of expression with evt-1 in many regions. While evt-1 was confined to white matter tracts and was excluded from neuronal populations, there was widespread expression of evt-2 mRNA in neurons throughout the brain but not white matter. Dark-field microscopy also revealed widespread neuronal expression in all hippocampal fields and in overlying cortex. Further, expression of evt-2 mRNA was seen in the adult mouse pineal gland and in neurons of the underlying inferior colliculus. Strong expression of evt-2 was also detected in the choroid plexus but not in the ependyma or white matter tracts and widespread expression of evt-2 mRNA was detected in a lateral region of adult mouse neocortex but not in the underlying white matter. This example provides evidence of the complimentarity of evt-1 and evt-2 expression, however, in some tissues (e.g., pineal gland, retinal, and peripheral nerve) both mRNAs are expressed. The example below details an approach that was used to obtain an affinity purified antibody that specifically recognizes evt-1 and an experiment that determined that evt-1 is an approximately 25 kD molecule that can be post-translationally modified (e.g, phosphorylated).

EXAMPLE 5

A polyclonal antibody specific for evt-1 was prepared, affinity purified, and used to detect evt-1 in a Western blot. Accordingly, rabbit antiserum was raised against a synthetic peptide derived from the a-helical, C-terminal region of the evt-1 PH domain (residues 93 to 104) using standard procedures. (Harlow and Lane, *Antibodies: A Laboratory Manual*, Cold Spring Harbor Lab. Press, Cold Spring Harbor (1988), herein incorporated by reference). A GST-evt-1 fusion protein containing residues 1 to 111 of evt-1 was prepared and used to affinity purify the evt-1 antiserum (Quickpure kit from Sterogene).

A Western blot was then performed as follows. Total proteins from brain, heart, mammary, kidney, liver, muscle, lung, and nerve were prepared and suspended in loading buffer (3% β-mercaptoethanol, 3% SDS, 10% glycerol, 1M urea, 60 mM TRIS, pH 6.8, 0.1% Triton X-100, 0.005% bromphenol blue). The proteins were separated by 12.5% SDS-PAGE (with 10 mM β-mercaptoethanol in the resolving gel), transferred onto nitrocellulose filters, and were incubated with primary antibody for 1 hr. Immunoreactivity was detected using the ECL method (Amersham) and the affinity-purified evt-1 antibody specifically recognized a protein of approximately 25 kD in the brain and nerve samples. Under these conditions, however, two species of evt-1 were detected. That is, the evt-1 that was detected in the brain and nerve samples was a closely spaced doublet at approximately 25 kD. The presence of the doublet is consistent with differential phosphorylation and/or other post-translational modification. This example establishes that antibodies that specifically recognize evt-1 can be made and that such antibodies can be used to detect at least two forms of evt-1 in immunoassays (e.g., unphosphorylated and phosphorylated evt-1 or evt-1 lacking post-translational modification or evt-1 having post-translational modification). The example below describes experiments that were conducted to verify that the evectin family members can be membrane associated molecules.

EXAMPLE 6

Density gradient fractionation of retinal photoreceptors was performed to evaluate the ability of evt-1 to associate with membranes. This analysis was performed on photoreceptors of the frog (*Rana berlandieri*) retina because the outer segment membranes of frog photoreceptors are synthesized and shed at an exceptionally high steady-state rate, which allows for the metabolic labeling by pulse-chase of multiple rhodopsin-bearing membrane compartments. (Besharse, *The Retina: A Model for Cell Biological Studies*, Adler and Farber, eds., Academic Press, New York, 1986:297–352), herein incorporated by reference). In particular, this type of analysis allows the visualization of post-Golgi membrane vesicles, which because of their transient nature and low abundance are difficult to detect in other systems.

Accordingly, southern leopard frogs, *Rana berlandieri*, were dark-adapted for 2 hours before experiments. Isolated retinae were incubated with [$^{35}$S]-Express protein labeling mixture (25 μCi/retina) at 22° C. for 1 hour followed by 2 hours of cold chase. Retinal fractionation, purification of rod outer segments (ROS) on step sucrose gradients, and preparation of post-nuclear supernatants enriched in photoreceptor biosynthetic membranes were all performed as described previously. (Deretic and Papermaster, *J. Cell Biol.*, 113:1281–1293 (1991), herein incorporated by reference).

The post-nuclear supernatants were fractionated on linear 20–39% (w/w) sucrose gradients at 100,000 $g_{av}$ for 15 h at 4° C., and 14 fractions were collected from the top of the gradient. Six subcellular fraction pools were created as described previously (Deretic et al., *J. Biol. Chem.*, 271:279–2286 (1996), herein incorporated by reference), diluted with 10 mM Tris acetate pH 7.4 and centrifuged at 336,000×$g_{av}$ for 30 min. Pellets were resuspended in 10 mM Tris acetate pH 7.4, and supernatants were precipitated with 10% TCA and analyzed by SDS-PAGE. Purified rod outer segments were isolated from only one half of one retina, because the high rhodopsin content precluded loading more protein on SDS-PAGE. The majority of radiolabeled rhodopsin was recovered in a post-Golgi fraction and a complete absence of radiolabeled rhodopsin was found in the cytosolic fractions. A duplicate gel was blotted and probed sequentially with antibodies to evt-1 and ARF3. Immunoblotting with affinity purified anti-evt-1 (diluted 1:250), which cross-reacted with frog evt-1, and anti-ARF3 (Transduction Laboratories, diluted 1:500) was performed as described previously. (Deretic et al., *J. Biol. Chem.*, 271:279–2286 (1996)).

Fractionation of frog photoreceptors revealed a remarkable evt-1 localization. Within membrane fractions, the protein was found to be a very specific marker for the post-Golgi compartment. Indeed, the distribution of evt-1 was nearly indistinguishable from that of $^{35}$S-rhodopsin after a 1 hour $^{35}$S-methionine pulse followed by a 2 hour cold chase of isolated retinae, a labeling protocol that results in maximal visualization of rhodopsin as it transits out of the trans-Golgi network ("TGN") and then through the post-Golgi on its way to the rod outer segments ("ROS"). (See Deretic, *Electrophoresis*, 18:2537–2541 (1997) for a discussion of rhodopsin distribution in sucrose gradients, herein incorporated by reference). A modest evt-1 signal was present in fractions containing the TGN, but no evt-1 was detected in the endoplasmic reticulum ("ER") fractions or in the Golgi proper. Approximately 30–40% of membrane-bound evt-1 was present in the ROS, with 30–35% in post-Golgi membranes, and the remainder distributed in other membrane fractions, primarily the TGN. The published enzymatic activities for sialyltransferase and galactosyltransferase, which are established markers for the TGN and the Golgi, present in fractions from identically run sucrose gradients of frog retinal membranes were compared to the fractions obtained above as controls. (See Deretic and Papermaster, *J. Cell Biol.*, 113:1281–1293 (1991) and Deretic and Papermaster, *J. Cell Sci.*, 106:803–813 (1993) for a discussion of sialyltransferase and galactosyltransferase distribution in sucrose gradients, herein incorporated by reference).

A fraction of photoreceptor evt-1 (~10%) was soluble and appeared in supernatants from a subset of sucrose gradient spins. Only very low levels of the protein were detected in the first fraction of the supernatant, which represents true soluble proteins. Instead, evt-1 appeared predominantly in the second and third pools of supernatants (the supernatants from the pellets that yielded membrane fractions), which contain proteins that are either part of large cytosolic complexes or are loosely associated with membranes that sediment in these fractions and are then eluted after membranes are diluted from sucrose and sedimented at high speed. The evt-1 membrane and supernatant profiles were particularly informative when compared with those of a soluble protein that lacks a hydrophobic membrane anchor but which nonetheless reversibly associates with membranes. Among such proteins are ADP ribosylation factors, or "ARF proteins", which are important in membrane trafficking and vesicular processing. (See Boman and Kahn, *Trends Biochem. Sci.*, 20:147–150 (1995) for a discussion of ARF proteins). The membrane-bound form of one of these proteins (ARF3) was primarily associated with the Golgi complex and the TGN, and was not detected in evt-1$^+$ post-Golgi membranes. Note that soluble ARF3 appeared primarily in supernatent fraction 1, whereas soluble evt-1 appeared in supernatant fractions 2 and 3. Taken together, the data above provide evidence that evt-1 is specifically recruited to cellular membranes in the late TGN and, most prominently, in the post-Golgi compartment of vertebrate photoreceptors. The data above also establish that evt family members are the first identified proteins having a pleckstrin homology domain that can directly associate with membranes without an interaction with another protein (e.g., without an interaction with PIP2). The example below provides several methods of making a membrane-bound evectin, which can be used to transfer an evectin to the surface of a cell.

EXAMPLE 7

A membrane bound evectin (e.g., evt-1 or evt-2) can be made by employing conventional techniques in liposome engineering. By one approach, purified evectin is reconstituted into either soybean phosphatidylcholine ("PC") vesicles or into vesicles of defined lipid composition so as to create a synthetic lipid vesicle-bound evectin, also called a "SLV-bound evectin". Purified lipids and soybean PC (~20% phosphatidylcholine) can be obtained from SIGMA. To form synthetic lipid vesicles or "SLVs", the required amounts of lipid in chloroform are dried under a stream of nitrogen, resuspended in 10 mM Tris-HCl, pH7.2, 100 mM NaCl by vortexing, and sonicated with a microtip sonicator. Purified evectin is reconstituted into SLVs by conventional techniques. (Cerione et al., *Nature,* 306:562 (1983), herein incorporated by reference). The evectin-containing vesicles are suspended in 20 mM Tris-HCl, pH 7.5 and the concentration of evectin on the vesicle can be determined by binding of a radiolabeled antibody (e.g., the antibody prepared in example 3).

By another approach, SLV formulations that mimic the cytoplasmic surface of plasma membranes of eukaryotic cells are created and used to incorporate evectins. Accordingly, saturating amounts of evectin (e.g., 0.6 nmol protein/μmol lipid) are contacted with SLVs and the soluble evectin content of the evt-SLV buffer is measured after pelleting of the SLV by ultracentrifugation. A titration of the amount of dipalmitoyl phosphatidylserine (PS) content of SLVs (e.g., an increase in 1% increments) can be performed so as to identify the amount of PS that provides for an optimal incorporation of evectin. Additionally, SLVs containing various concentrations of PS can be contacted with increasing concentrations of evectin to determine the amount of evectin required to saturate an SLV. SLVs having evectins can also be created using artificial ceramides that mimic natural ceramides. In the next example, several methods of making proteins are provided.

EXAMPLE 8

The following is provided as one possible method to express the proteins encoded by the nucleic acids of the invention. First, the methionine initiation codon for an evectin and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the nucleic acid lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). The vector pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding the polypeptide to be expressed can be obtained by PCR from the bacterial vector using oligonucleotide primers complementary to the nucleic acid and containing restriction endonuclease sequences for Pst I incorporated into the 5'primer and BglII at the 5' end of the corresponding cDNA 3' primer, taking care to ensure that the nucleic acid is positioned in frame with the poly A signal. The purified fragment obtained from the resulting PCR reaction is digested with PstI, blunt ended with an exonuclease, digested with Bgl II, purified and ligated to pXT1, now containing a poly A signal and digested with BglII. The ligated product is transfected into a suitable cell line using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). Preferably the expressed protein is released into the culture medium, thereby facilitating purification.

Another embodiment utilizes the "Xpress system for expression and purification" (Invitrogen, San Diego, Calif.). The Xpress system is designed for high-level production and purification of recombinant proteins from bacterial, mammalian, and insect cells. The Xpress vectors produce recombinant proteins fused to a short N-terminal leader peptide that has a high affinity for divalent cations. Using a nickel-chelating resin (Invitrogen), the recombinant protein can be purified in one step and the leader can be subsequently removed by cleavage with enterokinase.

One preferred vector for the expression of evectin and fragments of evectin is the pBlueBacHis2 Xpress. The pBlueBacHis2 Xpress vector is a Baculovirus expression vector containing a multiple cloning site, an ampicillin resistance gene, and a lac z gene. By one approach, the evectin nucleic acid, or portion thereof is cloned into the pBlueBacHis2 Xpress vector and SF9 cells are infected. The expression protein is then isolated or purified according to the manufacturer's instructions. Several other cultured cell lines having recombinant constructs or vectors comprising evectin or portions thereof are embodiments of the invention and their manufacture would be routine given the present disclosure.

Proteins in the culture medium can be separated and isolated by gel electrophoresis. The separated proteins can be detected using techniques such as Coomassie or silver staining or by using antibodies against the protein. Coomassie, silver staining, and immunolabeling of proteins are techniques familiar to those skilled in the art. If desired, the proteins can also be ammonium sulfate precipitated or separated based on size or charge prior to electrophoresis. The evectin protein or portion thereof can also be purified using standard immunochromatography techniques. In such procedures, a solution containing the protein, such as the culture medium or a cell extract, is applied to a column having antibodies against the protein attached to the chromatography matrix. The protein is allowed to bind the immunochromatography column. Thereafter, the column is washed to remove non-specifically bound proteins. The specifically bound protein is then released from the column and recovered using standard techniques.

Further, evectin or a portion thereof can be incorporated into expression vectors designed for use in purification schemes employing chimeric polypeptides. In such strategies, the coding sequence of an evectin nucleic acid or portion thereof is inserted in frame with the gene encoding the other half of the chimera. The other half of the chimera can be β-globin or a nickel binding polypeptide encoding sequence. A chromatography matrix having antibody to β-globin or nickel attached thereto is then used to purify the chimeric protein. Protease cleavage sites can be engineered between the β-globin gene or the nickel binding polypeptide and the evectin cDNA such as enterokinase. Thus, the two polypeptides of the chimera can be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (*Basic Methods in Molecular Biology*, L. G. Davis, M. D. Dibner, and J. F. Battey, ed., Elsevier Press, NY, 1986) and many of the methods are available from Stratagene, Life Technologies, Inc., or Promega. Polypeptide can additionally be produced from the construct using in vitro translation systems, such as the In vitro Express™ Translation Kit (Stratagene). In the next example, an aproach to make an evt-1 knockout mouse is provided.

EXAMPLE 9

Using a full-length rat cDNA (10p) obtained from a λZap Schwann cell cDNA library, we screened a λDash II 129sv mouse genomic library. Four unique, overlapping phage clones were isolated, subcloned, and mapped with restriction enzymes. One phage clone (2.3), contained all eight coding exons including the alternatively-spliced exon 6.

Figure 5:
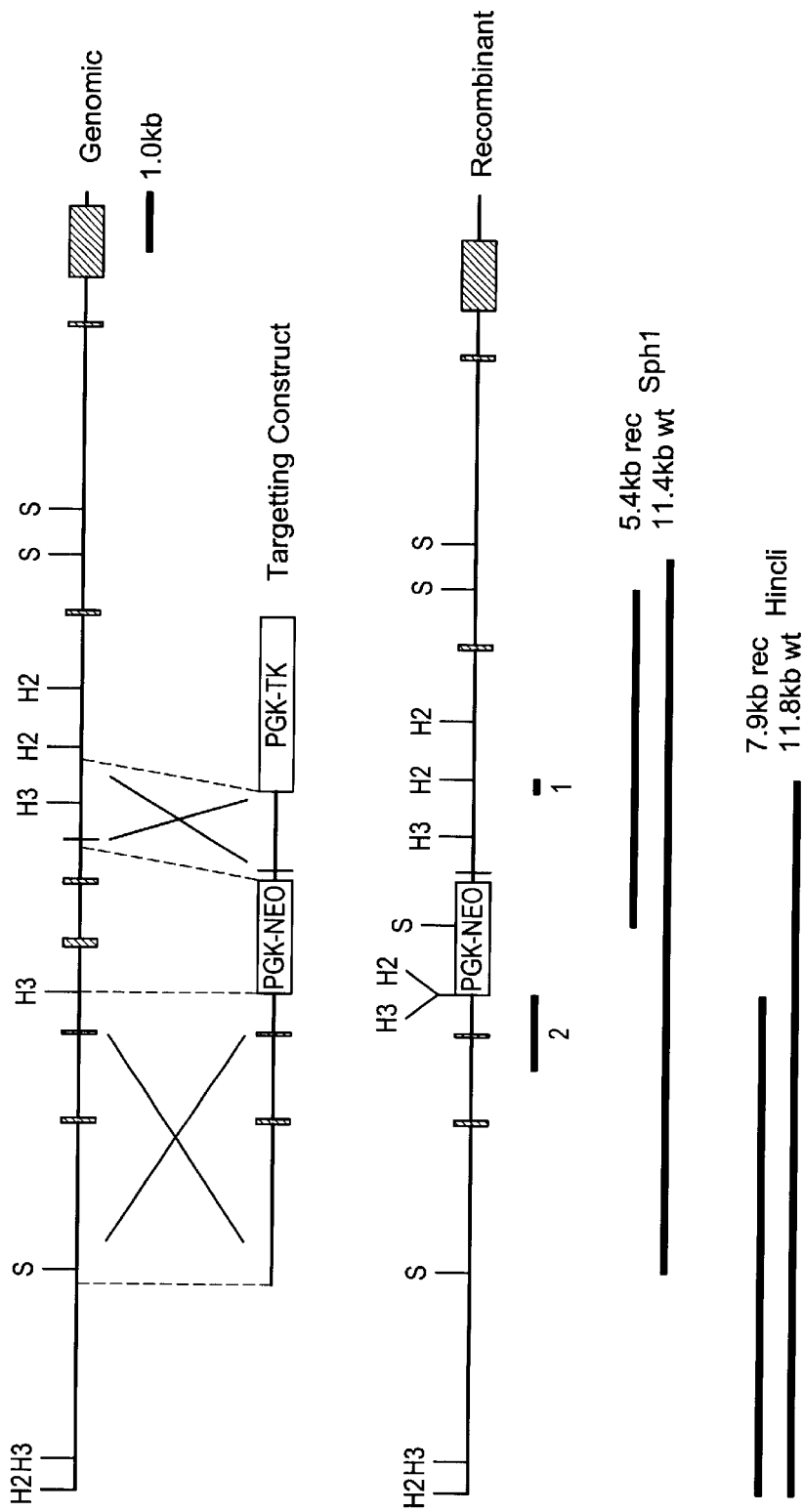
FIG. 5 illustrates the strategy that was used to create evt-1 knockout mice.

A knockout targeting vector was constructed using the pPNT vector backbone containing a neomycin resistance gene and a HSV thymidine kinase gene. (See FIG. 5) A 4.4 kb genomic fragment extending from the 5' end of phage clone 2.3 to a HindIII site and containing exons 1 and 2 was cloned into the vector backbone 5' of the neo gene as the long arm. A 1.5 kb genomic BamHI-BamHI fragment containing exon 5 was cloned into the vector backbone 3' of the neo gene as the short arm. The targeting construct was electroporated into W95 mouse embryonic stem cells. The stem cells were grown on embryonic fibroblast cells containing the neo gene and in media containing Leukocyte Inhibitory Factor (LIF) at 25 units/ml. The electroporated stem cells were selected using G418 (200–300 µg/ml) and FIAU in supplemented DMEM.

Homologous recombination of the targeting construct into the genomic DNA of the cell resulted in the substitution of the 1.8 kb neo cassette for the endogenous 2.5 kb genomic sequence containing exons 3 and 4. Individual stem cell colonies were isolated and screened by Southern analysis. In brief, two independent screening paradigms were utilized: 1) The genomic DNA from the cell lines was digested with the restriction enzyme HincII and probed with a labelled 1.2 kb BamHI-HindIII fragment in the 3' end of the long arm resulting in a 11.8 kb wildtype band and a 7.9 kb recombinant band, 2) the genomic DNA was digested with the restriction enzyme SphI and probed with a labelled 250 bp BamHI-BamHI fragment, located just 3' of the short arm resulting in a 11.4 kb wildtype band and a 5.4 kb mutant band. Of 220 colonies analyzed over 4 different electroporations, 2 clones (F3, F7) gave a recombinant restriction pattern. The two clones were expanded and injected into C57/BL6 blastocysts, which were subsequently implanted into pseudopregnant foster matters. Seven foster matters were implanted and yielded 54 chimeric pups. Of the 54 chimeric pups, 50 were high-chimeric males (as defined by >90% agouti coat color). Ten of the chimeric males, five from clone F3 and five from clone F7, were mated to C57BL/6 females which resulted in germline transmission of the mutant evt-1 allele in 6 out of 10 males. Mice heterozygous for the mutant allele were mated to each other to produce litters containing progeny that were homozygous for the disrupted evt-1 locus.

Using standard procedures, brain tissue from 2 month old wildtype evt-1 +/+, heterozygous evt-1 +/−, and homozygous evt-1 −/− littermates were processed for total RNA and total protein. The genotypes of the mice were confirmed by Southern analysis. Expression of evt-1 RNA was analyzed by Northern blot analysis using a 500 bp ScaI-XhoI fragment from the evt-1 rat cDNA as the probe. While the wildtype +/+ and heterozygous +/− mice both retained the 1.9 kb mRNA signal, homozygous evt-1 −/− animals lost all expression of an evt-1 message.

In another experiment, protein extracts from brain tissue were analyzed for the presence of evt-1 protein. After separating the protein samples by SDS-PAGE, a Western blot using an anti-evt-1 antibody was performed. Accordingly, wildtype +/+ and heterozygous evt-1 +/− mice were found to retain the 23–25 kD doublet signal, whereas the evt-1 −/− mice failed to express evt-1 . Thus, both types of analyses, one at the level of RNA and one at the level of protein, confirmed the loss of function of the evt-1 gene. Next, the phenotype of the evt-1 knockout mice was characterized. Phenotypic analysis of evt-1 −/− mutant mice focused on the peripheral nervous system and, more specifically, the regulation of function in peripheral nerves, like the sciatic nerve. Transmission electron microscopy was used to analyze the ultrastructure of sciatic nerves in cross-section. Intact sciatic nerves from 2 month old wildtype evt-1 +/+ and homozygous evt-1 −/− littermates were fixed and dissected. After processing and embedding the samples in epoxy resin, thin sections were cut using an ultramicrotome and viewed under a transmission electron microscope. Cross-sectional fields viewed at a magnification of 7200x showed clusters of small, unmyelinated axons enveloped by the cytoplasm of individual Schwann cells. In the case of a wildtype +/+ nerve, the adjacent small axons are buffered from their neighbors by the interpositioning of Schwann cell cytoplasm. In evt-1 −/− nerves, a loss of this buffer zone was observed and several examples of touching of the membranes from adjacent axons were seen. The findings presented in this example establish that an evt-1 knockout mouse can be created and that such mice exhibit a phenotype characterized by a lack of buffer zone between small axons.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A purified or isolated nucleic acid encoding a polypeptide having a pleckstrin homology domain and a hydrophobic membrane-binding domain, wherein said nucleic acid selected from the group consisting of: SEQ. ID. NO: 1, SEQ. ID. NO: 2, SEQ. ID. NO: 3, SEQ. ID. NO: 4, SEQ. ID. NO: 5, SEQ. ID. NO: 11, and SEQ. ID. NO: 12 or a sequence complementary thereto.

2. A purified or isolated nucleic acid sequence encoding a polypeptide having an amino acid sequence selected from the group consisting of: SEQ ID NO: 6, SEQ ID NO: 7, SEQ ID NO: 8, SEQ ID NO: 9 and SEQ ID NO: 10.

3. The nucleic acid sequence of claim 2, wherein said sequence is selected from the group consisting of: SEQ. ID. NO: 1, SEQ. ID. NO: 2, SEQ ID NO: 3, SEQ. ID. NO: 4, SEQ. ID. NO: 5, SEQ. ID. NO.11, and SEQ. ID. NO. 12.

* * * * *

SEQUENCE LISTING

```
<160> NUMBER OF SEQ ID NOS: 17

<210> SEQ ID NO 1
<211> LENGTH: 672
<212> TYPE: DNA
<213> ORGANISM: Rattus
<220> FEATURE:
<221> NAME/KEY: CDS
<222> LOCATION: (1)...(672)

<400> SEQUENCE: 1 atg gcc ctg gtg agg ggc ggc tgg cta tgg aga cag agc tcc atc ctc        48
Met Ala Leu Val Arg Gly Gly Trp Leu Trp Arg Gln Ser Ser Ile Leu
  1               5                  10                  15 cgc cgc tgg aag cgg aat tgg ttt gct ctg tgg ttg gat ggc acg ctg        96
Arg Arg Trp Lys Arg Asn Trp Phe Ala Leu Trp Leu Asp Gly Thr Leu
             20                  25                  30
```

```
ggt tac tac cac gat gag acg gca cag gac gag gag gac cgt gta gtt    144
Gly Tyr Tyr His Asp Glu Thr Ala Gln Asp Glu Glu Asp Arg Val Val
         35                  40                  45 atc cac ttc aat gtc cga gac ata aag gtc ggc cag gag tgt cag gat    192
Ile His Phe Asn Val Arg Asp Ile Lys Val Gly Gln Glu Cys Gln Asp
 50                  55                  60 gtg cag ccc cca gag ggc agg agc cga gat ggc ctg ctg aca gtg aac    240
Val Gln Pro Pro Glu Gly Arg Ser Arg Asp Gly Leu Leu Thr Val Asn
 65                  70                  75                  80 cta cgg gag ggt tcc cgc ctg cac ctg tgc gca gag acc cgg gat gat    288
Leu Arg Glu Gly Ser Arg Leu His Leu Cys Ala Glu Thr Arg Asp Asp
                 85                  90                  95 gcc ata gca tgg aag aca gcc ctg atg gag gca aac tcc acc ccg gcc    336
Ala Ile Ala Trp Lys Thr Ala Leu Met Glu Ala Asn Ser Thr Pro Ala
             100                 105                 110 cca gct gga gcc acc gtc cca ccc agg agc cgt cgg gtt tgc cct aag    384
Pro Ala Gly Ala Thr Val Pro Pro Arg Ser Arg Arg Val Cys Pro Lys
         115                 120                 125 gtc agg tgt acg agc ctc tca tgg aag ccc tgt aag gtt gag agg cgg    432
Val Arg Cys Thr Ser Leu Ser Trp Lys Pro Cys Lys Val Glu Arg Arg
 130                 135                 140 atc tgg gta cgc gtc tac agt cca tat caa gac tac tat gag gtg gta    480
Ile Trp Val Arg Val Tyr Ser Pro Tyr Gln Asp Tyr Tyr Glu Val Val
145                 150                 155                 160 ccc ccc aac gca cac gag gcc acg tat gtc cgc agc tac tat ggg cca    528
Pro Pro Asn Ala His Glu Ala Thr Tyr Val Arg Ser Tyr Tyr Gly Pro
                165                 170                 175 cct tat ggt cct ggt gtg aca cat gtg atc gtg cga gag gat ccc tgc    576
Pro Tyr Gly Pro Gly Val Thr His Val Ile Val Arg Glu Asp Pro Cys
            180                 185                 190 tac agc tct ggc gcc cct ttg gcc atg ggc atg ctt gct ggg gct gcc    624
Tyr Ser Ser Gly Ala Pro Leu Ala Met Gly Met Leu Ala Gly Ala Ala
        195                 200                 205 acg ggt gct gcc ctt ggc tca ctt atg tgg tcg cct tgc tgg ttc tga    672
Thr Gly Ala Ala Leu Gly Ser Leu Met Trp Ser Pro Cys Trp Phe *
    210                 215                 220
```

<210> SEQ ID NO 2
<211> LENGTH: 672
<212> TYPE: DNA
<213> ORGANISM: Murine
<220> FEATURE:
<221> NAME/KEY: CDS
<222> LOCATION: (1)...(672)

<400> SEQUENCE: 2

```
atg gcc ctg gtg agg ggc ggc tgg ctg tgg aga cag agc tcc atc ctc     48
Met Ala Leu Val Arg Gly Gly Trp Leu Trp Arg Gln Ser Ser Ile Leu
 1               5                  10                  15 cgc cgc tgg aag cgg aat tgg ttc gct ctg tgg ttg gat ggc acg ctg     96
Arg Arg Trp Lys Arg Asn Trp Phe Ala Leu Trp Leu Asp Gly Thr Leu
             20                  25                  30 ggt tac tac cat gac gag acg gca cag gac gag gag gac cga gta gtc    144
Gly Tyr Tyr His Asp Glu Thr Ala Gln Asp Glu Glu Asp Arg Val Val
         35                  40                  45 atc cac ttc aat gtc cga cac ata aag gtc ggc caa gag tgt cag gat    192
Ile His Phe Asn Val Arg His Ile Lys Val Gly Gln Glu Cys Gln Asp
 50                  55                  60 gtg cag ccc cca gag ggc agg agc cga gat ggc ctg ctg aca gtg aac    240
Val Gln Pro Pro Glu Gly Arg Ser Arg Asp Gly Leu Leu Thr Val Asn
 65                  70                  75                  80
```

-continued

```
ctg cgg gag ggt tcc cgc ctg cac ctg tgc gct gag acc cgg gat gat    288
Leu Arg Glu Gly Ser Arg Leu His Leu Cys Ala Glu Thr Arg Asp Asp
            85                  90                  95 gcc ata gca tgg aag act gcc ctg atg gag gca aat tcc acc ccg gcc    336
Ala Ile Ala Trp Lys Thr Ala Leu Met Glu Ala Asn Ser Thr Pro Ala
        100                 105                 110 cca gct gga gcc acc gtc cca ccc agg agc cgt cgg gtt tgc cct aag    384
Pro Ala Gly Ala Thr Val Pro Pro Arg Ser Arg Arg Val Cys Pro Lys
    115                 120                 125 gtc agg tgt acg acc ctc tca tgg aac ccc tgt aag gtt gag aag cgg    432
Val Arg Cys Thr Thr Leu Ser Trp Asn Pro Cys Lys Val Glu Lys Arg
130                 135                 140 atc tgg gta cgc gtc tac agc cca tat cag gac tac tat gag gtg gtg    480
Ile Trp Val Arg Val Tyr Ser Pro Tyr Gln Asp Tyr Tyr Glu Val Val
145                 150                 155                 160 cca ccc aac gca cat gaa gcc aca tat gtc cgc agc tac tat ggg cca    528
Pro Pro Asn Ala His Glu Ala Thr Tyr Val Arg Ser Tyr Tyr Gly Pro
                165                 170                 175 cct tat ggt cct ggt gtg aca cac gtg ata gtt cga gag gac ccc tgc    576
Pro Tyr Gly Pro Gly Val Thr His Val Ile Val Arg Glu Asp Pro Cys
            180                 185                 190 tac agc tca gga gcc cct ttg gcc atg ggc atg ctt gct ggg gct gcc    624
Tyr Ser Ser Gly Ala Pro Leu Ala Met Gly Met Leu Ala Gly Ala Ala
        195                 200                 205 acg ggt gct gct ctt ggt tca ctt atg tgg tcg cct tgt tgg ttc tga    672
Thr Gly Ala Ala Leu Gly Ser Leu Met Trp Ser Pro Cys Trp Phe *
    210                 215                 220

<210> SEQ ID NO 3
<211> LENGTH: 675
<212> TYPE: DNA
<213> ORGANISM: Homo Sapien
<220> FEATURE:
<221> NAME/KEY: CDS
<222> LOCATION: (1)...(675)

<400> SEQUENCE: 3 atg gcc ctg gtg agg ggc ggc tgg ctg tgg aga cag agc tcc atc ctc     48
Met Ala Leu Val Arg Gly Gly Trp Leu Trp Arg Gln Ser Ser Ile Leu
1               5                   10                  15 cgc cgc tgg aag cgg aac tgg ttt gcc ctg tgg ctg gac ggg acc ctg     96
Arg Arg Trp Lys Arg Asn Trp Phe Ala Leu Trp Leu Asp Gly Thr Leu
            20                  25                  30 gga tac tac cac gat gag aca gcg cag gac gag gag gac cgt gtg ctc    144
Gly Tyr Tyr His Asp Glu Thr Ala Gln Asp Glu Glu Asp Arg Val Leu
        35                  40                  45 atc cac ttc aat gtc cgt gac ata aag atc ggc cca gag tgc cat gat    192
Ile His Phe Asn Val Arg Asp Ile Lys Ile Gly Pro Glu Cys His Asp
    50                  55                  60 gtg cag ccc cca gag ggc cgg agc cga gat ggc ctg ctg act gtg aac    240
Val Gln Pro Pro Glu Gly Arg Ser Arg Asp Gly Leu Leu Thr Val Asn
65                  70                  75                  80 cta cgg gaa ggc ggc cgc ctg cac ctc tgt gcg gag acc aag gat gat    288
Leu Arg Glu Gly Gly Arg Leu His Leu Cys Ala Glu Thr Lys Asp Asp
                85                  90                  95 gcc cta gca tgg aag aca gca ctg ctg gag gca aac tcc acc ccg gcc    336
Ala Leu Ala Trp Lys Thr Ala Leu Leu Glu Ala Asn Ser Thr Pro Ala
            100                 105                 110 cca gct gga gcc acc gtc cct ccc agg agc cgc cgg gtt tgc tcc aag    384
Pro Ala Gly Ala Thr Val Pro Pro Arg Ser Arg Arg Val Cys Ser Lys
        115                 120                 125
```

```
gtc agg tgt gtg acc cgc tcg tgg agc ccc tgt aag gtt gag agg cgg      432
Val Arg Cys Val Thr Arg Ser Trp Ser Pro Cys Lys Val Glu Arg Arg
    130                 135                 140 atc tgg gtg cgc gtc tac agc ccg tac caa gac tac tac gag gtg gtg      480
Ile Trp Val Arg Val Tyr Ser Pro Tyr Gln Asp Tyr Tyr Glu Val Val
145                 150                 155                 160 ccc ccc aat gca cac gag gcc acg tat gtc cgc agc tac tac gga ccg      528
Pro Pro Asn Ala His Glu Ala Thr Tyr Val Arg Ser Tyr Tyr Gly Pro
                165                 170                 175 ccc tac gca ggc cct ggc gtg acg cac gtg ata gtg cgg gag gat ccc      576
Pro Tyr Ala Gly Pro Gly Val Thr His Val Ile Val Arg Glu Asp Pro
        180                 185                 190 tgc tac agc gcc ggc gcc cct ctg gcc atg ggc atg ctt gcg gga gcc      624
Cys Tyr Ser Ala Gly Ala Pro Leu Ala Met Gly Met Leu Ala Gly Ala
            195                 200                 205 gcc act ggg gcg gcg ctg ggc tcg ctc atg tgg tcg ccc tgc tgg ttc      672
Ala Thr Gly Ala Ala Leu Gly Ser Leu Met Trp Ser Pro Cys Trp Phe
        210                 215                 220 tga                                                                  675
 *
```

<210> SEQ ID NO 4
<211> LENGTH: 666
<212> TYPE: DNA
<213> ORGANISM: Murine
<220> FEATURE:
<221> NAME/KEY: CDS
<222> LOCATION: (1)...(666)

<400> SEQUENCE: 4

```
atg gcg ttc gtg aag agt gga tgg tta ctt cgg cag agc acc att ctg       48
Met Ala Phe Val Lys Ser Gly Trp Leu Leu Arg Gln Ser Thr Ile Leu
  1               5                  10                  15 aaa cgc tgg aag aag aat tgg ttc gac ctg tgg tca gac ggt cac ctg       96
Lys Arg Trp Lys Lys Asn Trp Phe Asp Leu Trp Ser Asp Gly His Leu
                 20                  25                  30 atc tac tac gat gat cag act cgg cag agc ata gag gat aag gtc cac      144
Ile Tyr Tyr Asp Asp Gln Thr Arg Gln Ser Ile Glu Asp Lys Val His
             35                  40                  45 atg ccc gtg gac tgc atc aat atc cgc acg ggg cat gag tgc cgg gac      192
Met Pro Val Asp Cys Ile Asn Ile Arg Thr Gly His Glu Cys Arg Asp
 50                  55                  60 atc cag cct cca gat ggg aag ccc aga gac tgt ctg ctg cag atc gtt      240
Ile Gln Pro Pro Asp Gly Lys Pro Arg Asp Cys Leu Leu Gln Ile Val
 65                  70                  75                  80 tgc cga gac ggg aag acc atc agt ctc tgt gca gag agc aca gac gat      288
Cys Arg Asp Gly Lys Thr Ile Ser Leu Cys Ala Glu Ser Thr Asp Asp
                 85                  90                  95 tgc ctg gca tgg aag ttt aca ctg cag gat tcc aga aca aac aca gct      336
Cys Leu Ala Trp Lys Phe Thr Leu Gln Asp Ser Arg Thr Asn Thr Ala
            100                 105                 110 tac gtt ggt tca gca atc ctg tct gaa gag act gca gtg gcc gcg tcc      384
Tyr Val Gly Ser Ala Ile Leu Ser Glu Glu Thr Ala Val Ala Ala Ser
        115                 120                 125 ccg cct ccc tac gca gcc tat gct aca cca acc cct gag gtc tac ggc      432
Pro Pro Pro Tyr Ala Ala Tyr Ala Thr Pro Thr Pro Glu Val Tyr Gly
    130                 135                 140 tat ggt cca tac agc ggc gca tac ccc gca gga act caa gtt gtc tat      480
Tyr Gly Pro Tyr Ser Gly Ala Tyr Pro Ala Gly Thr Gln Val Val Tyr
145                 150                 155                 160
```

```
gcc gcc aac ggg cag gca tat gca gtg cca tac cag tac ccg tat gca        528
Ala Ala Asn Gly Gln Ala Tyr Ala Val Pro Tyr Gln Tyr Pro Tyr Ala
            165                 170                 175 gga gtt tat gga caa cag cct gcc aac caa gtc atc atc cgc gag cgg        576
Gly Val Tyr Gly Gln Gln Pro Ala Asn Gln Val Ile Ile Arg Glu Arg
        180                 185                 190 tac cga gac aat gac agt gac ctg gct ctg ggc atg ctc gcc ggg gca        624
Tyr Arg Asp Asn Asp Ser Asp Leu Ala Leu Gly Met Leu Ala Gly Ala
    195                 200                 205 gcc acc ggc atg gcc ctg ggc tct ctg ttc tgg gtc ttc tag                666
Ala Thr Gly Met Ala Leu Gly Ser Leu Phe Trp Val Phe  *
210                 215                 220

<210> SEQ ID NO 5
<211> LENGTH: 666
<212> TYPE: DNA
<213> ORGANISM: Homo Sapien
<220> FEATURE:
<221> NAME/KEY: CDS
<222> LOCATION: (1)...(666)

<400> SEQUENCE: 5 atg gcg ttt gtg aag agt ggc tgg ttg ctg cga cag agt act att ttg         48
Met Ala Phe Val Lys Ser Gly Trp Leu Leu Arg Gln Ser Thr Ile Leu
1               5                   10                  15 aag cgc tgg aag aag aac tgg ttt gat ctg tgg tcg gat ggt cac ctg         96
Lys Arg Trp Lys Lys Asn Trp Phe Asp Leu Trp Ser Asp Gly His Leu
            20                  25                  30 atc tat tat gat gac cag act cgg cag aat atc gag gat aag gtc cac        144
Ile Tyr Tyr Asp Asp Gln Thr Arg Gln Asn Ile Glu Asp Lys Val His
        35                  40                  45 atg cca atg gac tgc atc aac atc cgc acg ggg cag gaa tgt cgg gat        192
Met Pro Met Asp Cys Ile Asn Ile Arg Thr Gly Gln Glu Cys Arg Asp
    50                  55                  60 act cag ccc ccg gat gga aag tca aaa gac tgc atg ctc cag att gtt        240
Thr Gln Pro Pro Asp Gly Lys Ser Lys Asp Cys Met Leu Gln Ile Val
65                  70                  75                  80 tgt cga gat ggg aaa aca att agt ctt tgt gca gaa agc aca gat gat        288
Cys Arg Asp Gly Lys Thr Ile Ser Leu Cys Ala Glu Ser Thr Asp Asp
                85                  90                  95 tgc ttg gcc tgg aaa ttt aca ctc caa gat tct agg aca aac aca gcg        336
Cys Leu Ala Trp Lys Phe Thr Leu Gln Asp Ser Arg Thr Asn Thr Ala
            100                 105                 110 tat gtg ggc tct gca gtc atg acc gat gag aca tcc gtg gtt tcc tca        384
Tyr Val Gly Ser Ala Val Met Thr Asp Glu Thr Ser Val Val Ser Ser
        115                 120                 125 cct cca cca tac acg gcc tat gct gca ccg gcc cct gag gct tat ggc        432
Pro Pro Pro Tyr Thr Ala Tyr Ala Ala Pro Ala Pro Glu Ala Tyr Gly
    130                 135                 140 tat ggg cca tac ggt ggt cgt acc cgc cag gaa ctc aag ttg tct acg        480
Tyr Gly Pro Tyr Gly Gly Arg Thr Arg Gln Glu Leu Lys Leu Ser Thr
145                 150                 155                 160 ctg cga atg ggc atg cgt atg ccg tgc cct acc agt acc cat atg cag        528
Leu Arg Met Gly Met Arg Met Pro Cys Pro Thr Ser Thr His Met Gln
                165                 170                 175 gac ttt atg gac agc agc ctg cta acc aag tca tca ttc gag agc gct        576
Asp Phe Met Asp Ser Ser Leu Leu Thr Lys Ser Ser Phe Glu Ser Ala
            180                 185                 190 atc gag aca acg aca gcg acc tgg cac tgg gca tgc tgg cag gag tca        624
Ile Glu Thr Thr Thr Ala Thr Trp His Trp Ala Cys Trp Gln Glu Ser
        195                 200                 205
```

```
gcc acg ggc atg gcc tta ggg tct cta ttt tgg gtc ttc tag         666
Ala Thr Gly Met Ala Leu Gly Ser Leu Phe Trp Val Phe *
    210             215                 220
```

<210> SEQ ID NO 6
<211> LENGTH: 223
<212> TYPE: PRT
<213> ORGANISM: Rattus

<400> SEQUENCE: 6

```
Met Ala Leu Val Arg Gly Gly Trp Leu Trp Arg Gln Ser Ser Ile Leu
 1               5                  10                  15

Arg Arg Trp Lys Arg Asn Trp Phe Ala Leu Trp Leu Asp Gly Thr Leu
            20                  25                  30

Gly Tyr Tyr His Asp Glu Thr Ala Gln Asp Glu Asp Arg Val Val
        35                  40                  45

Ile His Phe Asn Val Arg Asp Ile Lys Val Gly Gln Glu Cys Gln Asp
    50                  55                  60

Val Gln Pro Pro Glu Gly Arg Ser Arg Asp Gly Leu Leu Thr Val Asn
65                  70                  75                  80

Leu Arg Glu Gly Ser Arg Leu His Leu Cys Ala Glu Thr Arg Asp Asp
                85                  90                  95

Ala Ile Ala Trp Lys Thr Ala Leu Met Glu Ala Asn Ser Thr Pro Ala
            100                 105                 110

Pro Ala Gly Ala Thr Val Pro Pro Arg Ser Arg Val Cys Pro Lys
        115                 120                 125

Val Arg Cys Thr Ser Leu Ser Trp Lys Pro Cys Lys Val Glu Arg Arg
130                 135                 140

Ile Trp Val Arg Val Tyr Ser Pro Tyr Gln Asp Tyr Tyr Glu Val Val
145                 150                 155                 160

Pro Pro Asn Ala His Glu Ala Thr Tyr Val Arg Ser Tyr Tyr Gly Pro
                165                 170                 175

Pro Tyr Gly Pro Gly Val Thr His Val Ile Val Arg Glu Asp Pro Cys
            180                 185                 190

Tyr Ser Ser Gly Ala Pro Leu Ala Met Gly Met Leu Ala Gly Ala Ala
        195                 200                 205

Thr Gly Ala Ala Leu Gly Ser Leu Met Trp Ser Pro Cys Trp Phe
    210                 215                 220
```

<210> SEQ ID NO 7
<211> LENGTH: 223
<212> TYPE: PRT
<213> ORGANISM: Murine

<400> SEQUENCE: 7

```
Met Ala Leu Val Arg Gly Gly Trp Leu Trp Arg Gln Ser Ser Ile Leu
 1               5                  10                  15

Arg Arg Trp Lys Arg Asn Trp Phe Ala Leu Trp Leu Asp Gly Thr Leu
            20                  25                  30

Gly Tyr Tyr His Asp Glu Thr Ala Gln Asp Glu Asp Arg Val Val
        35                  40                  45

Ile His Phe Asn Val Arg His Ile Lys Val Gly Gln Glu Cys Gln Asp
    50                  55                  60

Val Gln Pro Pro Glu Gly Arg Ser Arg Asp Gly Leu Leu Thr Val Asn
65                  70                  75                  80

Leu Arg Glu Gly Ser Arg Leu His Leu Cys Ala Glu Thr Arg Asp Asp
                85                  90                  95
```

```
Ala Ile Ala Trp Lys Thr Ala Leu Met Glu Ala Asn Ser Thr Pro Ala
            100                 105                 110

Pro Ala Gly Ala Thr Val Pro Pro Arg Ser Arg Arg Val Cys Pro Lys
            115                 120                 125

Val Arg Cys Thr Thr Leu Ser Trp Asn Pro Cys Lys Val Glu Lys Arg
130                 135                 140

Ile Trp Val Arg Val Tyr Ser Pro Tyr Gln Asp Tyr Tyr Glu Val Val
145                 150                 155                 160

Pro Pro Asn Ala His Glu Ala Thr Tyr Val Arg Ser Tyr Tyr Gly Pro
            165                 170                 175

Pro Tyr Gly Pro Gly Val Thr His Val Ile Val Arg Glu Asp Pro Cys
            180                 185                 190

Tyr Ser Ser Gly Ala Pro Leu Ala Met Gly Met Leu Ala Gly Ala Ala
            195                 200                 205

Thr Gly Ala Ala Leu Gly Ser Leu Met Trp Ser Pro Cys Trp Phe
            210                 215                 220
```

<210> SEQ ID NO 8
<211> LENGTH: 224
<212> TYPE: PRT
<213> ORGANISM: Homo Sapien

<400> SEQUENCE: 8

```
Met Ala Leu Val Arg Gly Gly Trp Leu Trp Arg Gln Ser Ser Ile Leu
1               5                   10                  15

Arg Arg Trp Lys Arg Asn Trp Phe Ala Leu Trp Leu Asp Gly Thr Leu
            20                  25                  30

Gly Tyr Tyr His Asp Glu Thr Ala Gln Asp Glu Glu Asp Arg Val Leu
        35                  40                  45

Ile His Phe Asn Val Arg Asp Ile Lys Ile Gly Pro Glu Cys His Asp
    50                  55                  60

Val Gln Pro Pro Glu Gly Arg Ser Arg Asp Gly Leu Leu Thr Val Asn
65                  70                  75                  80

Leu Arg Glu Gly Gly Arg Leu His Leu Cys Ala Glu Thr Lys Asp Asp
            85                  90                  95

Ala Leu Ala Trp Lys Thr Ala Leu Leu Glu Ala Asn Ser Thr Pro Ala
            100                 105                 110

Pro Ala Gly Ala Thr Val Pro Pro Arg Ser Arg Arg Val Cys Ser Lys
            115                 120                 125

Val Arg Cys Val Thr Arg Ser Trp Ser Pro Cys Lys Val Glu Arg Arg
130                 135                 140

Ile Trp Val Arg Val Tyr Ser Pro Tyr Gln Asp Tyr Tyr Glu Val Val
145                 150                 155                 160

Pro Pro Asn Ala His Glu Ala Thr Tyr Val Arg Ser Tyr Tyr Gly Pro
            165                 170                 175

Pro Tyr Ala Gly Pro Gly Val Thr His Val Ile Val Arg Glu Asp Pro
            180                 185                 190

Cys Tyr Ser Ala Gly Ala Pro Leu Ala Met Gly Met Leu Ala Gly Ala
            195                 200                 205

Ala Thr Gly Ala Ala Leu Gly Ser Leu Met Trp Ser Pro Cys Trp Phe
            210                 215                 220
```

<210> SEQ ID NO 9
<211> LENGTH: 221
<212> TYPE: PRT

```
<213> ORGANISM: Murine

<400> SEQUENCE: 9

Met Ala Phe Val Lys Ser Gly Trp Leu Leu Arg Gln Ser Thr Ile Leu
 1               5                  10                  15

Lys Arg Trp Lys Lys Asn Trp Phe Asp Leu Trp Ser Asp Gly His Leu
                20                  25                  30

Ile Tyr Tyr Asp Asp Gln Thr Arg Gln Ser Ile Glu Asp Lys Val His
            35                  40                  45

Met Pro Val Asp Cys Ile Asn Ile Arg Thr Gly His Glu Cys Arg Asp
        50                  55                  60

Ile Gln Pro Pro Asp Gly Lys Pro Arg Asp Cys Leu Leu Gln Ile Val
65                  70                  75                  80

Cys Arg Asp Gly Lys Thr Ile Ser Leu Cys Ala Glu Ser Thr Asp Asp
                85                  90                  95

Cys Leu Ala Trp Lys Phe Thr Leu Gln Asp Ser Arg Thr Asn Thr Ala
            100                 105                 110

Tyr Val Gly Ser Ala Ile Leu Ser Glu Glu Thr Ala Val Ala Ala Ser
        115                 120                 125

Pro Pro Pro Tyr Ala Ala Tyr Ala Thr Pro Thr Pro Glu Val Tyr Gly
    130                 135                 140

Tyr Gly Pro Tyr Ser Gly Ala Tyr Pro Ala Gly Thr Gln Val Val Tyr
145                 150                 155                 160

Ala Ala Asn Gly Gln Ala Tyr Ala Val Pro Tyr Gln Tyr Pro Tyr Ala
                165                 170                 175

Gly Val Tyr Gly Gln Gln Pro Ala Asn Gln Val Ile Ile Arg Glu Arg
            180                 185                 190

Tyr Arg Asp Asn Asp Ser Asp Leu Ala Leu Gly Met Leu Ala Gly Ala
        195                 200                 205

Ala Thr Gly Met Ala Leu Gly Ser Leu Phe Trp Val Phe
    210                 215                 220

<210> SEQ ID NO 10
<211> LENGTH: 221
<212> TYPE: PRT
<213> ORGANISM: Homo Sapien

<400> SEQUENCE: 10

Met Ala Phe Val Lys Ser Gly Trp Leu Leu Arg Gln Ser Thr Ile Leu
 1               5                  10                  15

Lys Arg Trp Lys Lys Asn Trp Phe Asp Leu Trp Ser Asp Gly His Leu
                20                  25                  30

Ile Tyr Tyr Asp Asp Gln Thr Arg Gln Asn Ile Glu Asp Lys Val His
            35                  40                  45

Met Pro Met Asp Cys Ile Asn Ile Arg Thr Gly Gln Glu Cys Arg Asp
        50                  55                  60

Thr Gln Pro Pro Asp Gly Lys Ser Lys Asp Cys Met Leu Gln Ile Val
65                  70                  75                  80

Cys Arg Asp Gly Lys Thr Ile Ser Leu Cys Ala Glu Ser Thr Asp Asp
                85                  90                  95

Cys Leu Ala Trp Lys Phe Thr Leu Gln Asp Ser Arg Thr Asn Thr Ala
            100                 105                 110

Tyr Val Gly Ser Ala Val Met Ser Thr Asp Glu Thr Ser Val Ser Ser
        115                 120                 125

Pro Pro Pro Tyr Thr Ala Tyr Ala Ala Pro Ala Pro Glu Ala Tyr Gly
```

|  |  | 130 |  |  | 135 |  |  | 140 |  |  |
|--|--|--|--|--|--|--|--|--|--|--|

Tyr Gly Pro Tyr Gly Gly Arg Thr Arg Gln Glu Leu Lys Leu Ser Thr
145                 150                 155                 160

Leu Arg Met Gly Met Arg Met Pro Cys Pro Thr Ser Thr His Met Gln
            165                 170                 175

Asp Phe Met Asp Ser Ser Leu Leu Thr Lys Ser Ser Phe Glu Ser Ala
        180                 185                 190

Ile Glu Thr Thr Thr Ala Thr Trp His Trp Ala Cys Trp Gln Glu Ser
        195                 200                 205

Ala Thr Gly Met Ala Leu Gly Ser Leu Phe Trp Val Phe
        210                 215                 220

<210> SEQ ID NO 11
<211> LENGTH: 1875
<212> TYPE: DNA
<213> ORGANISM: Rattus

<400> SEQUENCE: 11

| | | | | | |
|--|--|--|--|--|--|
| gcctcaggct | ctctgggggt | atgcaaagcg | caggtgcgac | cagctcgggt | agcatcttca | 60 |
| tcgagtagca | gcggggcatt | tgtggcagcg | gtatccacaa | caggtgtgaa | caggtcccac | 120 |
| ccgactccac | cctggaaagt | ccttttgaag | aaatggccct | ggtgagggc | ggctggctat | 180 |
| ggagacagag | ctccatcctc | cgccgctgga | agcggaattg | gtttgctctg | tggttggatg | 240 |
| gcacgctggg | ttactaccac | gatgagacgc | acaggacga | ggaggaccgt | gtagttatcc | 300 |
| acttcaatgt | ccgagacata | aaggtcggcc | aggagtgtca | ggatgtgcag | ccccagagg | 360 |
| gcaggagccg | agatggcctg | ctgacagtga | acctacggga | gggttcccgc | ctgcacctgt | 420 |
| gcgcagagac | ccgggatgat | gccatagcat | ggaagacagc | cctgatggag | gcaaactcca | 480 |
| ccccggcccc | agctggagcc | accgtcccac | ccaggagccg | tcgggtttgc | cctaaggtca | 540 |
| ggtgtacgag | cctctcatgg | aagccctgta | aggttgagag | gcggatctgg | gtacgcgtct | 600 |
| acagtccata | tcaagactac | tatgaggtgg | taccccccaa | cgcacacgag | gccacgtatg | 660 |
| tccgcagcta | ctatgggcca | ccttatggtc | ctggtgtgac | acatgtgatc | gtgcgagagg | 720 |
| atccctgcta | cagctctggc | gccccttttgg | ccatgggcat | gcttgctggg | gctgccacgg | 780 |
| gtgctgccct | tggctcactt | atgtggtcgc | cttgctggtt | ctgagccctg | gggctccaac | 840 |
| ctctggatgt | gcacgtagaa | cgcaaaaccc | ttttcttctg | gaccctctcc | tatctaccac | 900 |
| ctaaactctg | tcccattttg | accccttttct | ctccattaag | tcctctaggc | ttggcccatt | 960 |
| cttcccacca | tttatcctcc | acttatcctc | cttccctctc | agagaaagct | aacatctcag | 1020 |
| acacagacac | agcggaacgt | ccatacacct | actgccaggc | aacctcataa | atcacatggg | 1080 |
| aatttcctct | agacacagca | aacataactt | catttggctt | taagtgtctg | aggaatggaa | 1140 |
| ctcacaagag | agcaaacaac | aaagttacag | ttacctgtct | ggcaaggata | agtggggggca | 1200 |
| agggcaaggc | agacagttta | ggtgcctaaa | ggatcacatg | acagttggct | tggcgttgtg | 1260 |
| gcaggggttg | tagtggcctt | agctttaggc | gaaggagctt | gctggataaa | ggcatgatgg | 1320 |
| ggcttttat | gaagtttctg | gatttcaact | ataatgaata | ctttgcttgt | ctagttagta | 1380 |
| ctggcagaac | atacacccctt | atccagaaca | cggcatttgg | cacctttttcc | ccacttgcta | 1440 |
| gcttccctat | gatagttcag | ctaaccctaa | ggtttcctag | ctgtggaaca | ggtgagctct | 1500 |
| ttgggacctc | tggccttaca | aagttgcttc | cattaggaaa | tgccttttctg | atcccaggag | 1560 |
| ctcagctctg | actttgactg | ttaacatctg | aagcttttttc | tcttccttca | ctctggaggg | 1620 |

-continued

| | |
|---|---|
| aaatggaatt attttgctct agggcctgac ccaccttggc accagcttgg ggaatctctc | 1680 |
| atgtgcctgt ctgtaggtgg caagcaatct ttccatttga tcccattcca aactattcca | 1740 |
| tcagtctgtc ccaattgcca atagaaaagc taaaatccct ggctcagagg ccagagtgcc | 1800 |
| cactaaaatt cctagcatat gtgagggcac cactggctca gctgcagaca ctaataaaga | 1860 |
| tatgactggc cccag | 1875 |

<210> SEQ ID NO 12
<211> LENGTH: 3282
<212> TYPE: DNA
<213> ORGANISM: Murine

<400> SEQUENCE: 12

| | |
|---|---|
| caggagaagc cggcgacctt gcgctctcag cctgatccct gtcttggcgg cctgaacatt | 60 |
| cgcagctgga gagatggcgt tcgtgaagag tggatggtta cttcggcaga gcaccattct | 120 |
| gaaacgctgg aagaagaatt ggttcgacct gtggtcagac ggtcacctga tctactacga | 180 |
| tgatcagact cggcagagca tagaggataa ggtccacatg cccgtggact gcatcaatat | 240 |
| ccgcacgggg catgagtgcc gggacatcca gcctccagat gggaagccca gagactgtct | 300 |
| gctgcagatc gtttgccgag acggaagac catcagtctc tgtgcagaga gcacagacga | 360 |
| ttgcctggca tggaagttta cactgcagga ttccagaaca aacacagctt acgttggttc | 420 |
| agcaatcctg tctgaagaga ctgcagtggc cgcgtccccg cctccctacg cagcctatgc | 480 |
| tacaccaacc cctgaggtct acggctatgg tccatacagc ggcgcatacc ccgcaggaac | 540 |
| tcaagttgtc tatgccgcca acgggcaggc atatgcagtg ccataccagt acccgtatgc | 600 |
| aggagtttat ggacaacagc ctgccaacca agtcatcatc cgcgagcggt accgagacaa | 660 |
| tgacagtgac ctggctctgg gcatgctcgc cggggcagcc accggcatgg ccctgggctc | 720 |
| tctgttctgg gtcttctaga gccttcaaca ttttctgtgc atagcttctg ttagtcctgt | 780 |
| gtgcagtaat ttgatttgca gggcatttct gtttgtgaca agtgtctttc ataataattt | 840 |
| aaatagttct tttgaaggtg gtaatctaat aattgtgact gacctgcatg gtaccacaaa | 900 |
| gaaagcccga ggtatgctgt gagtgagagc ctgagtcctt ccgggtacta gcttgcacca | 960 |
| agtctttctt agggactttt ggatggcttt atgtaaacac acccagttaa atgggcaatt | 1020 |
| tccgtccagt taggtgcagt gttgaattaa gggatggctt tccttgctat gccaatacta | 1080 |
| atactgctga tggaggaaga tgtgtgcaag tgtggtgagg agagtcacag cttctttaac | 1140 |
| tgtggattct cttctagacc cctgctgcgt gttaccctag gagctgtggg ctggtggctc | 1200 |
| ctgcaagact atggtgtgag gaccctgtaa cgtacctctt ggagcactta ggtaccccctt | 1260 |
| gaagctccta ggtatcacca gcaggattgg ctgctcagga tgcagagggc cacccctcc | 1320 |
| ctttaaaaat tacgctccag taatctgccc agttttattt tcttgttatt cttctgtttg | 1380 |
| cttttcctgg ggatgattgg cattagtctg gagttaggaa ttgattcgag tgccggtggg | 1440 |
| tggaggcatg cagggagctg cccagcgacc tgctctcagt gtctgcttta ggcgtattga | 1500 |
| ttgccagccc agtctgcaga gagcctatag agcctatttt tctacttgta aagaaagtat | 1560 |
| agtgagggga attggggaga gccttacttg gaatgttcct gcctcaggcc ttctgggacc | 1620 |
| caagcttcac gggatgctct ttaactcctg gtgaggctct tcctcggcag gcagtggttg | 1680 |
| ggaggccccg tgggtgtcca gagagactca ggttttgagt gagaaatggg gattgggtag | 1740 |
| agaccatctc agggattcgt tctaatccct catgttagtg gggatccagc cttgttctca | 1800 |
| gtcctgaccg cctcacagca gaagagctta aacatttct ggtcccaaat gtgtggcact | 1860 |

```
ctgagaagct cacaatctgg ctttctaacg aaaatttgta tttctaaaat tagagaatac    1920
atgttccacg catttaaaat ttatgttctt tcatgtttta aagctcccaa atccagcttt    1980
gtgactggca tattttagtt tcaaacagta ccccggcaca aaggtgggat ggcacagtga    2040
aggccccccg ccctctactt tgcatagtct tgtttctcca gggtgctccc aggaagcatt    2100
cattctgact ttgctcagcc cagtgcatgc gtgctgcctt gccgccgtgc tgctgggtag    2160
ctctttcttg gtcagatcaa gtcttcaaca gatctccatg tgagacagtt gccaagtaga    2220
tgaggtggtg cccatagtgc tttctcgata ctccttgggg acctgttgac acctgcccat    2280
ttccagctga catttgtttt tctgtcatct ctgatagatg ggatatgtga caacatggta    2340
cggacgccgt ccaacgtcgc tttaataagc atgatgctga ttttacatcc tgtgctgtat    2400
gactgccatt tgctcacagt gtcaccattg ctaaagctcc gtgctttact tacaaaacac    2460
taaaaccagt ggttagtgtt tcacagtgat tttaatttta gagttagtta ctggcattcc    2520
taaagccata gagtactgag tcacatccct gaagtacttt tgaaacagaa ttgtctccta    2580
ctgtcccatg ggtgtgccct gcctgtctcc tggccccaat ggcgtagctg taccaggcag    2640
ccatagttga gcctgatcat tcctgtcacc agtttgactt gattatatac ccagaatgga    2700
atacattctt gggcatctca gttcctcagc cctgatcctc atagacgcca ccctttcgat    2760
ggcttttgcg gcgtcacttg tacctcagtg agtcctgcga ttcttgagtt agagggaacg    2820
acttgtccag cattgaggaa catgtctcct ccactgagac ttaaatgatg atgcagggct    2880
ggaagaggct ggctgctgac actgcatcgt ggctgatgtc attgctctcc tagttctttg    2940
atttaagaac ctttcatatg gaaggcctga ggtccctcag atcgtccctt gccaagaagg    3000
cctggcttag gtcattagtg cccacagtag ccttctggag tgtagcaagt tcctgcgttt    3060
gagacagaat ggttcagatt tattttctac atctgttgtt gacccatgc accctctcat    3120
tttgccttcc agtctacgta gatgaaagat gaaaggcaga ggatgcagac agtcttcttt    3180
gtgattgctt ctgttattct gttgcatcta ccgagcccgt tttctccctg tctgtgcata    3240
cagtatgttt ataagtgaac ttgttaaaat attaaatgat ca                      3282
```

<210> SEQ ID NO 13
<211> LENGTH: 110
<212> TYPE: PRT
<213> ORGANISM: Rattus
<220> FEATURE:
<221> NAME/KEY: DOMAIN
<222> LOCATION: (1)...(110)
<223> OTHER INFORMATION: Pleckstrin homology domain

<400> SEQUENCE: 13

```
Met Asn Asp Val Ala Ile Val Lys Glu Gly Trp Leu His Lys Arg Gly
 1               5                  10                  15

Glu Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Glu Gln Arg
            35                  40                  45

Glu Ser Pro Leu Asn Asn Phe Ser Val Ala Gln Cys Gln Leu Met Lys
        50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95
```

Glu Glu Trp Thr Thr Ala Ile Gln Thr Val Ala Asp Gly Leu
            100                 105                 110

<210> SEQ ID NO 14
<211> LENGTH: 98
<212> TYPE: PRT
<213> ORGANISM: Homo sapiens
<220> FEATURE:
<221> NAME/KEY: DOMAIN
<222> LOCATION: (1)...(98)
<223> OTHER INFORMATION: Pleckstrin homology domain

<400> SEQUENCE: 14

Gly Ser Gly Ser Ala Arg Glu Gly Trp Leu Phe Lys Trp Thr Asn Tyr
 1               5                  10                  15

Ile Lys Gly Tyr Gln Arg Arg Trp Phe Val Leu Ser Asn Gly Leu Leu
            20                  25                  30

Ser Tyr Tyr Arg Ser Lys Ala Glu Met Arg His Thr Cys Arg Gly Thr
        35                  40                  45

Ile Asn Leu Ala Thr Ala Asn Ile Thr Val Glu Asp Ser Cys Asn Phe
    50                  55                  60

Ile Ile Ser Asn Gly Gly Ala Gln Thr Tyr His Leu Lys Ala Ser Ser
65                  70                  75                  80

Glu Val Glu Arg Gln Arg Trp Val Thr Ala Leu Glu Leu Ala Lys Ala
                85                  90                  95

Lys Ala

<210> SEQ ID NO 15
<211> LENGTH: 112
<212> TYPE: PRT
<213> ORGANISM: Murine
<220> FEATURE:
<221> NAME/KEY: DOMAIN
<222> LOCATION: (1)...(112)
<223> OTHER INFORMATION: Pleckstrin homology domain

<400> SEQUENCE: 15

Asp Glu Ile Leu Val Ile Arg Lys Gly Trp Leu Thr Ile Asn Asn Ser
 1               5                  10                  15

Gly Ile Met Lys Gly Gly Ser Lys Glu Tyr Trp Phe Val Leu Thr Ala
            20                  25                  30

Glu Asn Leu Ser Trp Tyr Lys Asp Asp Glu Glu Lys Glu Lys Lys Tyr
        35                  40                  45

Met Leu Ser Val Asp Asn Leu Lys Leu Arg Asp Val Glu Lys Gly Phe
    50                  55                  60

Met Ser Ser Lys His Ile Phe Ala Leu Phe Asn Thr Glu Gln Arg Asn
65                  70                  75                  80

Val Tyr Lys Asp Asn Arg Gln Leu Glu Leu Ala Cys Glu Thr Gln Glu
                85                  90                  95

Glu Val Asp Ser Trp Lys Ala Ser Phe Leu Arg Ala Gly Val Tyr Pro
            100                 105                 110

<210> SEQ ID NO 16
<211> LENGTH: 124
<212> TYPE: PRT
<213> ORGANISM: Homo sapiens
<220> FEATURE:
<221> NAME/KEY: DOMAIN
<222> LOCATION: (1)...(124)
<223> OTHER INFORMATION: Pleckstrin homology domain

<400> SEQUENCE: 16

-continued

```
Thr His Thr Phe Phe Asn Pro Asp Arg Glu Gly Trp Leu Leu Lys Leu
 1               5                  10                  15

Gly Gly Arg Val Lys Thr Trp Lys Arg Arg Trp Phe Ile Leu Thr Asp
            20                  25                  30

Asn Cys Leu Tyr Tyr Phe Glu Tyr Thr Thr Asp Lys Glu Pro Arg Gly
            35                  40                  45

Ile Ile Pro Leu Glu Asn Leu Ser Ile Arg Glu Val Asp Asp Pro Arg
 50                      55                  60

Lys Pro Asn Cys Phe Glu Leu Tyr Ile Pro Asn Asn Lys Gly Gln Leu
 65                  70                      75                  80

Ile Lys Ala Cys Lys Thr Glu Ala Asp Gly Arg Val Val Glu Gly Asn
                85                  90                      95

His Met Val Tyr Arg Ile Ser Ala Pro Thr Gln Glu Glu Lys Asp Glu
                100                     105                     110

Trp Ile Lys Ser Ile Gln Ala Ala Val Ser Val Asp
            115                     120
```

<210> SEQ ID NO 17
<211> LENGTH: 103
<212> TYPE: PRT
<213> ORGANISM: Homo sapiens
<220> FEATURE:
<221> NAME/KEY: DOMAIN
<222> LOCATION: (1)...(103)
<223> OTHER INFORMATION: Pleckstrin homology domain

<400> SEQUENCE: 17

```
Met Glu Pro Lys Arg Ile Arg Glu Gly Tyr Leu Val Lys Lys Gly Ser
 1               5                  10                  15

Val Phe Asn Thr Trp Lys Pro Met Trp Val Val Leu Leu Glu Asp Gly
            20                  25                  30

Ile Glu Phe Tyr Lys Lys Lys Ser Asp Asn Ser Pro Lys Gly Met Ile
            35                  40                  45

Pro Leu Lys Gly Ser Thr Leu Thr Ser Pro Cys Gln Asp Phe Gly Lys
 50                      55                  60

Arg Met Phe Val Phe Lys Ile Thr Thr Thr Lys Gln Gln Asp His Phe
 65                  70                      75                  80

Phe Gln Ala Ala Phe Leu Glu Glu Arg Asp Ala Trp Val Arg Asp Ile
                85                  90                      95

Asn Lys Ala Ile Lys Cys Ile
                100
```